US008404247B2

(12) United States Patent
Young et al.

(10) Patent No.: US 8,404,247 B2
(45) Date of Patent: *Mar. 26, 2013

(54) ANTITOXIN AND VACCINE PLATFORM BASED ON NODAVIRUS VLPS

(75) Inventors: John Young, San Diego, CA (US); Anette Schneemann, San Diego, CA (US); Marianne Manchester, San Diego, CA (US); Kelly Dryden, San Diego, CA (US); John M. Marlett, San Diego, CA (US); Darly Joseph Manayani, San Diego, CA (US); Godfrey Jonah Anderson Rainey, Kensington, MD (US); Vijay Reddy, San Diego, CA (US); Marc E. Siladi, San Diego, CA (US); Heather M. Scobie, Hamden, CT (US); Diane Thomas, San Diego, CA (US); Mark Yeager, Del Mar, CA (US)

(73) Assignees: The Salk Institute for Biological Studies, La Jolla, CA (US); The Scripps Research Institute, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/167,627

(22) Filed: Jun. 23, 2011

(65) Prior Publication Data
US 2012/0156237 A1   Jun. 21, 2012

Related U.S. Application Data

(63) Continuation of application No. 12/070,384, filed on Feb. 14, 2008, now Pat. No. 7,998,487.

(60) Provisional application No. 60/967,918, filed on Sep. 7, 2007, provisional application No. 60/928,261, filed on May 7, 2007, provisional application No. 60/902,485, filed on Feb. 20, 2007, provisional application No. 60/901,791, filed on Feb. 16, 2007.

(51) Int. Cl.
*A61K 39/385*   (2006.01)
*A61K 39/07*    (2006.01)
*A61K 39/08*    (2006.01)
*A61K 39/116*   (2006.01)
*A61K 39/295*   (2006.01)

(52) U.S. Cl. ........... 424/196.11; 424/197.11; 424/246.1; 424/247.1; 424/203.1; 424/201.1

(58) Field of Classification Search ........................ None
See application file for complete search history.

(56) References Cited

U.S. PATENT DOCUMENTS

| | | | |
|---|---|---|---|
| 5,932,426 A | | 8/1999 | Baralle et al. |
| 6,171,591 B1 * | | 1/2001 | Hall ............ 424/186.1 |
| 7,998,487 B2 * | | 8/2011 | Young et al. ............ 424/196.11 |
| 2003/0054010 A1 * | | 3/2003 | Sebbel et al. ............ 424/185.1 |
| 2003/0235818 A1 | | 12/2003 | Katritch et al. |
| 2004/0076611 A1 | | 4/2004 | Bachmann et al. |
| 2005/0175588 A1 | | 8/2005 | Mosca |
| 2005/0186621 A1 | | 8/2005 | Galarza et al. |
| 2005/0214321 A1 | | 9/2005 | Rasochova et al. |

OTHER PUBLICATIONS

Ogasawara et al (In Vivo 20:319-324, 2006; in IDS).*
Lee et al (Vaccine 24:6886-6892, 2006).*
Shivachandra et al (Vaccine 25:1225-1235, 2007; in IDS).*
Bradley et la. (2001) "Identification of the cellular receptor for anthrax toxin." *Nature*, 414(6860): 225-229.
Buratti et al. (1996) "Conformational display of two neutralizing epitopes of HIV-1 gp41 on the Flock House virus capsid protein." *Journal of Immunological Methods*, 197: 7-18.
Fehr et al. (1998) "T cell-independent type I antibody response against B cell epitopes expressed repetitively on recombinant virus particles." PNAS, 95(16): 9477-9481.
Gubbins et al. (2006) "Production and characterization of neutralizing monoclonal antibodies that recognize an epitope in domain 2 of *Bacillus anthracis* protective antigen," FEMS Immunology and Medical Microbiology, 47(3)436-443.
Krishna et al. (2003) "Analysis of RNA packaging in wild-type and mosaic protein capsids of flock house virus using recombinant baculovirus vectors." *Virology*, 305(1): 10-24.
Lacy et al. (2004) "Crystal structure of the von Willebrand factor A domain of human capillary morphogenesis protein 2: an anthrax toxin receptor." PNAS, 101(17): 6367-6372.
Manayani et al. (2007) "A Viral Nanoparticle with Dual Funtion as a Anthrax Antitoxin and Vaccine." *PloS Pathogens*, 3(10): e142.
Ogasawara et al. (2006) "Recombinant Viral-like Particles of Parvivirus B19 as Antigen Carriers of Anthrax Protective Antigen." In Vivo, 20: 319-324.
Schneemann et al. (1993) "Use of recombinant baculoviruses in synthesis of morphologically distinct viruslike particles of flock house virus, a nodavirus." *J. Virol.* 67(5): 2756-2763.
Scobie et al. (2003) "Human capillary morphogenesis protein 2 functions as an anthrax toxin receptor." PNAS, 100(9): 5170-5174.
Scobie et al. (2005) "A soluble receptor decoy protects rats against anthrax lethal toxin challenge." *J Infect Dis* 192(6): 1047-1051.
Scobie et al. (2006) "Anthrax toxin receptor 2-dependent lethal toxin killing in vivo." *PloS Pathlog* 2(10): e111.
Shivachandra et al. (2006) "In vitro binding of anthrax protective antigen on bacteriophage T4 capsid surface through Hoc-capsid interactions: a strategy for efficient displays of large full-length proteins." *Virology*, 345(1): 190-198.
Shivachandra et al. (2007) "Multicomponent anthrax toxin display and delivery using bacteriophage T4." *Vaccine*, 25(7): 1225-1235.
Smallshaw et al.(2005) "Preclinical toxicity and efficacy testing of RiVax, a recombinant protein vaccine against ricin." *Vaccine*, 23: 4775-4784.
Venter et al. (2005) "Capsid protein synthesis from replicating RNA directs specific packaging of the genome of a multipartite, positive-strand RNA virus." *J. Virol*, 79(10): 6239-6248.
Vitale et al. (2006) "Prophylaxis and therapy of inhalational anthrax y a novel monoclonal antibody to protective antigen that mimics vaccine-induced immunity." *Infect lmmun*, 74(10): 5840-5847.
Wigelsworth et al. (2004) "Binding stoichiometry and kinetics of the interaction of a human anthrax toxin receptor, CMG2, with protective antigen." *J Biol. Chem.*, 279(22): 23349-23356.
Zhang et al. (2006) "The 2β2-2β3 loop of anthrax protective antigen contains a dominant neutralizing epitope," Biochemical and Biophysical Research Communications, 341(4):1164-1171.

* cited by examiner

*Primary Examiner* — Mary E Mosher
(74) *Attorney, Agent, or Firm* — Barnes & Thornburg LLP

(57) ABSTRACT

Antitoxin and vaccine compositions based on nodavirus VLPs are provided. Anthrax antitoxin and vaccine compositions are provided. Methods of treating toxins with VLP-based antitoxins are provided. Methods of raising an immune response with immunogen decorated VLPs are provided.

11 Claims, 9 Drawing Sheets

SEQUENCE LISTING

```
<160> NUMBER OF SEQ ID NOS: 3

<210> SEQ ID NO 1
<211> LENGTH: 585
<212> TYPE: PRT
<213> ORGANISM: Artificial Sequence
<220> FEATURE:
<223> OTHER INFORMATION: Amino acid sequence of FHV-CMG2 chimera 264

<400> SEQUENCE: 1

Met Val Asn Asn Asn Arg Pro Arg Arg Gln Arg Ala Gln Arg Val Val
1               5                   10                  15

Val Thr Thr Thr Gln Thr Ala Pro Val Pro Gln Gln Asn Val Pro Arg
            20                  25                  30

Asn Gly Arg Arg Arg Arg Asn Arg Thr Arg Arg Asn Arg Arg Arg Val
        35                  40                  45

Arg Gly Met Asn Met Ala Ala Leu Thr Arg Leu Ser Gln Pro Gly Leu
    50                  55                  60
```

-continued

Ala Phe Leu Lys Cys Ala Phe Ala Pro Pro Asp Phe Asn Thr Asp Pro
65                  70                  75                  80

Gly Lys Gly Ile Pro Asp Arg Phe Glu Gly Lys Val Val Ser Arg Lys
                85                  90                  95

Asp Val Leu Asn Gln Ser Ile Ser Phe Thr Ala Gly Gln Asp Thr Phe
            100                 105                 110

Ile Leu Ile Ala Pro Thr Pro Gly Val Ala Tyr Trp Ser Ala Ser Val
        115                 120                 125

Pro Ala Gly Thr Phe Pro Thr Ser Ala Thr Thr Phe Asn Pro Val Asn
130                 135                 140

Tyr Pro Gly Phe Thr Ser Met Phe Gly Thr Thr Ser Thr Ser Arg Ser
145                 150                 155                 160

Asp Gln Val Ser Ser Phe Arg Tyr Ala Ser Met Asn Val Gly Ile Tyr
                165                 170                 175

Pro Thr Ser Asn Leu Met Gln Phe Ala Gly Ser Ile Thr Val Trp Lys
            180                 185                 190

Cys Pro Val Lys Leu Ser Thr Val Gln Phe Pro Val Ala Thr Asp Pro
        195                 200                 205

Ala Thr Ser Ser Leu Val His Thr Leu Val Gly Leu Asp Gly Val Leu
210                 215                 220

Ala Val Gly Pro Asp Asn Phe Ser Glu Ser Phe Ile Lys Gly Val Phe
225                 230                 235                 240

Ser Gln Ser Ala Cys Asn Glu Pro Asp Phe Glu Phe Asn Asp Ile Leu
                245                 250                 255

Glu Gly Ile Gln Thr Leu Pro Pro Ser Cys Arg Arg Ala Phe Asp Leu
            260                 265                 270

Tyr Phe Val Leu Asp Lys Ser Gly Ser Val Ala Asn Asn Trp Ile Glu
        275                 280                 285

Ile Tyr Asn Phe Val Gln Gln Leu Ala Glu Arg Phe Val Ser Pro Glu
290                 295                 300

Met Arg Leu Ser Phe Ile Val Phe Ser Ser Gln Ala Thr Ile Ile Leu
305                 310                 315                 320

Pro Leu Thr Gly Asp Arg Gly Lys Ile Ser Lys Gly Leu Glu Asp Leu
                325                 330                 335

Lys Arg Val Ser Pro Val Gly Glu Thr Tyr Ile His Glu Gly Leu Lys
            340                 345                 350

Leu Ala Asn Glu Gln Ile Gln Lys Ala Gly Gly Leu Lys Thr Ser Ser
        355                 360                 365

Ile Ile Ile Ala Leu Thr Asp Gly Lys Leu Asp Gly Leu Val Pro Ser
370                 375                 380

Tyr Ala Glu Lys Glu Ala Lys Ile Ser Arg Ser Leu Gly Ala Ser Val
385                 390                 395                 400

Tyr Cys Val Gly Val Leu Asp Phe Glu Gln Ala Gln Leu Glu Arg Ile
                405                 410                 415

Ala Asp Ser Lys Glu Gln Val Phe Pro Val Lys Gly Gly Phe Gln Ala
            420                 425                 430

Leu Lys Gly Ile Ile Asn Ser Ile Leu Ala Gln Ser Cys Ser Leu Gly
        435                 440                 445

Ser Thr Gly Gln Pro Phe Thr Met Asp Ser Gly Ala Glu Ala Thr Ser
450                 455                 460

Gly Val Val Gly Trp Gly Asn Met Asp Thr Ile Val Ile Arg Val Ser
465                 470                 475                 480

Ala Pro Glu Gly Ala Val Asn Ser Ala Ile Leu Lys Ala Trp Ser Cys
                485                 490                 495

-continued

Ile Glu Tyr Arg Pro Asn Pro Asn Ala Met Leu Tyr Gln Phe Gly His
            500                 505                 510

Asp Ser Pro Pro Leu Asp Glu Val Ala Leu Gln Glu Tyr Arg Thr Val
            515                 520                 525

Ala Arg Ser Leu Pro Val Ala Val Ile Ala Ala Gln Asn Ala Ser Met
        530                 535                 540

Trp Glu Arg Val Lys Ser Ile Ile Lys Ser Ser Leu Ala Ala Ala Ser
545                 550                 555                 560

Asn Ile Pro Gly Pro Ile Gly Val Ala Ser Gly Ile Ser Gly Leu
                565                 570                 575

Ser Ala Leu Phe Glu Gly Phe Gly Phe
            580                 585

<210> SEQ ID NO 2
<211> LENGTH: 588
<212> TYPE: PRT
<213> ORGANISM: Artificial Sequence
<220> FEATURE:
<223> OTHER INFORMATION: Amino acid sequence of FHV-CMG2 chimera 206

<400> SEQUENCE: 2

Met Val Asn Asn Arg Pro Arg Arg Gln Arg Ala Gln Arg Val Val
1               5                   10                  15

Val Thr Thr Thr Gln Thr Ala Pro Val Pro Gln Gln Asn Val Pro Arg
            20                  25                  30

Asn Gly Arg Arg Arg Arg Asn Arg Thr Arg Arg Asn Arg Arg Arg Val
        35                  40                  45

Arg Gly Met Asn Met Ala Ala Leu Thr Arg Leu Ser Gln Pro Gly Leu
    50                  55                  60

Ala Phe Leu Lys Cys Ala Phe Ala Pro Pro Asp Phe Asn Thr Asp Pro
65                  70                  75                  80

Gly Lys Gly Ile Pro Asp Arg Phe Glu Gly Lys Val Val Ser Arg Lys
                85                  90                  95

Asp Val Leu Asn Gln Ser Ile Ser Phe Thr Ala Gly Gln Asp Thr Phe
            100                 105                 110

Ile Leu Ile Ala Pro Thr Pro Gly Val Ala Tyr Trp Ser Ala Ser Val
        115                 120                 125

Pro Ala Gly Thr Phe Pro Thr Ser Ala Thr Thr Phe Asn Pro Val Asn
    130                 135                 140

Tyr Pro Gly Phe Thr Ser Met Phe Gly Thr Thr Ser Thr Ser Arg Ser
145                 150                 155                 160

Asp Gln Val Ser Ser Phe Arg Tyr Ala Ser Met Asn Val Gly Ile Tyr
                165                 170                 175

Pro Thr Ser Asn Leu Met Gln Phe Ala Gly Ser Ile Thr Val Trp Lys
            180                 185                 190

Cys Pro Val Lys Leu Ser Thr Val Gln Phe Pro Val Ala Thr Ser Cys
        195                 200                 205

Arg Arg Ala Phe Asp Leu Tyr Phe Val Leu Asp Lys Ser Gly Ser Val
    210                 215                 220

Ala Asn Asn Trp Ile Glu Ile Tyr Asn Phe Val Gln Gln Leu Ala Glu
225                 230                 235                 240

Arg Phe Val Ser Pro Glu Met Arg Leu Ser Phe Ile Val Phe Ser Ser
                245                 250                 255

Gln Ala Thr Ile Ile Leu Pro Leu Thr Gly Asp Arg Gly Lys Ile Ser
            260                 265                 270

-continued

```
Lys Gly Leu Glu Asp Leu Lys Arg Val Ser Pro Val Gly Glu Thr Tyr
            275                 280                 285

Ile His Glu Gly Leu Lys Leu Ala Asn Glu Gln Ile Gln Lys Ala Gly
        290                 295                 300

Gly Leu Lys Thr Ser Ser Ile Ile Ala Leu Thr Asp Gly Lys Leu
305                 310                 315                 320

Asp Gly Leu Val Pro Ser Tyr Ala Glu Lys Glu Ala Lys Ile Ser Arg
                325                 330                 335

Ser Leu Gly Ala Ser Val Tyr Cys Val Gly Val Leu Asp Phe Glu Gln
            340                 345                 350

Ala Gln Leu Glu Arg Ile Ala Asp Ser Lys Glu Gln Val Phe Pro Val
        355                 360                 365

Lys Gly Gly Phe Gln Ala Leu Lys Gly Ile Ile Asn Ser Ile Leu Ala
    370                 375                 380

Gln Ser Cys Ala Glu Ala Thr Ser Ser Leu Val His Thr Leu Val Gly
385                 390                 395                 400

Leu Asp Gly Val Leu Ala Val Gly Pro Asp Asn Phe Ser Glu Ser Phe
                405                 410                 415

Ile Lys Gly Val Phe Ser Gln Ser Ala Cys Asn Glu Pro Asp Phe Glu
            420                 425                 430

Phe Asn Asp Ile Leu Glu Gly Ile Gln Thr Leu Pro Pro Ala Asn Val
        435                 440                 445

Ser Leu Gly Ser Thr Gly Gln Pro Phe Thr Met Asp Ser Gly Ala Glu
    450                 455                 460

Ala Thr Ser Gly Val Val Gly Trp Gly Asn Met Asp Thr Ile Val Ile
465                 470                 475                 480

Arg Val Ser Ala Pro Glu Gly Ala Val Asn Ser Ala Ile Leu Lys Ala
                485                 490                 495

Trp Ser Cys Ile Glu Tyr Arg Pro Asn Pro Asn Ala Met Leu Tyr Gln
            500                 505                 510

Phe Gly His Asp Ser Pro Pro Leu Asp Glu Val Ala Leu Gln Glu Tyr
        515                 520                 525

Arg Thr Val Ala Arg Ser Leu Pro Val Ala Val Ile Ala Ala Gln Asn
    530                 535                 540

Ala Ser Met Trp Glu Arg Val Lys Ser Ile Ile Lys Ser Ser Leu Ala
545                 550                 555                 560

Ala Ala Ser Asn Ile Pro Gly Pro Ile Gly Val Ala Ala Ser Gly Ile
                565                 570                 575

Ser Gly Leu Ser Ala Leu Phe Glu Gly Phe Gly Phe
            580                 585
```

```
<210> SEQ ID NO 3
<211> LENGTH: 1400
<212> TYPE: DNA
<213> ORGANISM: flock house virus

<400> SEQUENCE: 3
gtaaacaatt ccaagttcca aaatggttaa taacaacaga ccaagacgtc aacgagctca    60
acgcgttgtc gtcacaacaa cccaaacagc gcctgttcca cagcaaaacg tgccacgtaa   120
tggtagacgc cgacgtaatc gcacgaggcg taatcgccga cgtgtgcgcg gaatgaacat   180
ggcggcgcta accagattaa gtcaacctgg tttggcgttt ctcaaatgtg catttgcacc   240
acctgacttc aacaccgacc ccggtaaggg aatacctgat agatttgaag caaagtggt   300 cagcccgaaag gatgtcctca atcaatctat cagctttact gccggacagg acacttttat   360
```

-continued

```
actcatcgca cctaccccg gagtcgccta ctggagtgct agcgttcctg ctggtacttt      420
tcctactagt gcgactacgt ttaaccccgt taattatccg ggttttacat cgatgttcgg      480
aacaacttca acatctaggt ccgatcaggt gtcctcattc aggtacgctt ccatgaacgt      540
gggtatttac ccaacgtcga acttgatgca gtttgccgga agcataactg tttggaaatg      600
ccctgtaaag ctgagtactg tgcaattccc ggttgcaaca gatccagcca ccagttcgct      660
agttcatact cttgttggtt tagatggtgt tctagcggtg gggcctgaca acttctctga      720
gtcattcatc aaaggagtgt tttcacagtc ggcttgtaac gagcctgact ttgaattcaa      780
tgacatattg gagggtatcc agacattgcc acctgctaat gtgtcccttg gttctacggg      840 tcaaccttt accatggact caggagcaga agccaccagt ggagtagtcg gatggggcaa      900
tatggacacg attgtcatcc gtgtctcggc ccctgagggc gcagttaact ctgccatact      960
caaggcatgg tcctgcattg agtatcgacc aaatccaaac gccatgttat accaattcgg     1020
ccatgattcg cctcctctcg atgaggtcgc gcttcaggaa taccgtacgg ttgccagatc     1080
tttgccggtt gcagtgatag cggcccaaaa tgcatcaatg tgggagagag tgaaatccat     1140
cattaaatcc tccctggctg ctgcaagcaa cattcccggc ccgatcggtg tcgccgcaag     1200
tggtattagt ggactgtcag ccctttttga aggatttggc ttttagaagc atccggacgc     1260
caacctaacc gggcaagtat ccgaacaatc ggacatttgg ccacaataag cccaatttgg     1320
ttgaagatta aagtagtgag ccccccttagc gcgaaaccgg aatttatatt ccaaaccagt     1380
ttaagtcaac agactaaggt                                                  1400
```

ANTITOXIN AND VACCINE PLATFORM BASED ON NODAVIRUS VLPS

CROSS REFERENCE TO RELATED APPLICATIONS

The subject patent application is a continuation of U.S. Ser. No. 12/070,384 filed Feb. 14, 2008, now U.S. Pat. No. 7,998,487, which claims priority to and benefit of each of the following prior patent applications: U.S. Ser. No. 60/967,918 filed Sep. 7, 2007, by Young et al., entitled "A NOVEL ANTITOXIN AND VACCINE PLATFORM BASED ON NODAVIRUS VLPS"; U.S. Ser. No. 60/928,261 filed May 7, 2007, by Young et al., entitled "A NOVEL ANTITOXIN AND VACCINE PLATFORM BASED ON NODAVIRUS VLPS"; U.S. Ser. No. 60/902,485 filed Feb. 20, 2007, by Young et al., entitled "A NOVEL ANTITOXIN AND VACCINE PLATFORM BASED ON NODAVIRUS VLPS"; and U.S. Ser. No. 60/901,791 filed Feb. 16, 2007, by Young et al., entitled "A NOVEL ANTITOXIN AND VACCINE PLATFORM BASED ON NODAVIRUS VLPS." Each of these prior applications is incorporated herein by reference in its entirety.

STATEMENT AS TO RIGHTS TO INVENTIONS MADE UNDER FEDERALLY SPONSORED RESEARCH

This invention was made with government support under Contract Nos. AI056013 and GM066084 awarded by the National Institutes of Health. The government has certain rights in this invention.

FIELD OF THE INVENTION

The invention is in the field of antitoxins and vaccines based on nodavirus VLPs. Anthrax antitoxins and vaccines are preferred embodiments of the invention.

BACKGROUND OF THE INVENTION

A variety of diseases are modulated by bacterial and other toxins. Antitoxins to treat many such diseases exist, often as antibodies against the relevant toxin molecule. For example, antibodies against diphtheria are raised (classically, in horses) and administered as an antitoxin against diphtheria. However, even where such antitoxins are available, they may not provide optimal protection, and often have undesired side effects. Moreover, for some serious illnesses such as *Bacillus anthracis* infection, effective antitoxins are not available at all.

Anthrax is caused by the spore-forming, gram-positive bacterium *Bacillus anthracis*[1]. The disease is elicited when spores are inhaled, ingested or transmitted through open wounds in the skin. Inhalational anthrax is the deadliest form of the disease primarily because it is difficult to diagnose in a timely manner. Disease symptoms are initially nonspecific and systemic dissemination of anthrax toxin can occur prior to antibiotic treatment[2]. The deliberate release of *B. anthracis* spores in the U.S. in 2001 with the ensuing human fatalities and enormous cleanup costs has underscored the need for better detection, treatment and prevention of anthrax.

The toxic effects of anthrax are predominantly due to an AB-type toxin made up of a single, receptor-binding B subunit and two enzymatic A subunits[3]. The A subunits are edema factor (EF, 89 kD), an adenylate cyclase that raises intracellular cAMP levels[4], and lethal factor (LF, 90 kD), a zinc protease that cleaves mitogen-activated protein kinase kinases[5,6]. The receptor binding B subunit is protective antigen (PA), which is initially synthesized as an 83 kD precursor. Upon receptor binding, PA83 is cleaved by furin into a 63 kD product, which forms heptamers that bind EF to form edema toxin (EdTx) and LF to form lethal toxin (LeTx)[3]. Two anthrax toxin receptors, widely distributed on human cells, have been identified: anthrax toxin receptor/tumor endothelial marker 8 (ANTXR1)[7] and capillary morphogenesis gene 2 (ANTXR2)[8]. Although both receptors bind PA through a 200 amino acid extracellular von Willebrand factor A (VWA) domain, the VWA domain of ANTXR2 has a 1000-fold higher binding affinity for PA than the VWA domain of ANTXR1. In addition, ANTXR2 has been shown to mediate intoxication in vivo[9-11]. Recently, the LDL receptor-related protein LRP6 was shown to function as a co-receptor for anthrax toxin internalization[12].

The potential use of anthrax and other diseases as weapons of bioterrorism has prompted increased efforts to develop better antitoxins and vaccines. In the case of anthrax, protective immunity to *B. anthracis* infection is conferred by antibodies against PA, which is the primary component of anthrax-vaccine adsorbed (AVA; Biothrax), the only currently licensed anthrax vaccine in the US. Although AVA is safe and effective, it is molecularly ill-defined, can cause adverse reactions and is administered in a lengthy immunization schedule (6 doses over 18 months)[13]. A second-generation vaccine based on recombinant PA adsorbed on aluminum hydroxide as adjuvant is currently in development. Preliminary data indicate that it is less potent than AVA and it is likely that several immunizations will be required to confer protection in humans[14]. Thus, the development of a well-characterized vaccine that induces rapid immunity after a single injection remains an important goal.

A general and widely adaptable vaccine platform to raise an immune response against anthrax and/or other serious diseases would be highly desirable. The present invention provides such a platform for use as either an antitoxin or a vaccine platform.

SUMMARY OF THE INVENTION

The present invention provides a general and widely adaptable antitoxin and vaccine platform. Recombinant nodavirus-derived virus like particles (VLPs) display toxin binding domains, and can be used as a multivalent antitoxin. In addition, these VLPs can be decorated with toxin, providing a multivalent immunogen that can be used to raise an immune response against the displayed toxin moieties. In one particularly useful example, anthrax antitoxins and immunogens are provided for use in treating or preventing anthrax infection.

Accordingly, in a first aspect, the invention provides an antitoxin comprising a nodavirus-derived virus like particle (VLP) that displays a heterologous toxin binding domain.

In one particularly preferred embodiment, the antitoxin comprises an anthrax antitoxin and the heterologous toxin binding domain comprises a polypeptide sequence that binds to a component of an anthrax toxin. For example, the polypeptide sequence optionally binds to anthrax protective antigen (PA). In this example, the polypeptide sequence can include a PA binding subsequence of an extracellular von Willebrand factor A (VWA) domain, e.g., an ANTRX2 protein VWA domain. In one specific example, the ANTRX2 VWA domain includes residues 38-218 of the VWA domain.

The VLP can be derived from any of a variety of nodaviruses. In one preferred embodiment, the VLP is derived from Flock House Virus (FHV). FHV and other nodaviruses comprise loop domains on the capsid/coat proteins of the virus, into which heterologous polypeptide sequences can be inserted. For example, the ANTRX2 VWA domain can be inserted in place of residues 265-267 of a FHV coat protein of the VLP. Up to about 180 copies of the heterologous polypeptide (e.g., toxin binding domain) can be displayed on an exterior surface of the VLP.

In a related aspect, the invention provides an immunogenic composition comprising a nodavirus-derived virus like particle (VLP) that comprises a heterologous immunogen binding domain, which binding domain is bound to a heterologous immunogen. This "decorated" VLP can be used as a polyvalent immunogen and can act as a potent vaccine against the immunogen. In one preferred but non-limiting example, the binding domain includes a VWA domain of capillary morphogenesis protein 2 (CMG-2, also known as ANTRX2) and the heterologous immunogen is derived from an anthrax toxin (e.g., part or all of anthrax PA).

The heterologous immunogen that is used to decorate the VLP can be derived from more than one immunogen or more than one immunogenic domain. For example, the immunogen can include a first domain that is bound by the binding domain, and a second domain that is heterologous to the first domain. The first and second domains can be recombinantly fused and expressed as a fusion protein. For example, the binding domain can be derived from a VWA domain of CMG-2, while the first domain of the heterologous immunogen is derived from a part of anthrax PA that is recognized (bound) by the VWA domain of CMG-2. The second domain of the heterologous immunogen is optionally derived from another vaccine target of interest, e.g., a toxin protein other than PA, such as a ricin toxin or a botulinum toxin. Furthermore, compositions of the invention can include multivalent vaccine compositions that include two or more different second domains, whether displayed on a single VLP, or multiple VLPs in a single injection formulation.

Thus, the invention also includes an immunogenic composition that includes a viral nanoparticle derived from a nodavirus that also includes a heterologous immunogen binding domain. In this aspect, the viral nanoparticle is decorated with at least one immunogen, the immunogen including a first domain that is bound by the heterologous immunogen binding domain, and a second domain that is heterologous to the first domain. For example, the viral nanoparticle can be derived from flock house virus and the heterologous binding domain can include a VWA domain of capillary morphogenesis protein 2. The first domain of the at least one immunogen can include a portion of a PA domain of an anthrax toxin that is bound by the VWA domain, while the second domain can be derived from a toxin protein such as a ricin toxin or botulinum toxin.

Optionally, the immunogenic composition can be multivalent. For example, the viral nanoparticle can be decorated with at least two different immunogens. Thus, in one illustrative example, the two different immunogens each have a first domain and a second domain, with the first domain being the same for each of the at least two immunogens. The second domain is different for each of the immunogens, and the first domain is heterologous to the second domain.

Alternately or additionally, the composition can provide a multivalent immunogen by providing different nanoparticles. For example, the composition can include a second viral nanoparticle that is different from the first viral nanoparticle, e.g., where the second viral particle is derived from a nodavirus and includes a second heterologous immunogen binding domain. The second viral nanoparticle is optionally decorated with at least one second immunogen that includes a first domain that is bound by the second heterologous immunogen binding domain. The second domain of the second immunogen is heterologous to the first domain. In one example, the second heterologous immunogen binding domain and the first heterologous immunogen binding domain are the same, the first domain of the first immunogen and the first domain of the second immunogen are the same, and the second domain of the first immunogen and the second domain of the second immunogen are different, thereby providing a multivalent immunogenic composition. For example, the first and second immunogen binding domains can be derived from a VWA domain of capillary morphogenesis protein 2, while the first domain of the first and second immunogens are derived from anthrax PA. The second domain of the first and second immunogens are independently selected from, e.g., a toxin other than an anthrax toxin, a ricin toxin and a botulinum toxin.

In any of the embodiments herein, steric crowding can limit the number of heterologous immunogens that decorate the VLP. For example, when the VLP is decorated with bound anthrax PA, the VLP typically includes 180 binding domains coupled to up to a maximum of about 120 heterologous immunogens.

Accordingly, the invention provides an immunogenic composition that includes a nodavirus-derived VLP such as an FHV having a heterologous immunogen derived from an anthrax toxin such as anthrax PA.

In a related aspect, the invention provides a method of antitoxin therapy to treat a toxin in a patient. The method includes identifying a patient in need of antitoxin therapy; and administering to the patient an antitoxin that comprises a nodavirus-derived virus like particle (VLP) that comprises a heterologous toxin binding domain. The binding domain binds the toxin in the patient, thereby acting as an antitoxin.

A variety of applications are provided herein. The patient can be a human patient or a veterinary patient. In one aspect, the patient is infected with anthrax and the binding domain binds to a component of an anthrax toxin. All of the features noted above with respect to antitoxin compositions are applicable here as well e.g., the VLP can be derived from FHV or another nodavirus, the binding domain can include a heterologous VWA domain of a ANTRX2 protein, bound by a PA domain of the anthrax toxin, etc.

Administration can be, e.g., by i.v. or i.p. administration of the VLP to the patient, or any other administration method that brings the antitoxin into contact with toxin in the patient. The VLP typically binds the toxin in a dose-dependent manner and the method can include selecting a dosage regimen for administration of the VLP that is capable of ameiliorating the effect of the toxin in the patient.

In a similar aspect, a method of vaccinating a patient with an immunogen decorated nodavirus derived VLP is provided. The method includes binding an immunogen to an immunogen binding site displayed on the VLP; and administering the resulting immunogen decorated VLP to a patient, thereby vaccinating the patient against the immunogen.

As with the preceding methods, the patient can be a human or veterinary patient Administration to the patient can be done via injection, e.g., s.c. or i.m. injection.

The features described for vaccine compositions are applicable to this embodiment as well. For example, the immunogen can be derived from an anthrax PA, the VLP can be derived from Flock House Virus or another nodavirus and the heterologous immunogen binding site can include a VWA domain of an ANTXR2 protein, etc.

Thus, in one embodiment, a method of vaccinating a patient against anthrax infection is provided. The method includes providing a composition comprising a nodavirus-derived VLP that comprises or is decorated with an anthrax derived immunogen; and, administering the composition to a patient, thereby vaccinating the patient against the anthrax-derived immunogen.

General methods of vaccinating a patient against infection are also a feature of the invention. The methods include, e.g., providing a composition comprising a nodavirus-derived VLP that comprises an immunogen binding site recombinantly expressed as part of the VLP, wherein the binding site is bound, in the composition, to an immunogen, where the immunogen comprises a first domain that is bound by the binding domain and a second domain that is heterologous to the first domain. The composition is administered to a patient, thereby vaccinating the patient against the immunogen.

Any of the features noted herein with respect to the relevant compositions of the invention are applicable to these method embodiments as well. Thus, for example, the toxin binding moiety can bind to anthrax PA, where the first domain is derived from an anthrax PA, while the second domain is derived from, e.g., ricin toxin or botulinum A toxin. Further any of the features noted in respect to multivalent immunogenic compositions are applicable to this method as well, e.g., where the VLP comprises a plurality of toxin binding moieties, and the composition comprises a plurality of different immunogens bound to the plurality of toxin binding moieties. Multiple VLPs can also be administered to provide multivalent protection, e.g., where the VLPs comprise different immunogens. Medicaments formulated for treatment by the methods herein are a feature of the invention.

BRIEF DESCRIPTION OF THE FIGURES

FIG. 2 provides a dose-response curve showing cell viability as a function of antitoxin concentration.

Figure 4:
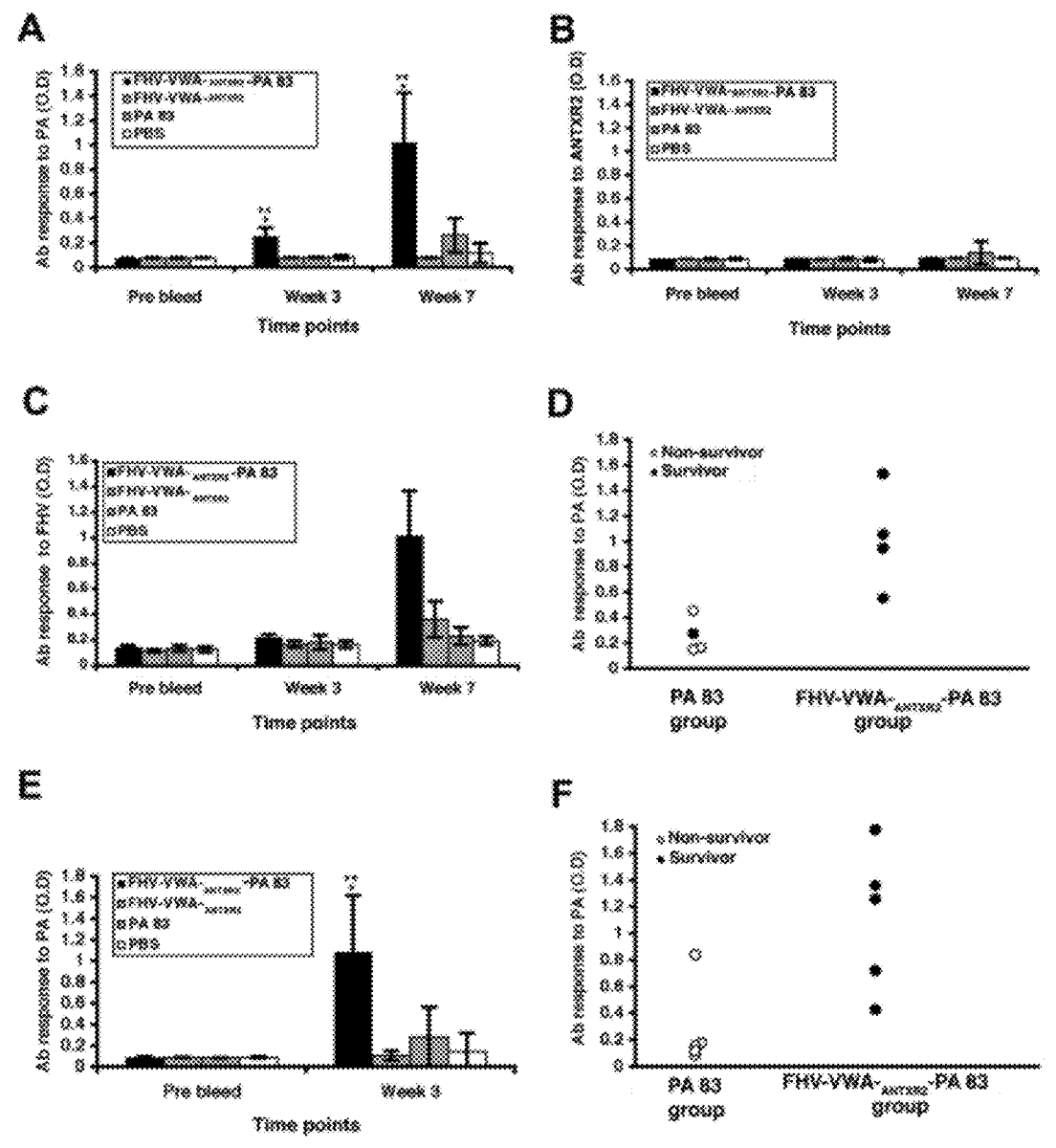

FIG. 4A-F provide histograms showing results of antibody and lethal toxin challenge responses for immunized rats.

FIG. 9 shows a schematic drawing of a way to modify a VNI (VLP) platform to present multiple immunogens to the immune system. As shown, the strategy fuses PA with antigenic portions of, e.g., ricin or botulinum toxins (e.g. PA-R and PA-B, respectively). These fusion proteins can be multivalently arrayed on the surface of VNIs to generate combination vaccines.

FIG. 10 schematically depicts a computational model of VNI-PA, VNI-PA-R, and VNI-PA-B. Domain 1 of PA (light purple in VNI-PA) is replaced with ricin (red) and botulinum neurotoxin A (blue) protein domains, respectively, to form VNI-PA-R or VNI-PA-B. Construction of the PA fusion proteins is described in Example 2.

DETAILED DISCUSSION OF THE INVENTION

Figure 1:
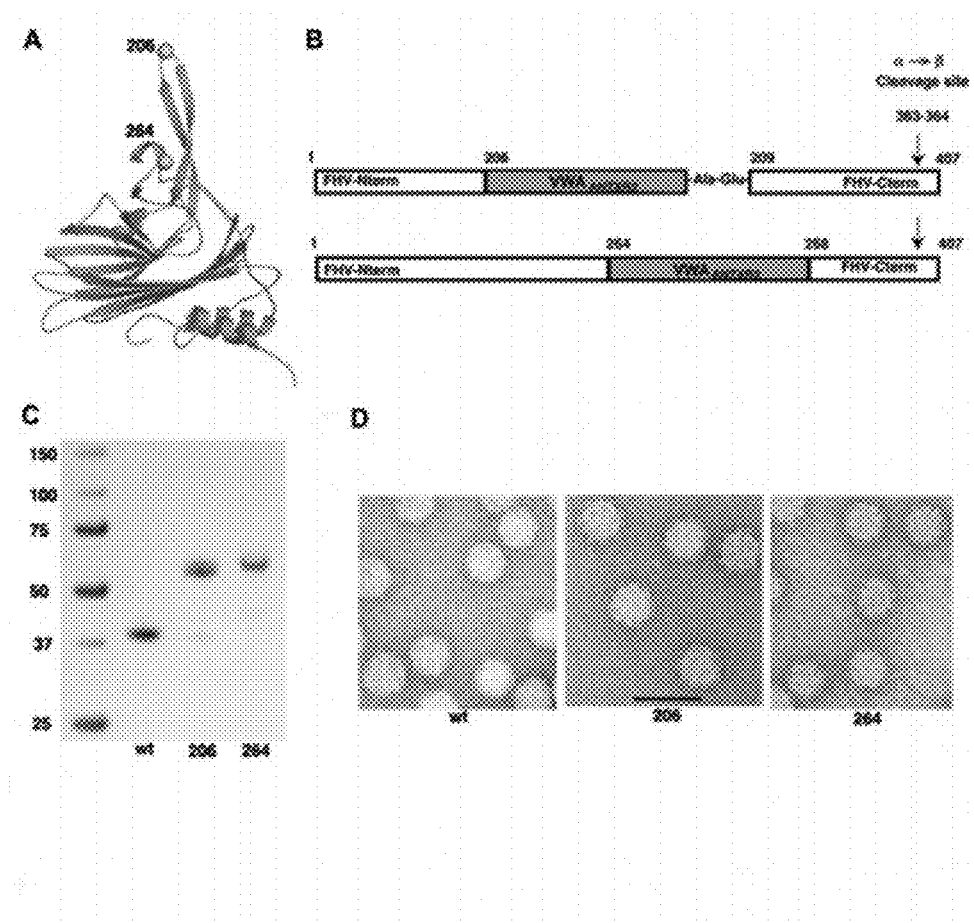
FIG. 1 Panels A-D. (a) Ribbon diagram of a single FHV coat protein subunit showing the surface-exposed loops into which the VWA domain of ANTXR2 was inserted. (b) Schematic diagram showing structure of FHV-VWA$_{ANTXR}$2 chimeric proteins 206 (top) and 264 (bottom). (c) Electrophoretic analysis of purified VLPs on a 10% Bis-Tris gel stained with Simply Blue (Invitrogen). (d) Electron micrographs of gradient-purified wt and chimeric VLPs negatively stained with uranyl acetate.

The invention provides nodavirus VLPs that comprise antitoxin activity, and that can also be decorated with an immunogen of interest to boost an immune response to the immunogen, e.g., in vaccine applications. The VLPs provide a robust platform for the presentation of essentially any immunogen of interest, by including an immunogen binding domain in the VLP and decorating the resulting recombinant VLP with a corresponding immunogen that is bound by the binding domain. The corresponding immunogen can be the immunogen of interest, or the corresponding immunogen can itself be a recombinant fusion of two or more moieties, e.g., an anchoring domain that is bound by the recombinant VLP and an additional domain that includes an immunogen target of interest. Multivalent immunogenic compositions are also contemplated, in which one or more VLP(s) in a vaccine composition is/are decorated with a plurality of different immunogens. The immunogens can include different domains of interest, e.g., in conjunction with a common anchoring domain that is bound by the recombinant VLPs. These domains of interest can include, e.g., toxin proteins such as anthrax toxin, ricin toxin, botulinum toxin, or essentially any other immunogen of interest.

In one specific example, a VLP of the T=3 insect nodavirus Flock House virus (FHV) was produced that displays 180 copies of the von Willebrand A (VWA)-domain of capillary morphogenesis protein-2 (CMG-2) (also known as ANTRX2 protein) on the surface of the VLP. ANTRX2 is a receptor for anthrax toxin and the VWA-domain represents the binding site for protective antigen (PA). In this illustrative example, we replaced amino acids 265-267 of the FHV coat protein with 181 amino acids representing residues 38-218 of ANTRX2. These sites (in FHV or other similar nodaviruses) can be used for the insertion of other antitoxin/immunogen binding domains of interest.

The modified coat protein was expressed in *Spodoptera frugiperda* cells and *Trichoplusia ni* cells using a recombinant baculovirus vector. The protein spontaneously assembled into VLPs that packaged random RNA. Electron cryomicroscopy and three dimensional image reconstruction of purified VLPs confirmed that the VWA domains are displayed on the surface of the VLPs. Computational modeling suggested that approximately 120 monomers of anthrax PA can bind to each particle. Steric crowding in this particular application prevents occupation of all 180 VWA domains.

Purified VWA VLPs functioned as a potent antitoxin in cell culture and protected rats from lethal anthrax toxin challenge. In addition, VLPs decorated with PA induced a robust antibody response against PA in rats, even in the absence of adjuvant. The response was significantly stronger than that induced against monomeric PA in control rats. Rats vaccinated with VLP-PA complexes were completely protected from intravenous challenge with anthrax lethal toxin whereas control rats that were vaccinated with monomeric PA did not survive.

FHV (or other nodavirus) VLPs displaying the VWA-domain of ANTRX2 show anthrax antitoxin activity in vivo and may therefore be useful as an effective therapeutic for the treatment of infected individuals that do not respond to antibiotic treatment (or as an adjunct to antibiotic treatment).

Further, in the case of anthrax, there are no antitoxins previously available for use in treatment. The ease of synthesis and purification of VLPs as described herein, the in vitro and in vivo stability and the multivalent display of the VWA domain represent advantages even relative to the potential use of soluble ANTRX2 as an antitoxin.

Additionally, FHV-VWA VLPs decorated with PA serve as an excellent immunogen to raise a potent antibody response to PA. This response is superior to monomeric rPA that is currently in commercial development as an anthrax vaccine. The use of VLPs decorated with PA reduces the number of immunizations required to achieve protection, which is a concern with the current rPA vaccine. Thus, such complexes serve as a novel and highly effective anthrax vaccine. Similar uses of VLPs to display other immunogens of interest should also result in a potent immune response; thus, the present invention, as well as providing an effective anthrax vaccine, also provides a general platform for vaccine development and production. As noted, for convenience, the immunogens of interest that are used to decorate the VLP can include a common anchoring domain that is bound by the VLP, in conjunction with essentially any immunogen of interest.

FHV-VWA VLPs decorated with PA can be used as a vaccine against anthrax. The polyvalent display of PA in the context of the virus particle leads to induction of a very strong antibody response; even in the absence of adjuvant; when compared to monomeric PA. In addition, the immunogen is molecularly well-defined and characterized, in contrast to the anthrax vaccine that is currently in use. Another advantage pertains to the fact that subjects are protected from lethal toxin challenge after only two injections with immunogen. This is a significant improvement compared to the lengthy immunization schedule with the currently available vaccine. Finally, using PA complexed to ANTRX2 as an antigen can lead to induction of antibodies that crosslink PA to ANTRX2. Such antibodies may be particularly useful in conferring protection against anthrax infection. The PA-ANTRX2 interaction also inhibits PA from binding to cells in vivo, thus minimizing the possibility that during postexposure immunization, a PA immunogen could participate in intoxication.

Similar effects for VLPs that are decorated with one or more additional immunogens are expected; accordingly, the invention provides a universal platform for vaccine development and production.

Making VLP Antitoxins

One aspect of the invention relates to the use of nodavirus-derived VLPs that include heterologous molecular decoy moieties that bind to toxins. The resulting VLPs are antitoxins against the toxin, e.g., in a human or veterinary patient, reducing a toxic effect of the toxin. In one preferred embodiment, coat protein of the nodavirus Flock House Virus (FHV) is used for the multivalent display of the Von Willebrand A (VWA) domain of capillary morphogenesis protein 2 (CMG-2; also known as ANTRX2), a primary receptor for anthrax toxin. Sites for the insertion of the VWA domain in the coat protein were selected based on analysis of the high-resolution crystal structure of FHV. The resulting chimeric virus-like-particles (VLPs) can be generated in a baculovirus system and have been shown to protect both cultured cells and live animals from toxic effects of anthrax protective antigen (PA) and lethal factor (anthrax toxin), indicating that the chimeric VWA domain binds PA, acting as a molecular decoy for anthrax toxin.

Nodavirus Derived VLPs

Nodaviruses such as FHV are non-enveloped, icosahedral (T=3) insect viruses of the family nodaviridae (Johnson et al. (1994) "Comparative studies of T=3 and T=4 icosahedral RNA insect viruses," *Arch Virol Suppl.* 9:497-512). For an introduction to nodaviruses, see Schneemann et al. (1998) "The structure and function of nodavirus particles: a paradigm for understanding chemical biology." in *Advances in virus research*, Vol. 50 (eds. Maramorsch, K., Murphy, F. A. & Shatkin, A. J.) 381-446 (Academic Press, San Diego). Nodaviruses have been described in insects and fish, and are the etiological agent of significant diseases such as Viral Nervous Necrosis (VNN), also known as fish encephalitis (Samuelsen et al. (2006) "Viral and bacterial diseases of Atlantic cod *Gadus morhua*, their prophylaxis and treatment: a review," *Dis Aquat Organ.* 71(3):239-54). The Nodaviridae have bipartite RNA genomes comprising two separate single-stranded RNA molecules, designated RNA1 and RNA2. In the natural viral life cycle, RNA1 and RNA2 are both packaged within the same virion. RNA1 encodes an RNA replicase, and RNA2 encodes a capsid protein. In one representative example, Flock House Virus (FHV), RNA1 is 3.1 kb long and RNA2 is 1.4 kb.

Accordingly, flock house virus (FHV) is a bipartite, positive-strand RNA insect nodavirus that encapsidates its two genomic RNAs (RNA1 and RNA2) in a single virion in a manner similar to other nodaviruses, such as Black Beetle virus (BBV), Boolarra virus (BoV), Gypsy moth virus (GMV), and Manawatu virus (MwV). FHV provides one preferred nodavirus for modification according to the invention, although one of skill is able to use other nodaviruses in a similar manner. Nodamura virus is another useful example (see also, Am. J. Epidemiol. 86(2), 271-285) as is Pariacoto virus (see also, *J. Virol.* 74(11):5123-5132).

The FHV capsid is composed of 180 subunits of a single type of coat protein, and the icosahedral, solid shell capsid encapsidates a bipartite, single-stranded RNA genome. The crystal structure of FHV particles shows that the coat protein contains, several surface-exposed loops that can be targeted for insertion of foreign proteins and peptides. See Fisher & Johnson "Ordered duplex RNA controls capsid architecture in an icosahedral animal virus." *Nature* 361, 176-179; Thiery et al. NODAVIRUS-VLP IMMUNIZATION COMPOSITION WO 2005/112994 A1; Hall RECOMBINANT NODAVIRUS COMPOSITIONS AND METHODS U.S. Pat. No. 6,171,591; Ahlquist et al. (1994) "Protein-protein interactions and glycerophospholipids in bromovirus and nodavirus RNA replication" *Arch Virol Suppl.* 9:135-45. In general, the expression of nodavirus capsid proteins in cell culture, e.g., bacterial or insect cells, can produce mature virus like particles (VLPs), e.g., using a recombinant expression system that expresses the open reading frame of the RNA2 gene (e.g., in a baculovirus expression system). See, e.g., Oliveira et al. (2000) "Virus Maturation Targets the Protein Capsid to Concerted Disassembly and Unfolding," *J. Biol. Chem.* 275(21):16037-16043. Several examples of expression systems that make VLPs using expression systems that express Nodavirus capsid proteins are available and can be adapted to the present invention. An example of a betanodavirus expression system other than FHV that generates VLPs is available for the Dragon grouper, *Epinephelus lanceolatus*, nervous necrosis virus (DGNNV); see, e.g., Lu and Lin (2003) "Involvement of the terminus of grouper betanodavirus capsid protein in virus-like particle assembly" *Archives of Virology* 148(2): 0304-8608.

Making Recombinant VLPs

The coat protein of a nodavirus such as FHV can be recombinantly engineered to include essentially any polypeptide of interest. The crystal structure of FHV has been determined, and other nodaviruses can be deduced by comparison to solved FHV structures or general crystallographic or other available virus structure determination methods. Nodaviruses such as FHV have surface loop domains into which a polypeptide of interest can be inserted for VLP display. As discussed in detail in the examples herein, preferred sites for insertion include two surface-exposed loops at approximately amino acid positions that correspond to 206 and 264 of FHV. In the examples herein, these sites are shown to accommodate a 181 amino acid ANTXR2 VWA domain without disrupting coat protein assembly into virus-like particles (VLPs) (FIG. 1*a*). In FHV-$VWA_{ANTXR2}$ chimera 206, the VWA domain and a C-terminal two amino acid linker (Ala-Glu) replaced FHV coat protein residues 207-208 (FIG. 1*b*). In FHV-$VWA_{ANTXR2}$ chimera 264, the VWA domain replaced FHV residues 265-267. General regions that can be manipulated for insertion include Loop L1 (corresponding to amino acids 195-219 (including, e.g., 201-213) of FHV coat protein), Loop L2 (corresponding to amino acids 263-277 of FHV coat protein), Loop L3 (corresponding to amino acids including e.g., 124-142 of FHV coat protein), Loop I1 (corresponding to amino acids 107-110 of FHV coat protein), Loop I2 (corresponding to amino acids 152-165 of FHV coat protein), and Loop I3 (corresponding to amino acids 304-310 of FHV coat protein).

Insertions or deletions of heterologous proteins of interest at these sites can be engineered into cDNAs corresponding to the RNA2 gene of the relevant nodavirus, e.g., in a baculovirus expression system for expression in insect cells such as *Trichoplusia ni* cells or *Spodoptera Frugiperda* (e.g., IPLB-Sf21) cells.

cDNAs corresponding to an RNA2 nodavirus gene are engineered by standard cloning, mutagenesis or PCR based methods. Details regarding such procedures are found in standard references, e.g., general texts that describe molecular biological techniques for the cloning and manipulation of nucleic acids and production of encoded polypeptides. These include Sambrook et al., *Molecular Cloning—A Laboratory Manual* (3*rd Ed*.), *Vol.* 1-3, Cold Spring Harbor Laboratory, Cold Spring Harbor, N.Y., 2001 ("Sambrook") and *Current Protocols in Molecular Biology*, F. M. Ausubel et al., eds., *Current Protocols*, a joint venture between Greene Publishing Associates, Inc. and John Wiley & Sons, Inc., (supplemented through the current date) ("Ausubel") and Berger and Kimmel, *Guide to Molecular Cloning Techniques, Methods in Enzymology volume* 152 Academic Press, Inc., San Diego, Calif. (Berger)). These texts describe mutagenesis, the use of expression vectors, promoters and many other relevant topics related to e.g., the generation of clones that comprise nucleic acids of interest.

The present invention also relates to the production of transgenic organisms, which may be, e.g., bacteria, yeast, fungi, animal or plant cells (or even whole organisms), transduced with the nucleic acids of the invention (e.g., nucleic acids encoding nodavirus capsid proteins that include heterologous sequences, as noted herein). A thorough discussion of techniques relevant to bacteria, unicellular eukaryotes and cell culture generally is found in references enumerated herein and are briefly outlined as follows. Several well-known methods of introducing target nucleic acids into bacterial cells are available, any of which may be used in the present invention. These include: fusion of the recipient cells with bacterial protoplasts containing the DNA, treatment of the cells with liposomes containing the DNA, electroporation, projectile bombardment (biolistics), carbon fiber delivery, and infection with viral vectors (discussed further, below), etc. Bacterial or, e.g., insect cells can be used to amplify the number of plasmids containing DNA constructs of this invention. The cells are grown to log phase and the plasmids within the cells can be isolated by a variety of methods known in the art (see, for instance, Sambrook). In addition, a plethora of kits are commercially available for the purification of plasmids from bacteria. For their proper use, follow the manufacturer's instructions (see, for example, EasyPrep™, FlexiPrep™, both from Pharmacia Biotech; StrataClean™ from Stratagene; and, QJAprep™ from Qiagen). The isolated and purified plasmids are then further manipulated to produce other plasmids, used to transfect other cells or incorporated into organism specific vectors to infect cells of interest. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are typically suitable for replication and integration in prokaryotes, eukaryotes, or both. See, Giliman & Smith (1979) *Gene* 8:81; Roberts et al. (1987) *Nature* 328:731; Schneider et al. (1995) *Protein Expr. Purif.* 6435:10; Ausubel, Sambrook, Berger (all infra). A catalogue of Bacteria and Bacteriophages useful for cloning is provided, e.g., by the ATCC, e.g., *The ATCC Catalogue of Bacteria and Bacteriophage* (1992) Gherna et al. (eds) published by the ATCC. Additional basic procedures for sequencing, cloning and other aspects of molecular biology and underlying theoretical considerations are also found in Watson et al. (1992) *Recombinant DNA*, Second Edition, Scientific American Books, NY. In addition, essentially any nucleic acid can be custom or standard ordered from any of a variety of commercial sources; such as the Midland Certified Reagent Company (Midland, Tex.), The Great American Gene Company (Ramona, Calif.), ExpressGen Inc. (Chicago, Ill.), Operon Technologies Inc. (Alameda, Calif.) and many others.

Cell culture media appropriate for growing cells that comprise VLPs in general are set forth in the previous references and additionally, in Atlas and Parks (eds) *The Handbook of Microbiological Media* (1993) CRC Press, Boca Raton, Fla. Additional information for cell culture is found in available commercial literature such as the *Life Science Research Cell Culture Catalogue* (1998) from Sigma-Aldrich, Inc (St Louis, Mo.) ("Sigma-LSRCCC") and e.g., *the Plant Culture Catalogue* and supplement (e.g., 1997 or later) also from Sigma-Aldrich, Inc (St Louis, Mo.) ("Sigma-PCCS"). The culture of animal cells is described, e.g., by Freshney (2000) *Culture of Animal Cells: A Manual Of Basic Techniques* John Wiley and Sons, NY. Preferred cell culture media for insect cell culture (particularly applicable to baculovirus expression, discussed in more detail below) is available from Expression Systems, Inc. (Davis, Calif.).

In addition to other references noted herein, a variety of purification/protein purification methods are well known in the art and can be applied to VLP purification, including, e.g., those set forth in R. Scopes, *Protein Purification*, Springer-Verlag, N.Y. (1982); Deutscher, *Methods in Enzymology Vol.* 182*: Guide to Protein Purification*, Academic Press, Inc. N.Y. (1990); Sandana (1997) *Bioseparation of Proteins*, Academic Press, Inc.; Bollag et al. (1996) *Protein Methods,* 2nd Edition Wiley-Liss, NY; Walker (1996) *The Protein Protocols Handbook* Humana Press, NJ; Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice* 3rd Edition Springer Verlag, NY; Janson and Ryden (1998) *Protein Purification: Principles, High Resolution Methods and Applications, Second Edition* Wiley-VCH, NY; and Walker (1998) *Protein Protocols on CD-ROM* Humana Press, NJ; and the references cited therein. Preferred methods of VLP purification include sucrose density purification, e.g., as described in the examples herein.

Further Details Regarding Baculovirus and Other Insect Cell Expression Systems

In one convenient aspect, recombinant nodavirus capsid protein can be expressed to produce VLPs in cells using a baculovirus expression system. The Baculoviridae infect many species of insects. Bacculoviridae have strong promoters and a well-characterized genome that make them suitable as expression vectors in insect cells. For example, the most common invertebrate expression vector system is based on the *Autographa Californica* nuclear polyhedrosis virus (AcNPV), an insect baculovirus isolated from the Alfalfa looper. This virus replicates in the nucleus of many different lepidopteran insect cell lines. The baculovirus expression vector system is commonly used to express genes derived from other viruses (e.g., as in the present invention), as well as from fungi, bacteria, plants, and animals. In this system, foreign genes placed under the control of the strong polyhedrin promoter of the AcNPV are expressed at high levels in cultured lepidopteran (and many other) insect cells. In addition, Baculovirus have shown the ability to be used as vectors for a variety of mammalian cell lines. The most widely used lepidopteran cells for Baculovirus expression systems are the Sf9 and Sf21 cell lines isolated from ovarian tissue of the fall army worm, *Spodoptera frugiperda*, and the High Five cell line, designated BTITn-5B1-4, originally established from *Trichoplusia ni* embryonic tissue. A variety of additional details regarding Baculovirus expression systems can be found on the internet at bacculovirus(dot)com and at expressionsystems(dot)com, and in *Baculovirus Expression Protocols* (Methods in Molecular Biology, Vol 39) Christopher D. Richardson (Editor); (1998) Humana Pr; ISBN: 0896032728; O'Reilly et al., *Baculovirus Expression Vectors A Laboratory Manual*, 1994 Oxford University Press, and *The Baculovirus Expression System: A Laboratory Guide* by Linda A. King, R. D. Possee; (1992) Chapman & Hall; ISBN: 0412371502; and the references cited therein.

As applied to the present invention, FHV-like particles can be generated by expressing FHV coat protein/heterologous domain chimeric genes in a baculovirus expression system. For a description of baculovirus expression of nodavirus proteins, See, for example, Schneemann et al. (1993) "Use of recombinant baculoviruses in synthesis of morphologically distinct virus-like particles of flock house virus, a nodavirus." *J. Virol*. 67, 2756-2763; O'Reilly et al. (1992) *Baculovirus Expression Vectors: A Laboratory Manual*. W. H. Freemnan and Co., New York; Vlak and Keus (1990) In *Viral Vaccines*. Wiley-Liss, Inc., New York. pp. 91-128; and Gallagher & Rueckert (1988)"Assembly-dependent maturation cleavage in provirions of a small icosahedral insect ribovirus." *J. Virol*. 62, 3399-3406. This allows for the large-scale production of chimeric particles that form into VLPs. For example, *Trichoplusia ni* or *Spodoptera Frugiperda* (e.g., IPLB-Sf21, or SF9) cells can be propagated and infected, e.g., as described by Dong et al. (1998) "Particle polymorphism caused by deletion of a peptide molecular switch in a quasi-equivalent virus" *J. Virol*. 72, 6024-6033 (1998). Other suitable cell lines include *Manduca* cell lines (e.g., *Manduca Sexta* cell lines), *Estigmene* cell lines (e.g., *Estigmene acrea* cell lines), Monarch butterfly cell lines, *Mamestra* cell lines (e.g., *Mamestra brassicae* cell lines), *Dipteran* cell lines, *Drosophila* insect cell line Schneider 2 (S2), and cell line Kc1.

Accordingly, a variety of proteins have been produced by standard baculovirus expression vector system, and VLPs of the invention can be made by such protocols. Technologies utilizing stable transfected insect cells are also useful and are also desirably used in the present invention for VLP production. See, e.g., Pfeifer (1998) "Expression of heterologous proteins in stable insect cell culture" *Curr Opin Biotechnol*. 9:518-21; Farrell et al. (1998) "High-level expression of secreted glycoproteins in transformed lepidopteran insect cells using a novel expression vector." *Biotechnol Bioeng* 60(6): 656-63; Lubiniecki, *Cytotechnology* (1998) 28:139-145; Murphy, et al., *Curr. Prot. Mol. Biol*. (1997) 16.9.1-16.9.10; McCarrol et al., *Curr. Op. Biotech*. (1997) 8:590-594, Hegedus et al., *Gene* (1998) 207:241-249; Pfeifer et al. (1997) "Baculovirus immediate-early promoter-mediated expression of the Zeocin resistance gene for use as a dominant selectable marker in dipteran and lepidopteran insect cell lines." *Gene*. 188:183-90; McLachlin and Miller (1997) "Stable transformation of insect cells to coexpress a rapidly selectable marker gene and an inhibitor of apoptosis" *In Vitro Cell Dev Biol Anim*. 33:575-9; McCarroll and King (1997) "Stable insect cell cultures for recombinant protein production" *Curr Opin Biotechnol*. 8:590-4; Vaughn, et al., (1997) *In Vitro Cell Dev*. Biol. 33:479-482; Jarvis et al. (1996)"Immediate-early baculovirus vectors for foreign gene expression in transformed or infected insect cells" *Protein Expr Purif*. 8:191-203; Schlaeger, (1996) *Cytotechnology* 20:57-70; and Eaton, *J. Chrom. A* (1995) 705:105-114; Davies, *Curr. Op. Biotech*. (1995) 6:543-547, Potter, et al., *Env. Health Pers*. (1995) 103:7-8, Poul, et al. *Eur. J. Imm*. (1995) 25:2005-2009; Bernard et al., *Cytotechnology* (1994) 15(1-3):139-144; Jarvis et al. (1995) "Continuous foreign gene expression in transformed lepidopteran insect cells." *Methods Mol. Biol*. 39:187-202; Lower, *Cytotechnology* (1995) 18:15-20; Hink et al., *Biotech. Prog*. (1991) 7:9-14; Jarvis et al. (1990)"Use of early baculovirus promoters for continuous expression and efficient processing of foreign gene products in stably transformed lepidopteran cells." *Biotechnology* 8:950-5; and Duane, et al., *J. Tiss. Cult. Meth*. (1989) 12(1):13-16.

VLPs that Include Heterologous Domains

As discussed above, one feature of the invention is the insertion of heterologous coding sequences into the RNA2 gene of a nodavirus at sites that do not interfere with capsid assembly. For example, in FHV, relevant sites for insertion of heterologous sequences include amino acid residues 207-208 and 265-267 of the FHV coat protein.

The choice of which heterologous sequence to incorporate into the coat protein depends on the application. In general, recombinant VLPs that comprise heterologous polypeptide sequences can be used either as a molecular decoy (antitoxin) or as a vaccine platform for binding and presenting an immunogen.

When used as a molecular decoy, the VLP can include any of a variety of anti-toxin moieties. For example, when the primary manifestations of a disease are caused by a microbial toxin, a corresponding antitoxin, if administered in time can have a pronounced prophylactic or curative effect. Common bacterial toxins include botulisim toxin, diphtheria toxin, anthrax toxin, tetanus toxin and many others. Anti-toxin components that can be incorporated into the VLPs of the invention bind these toxins in a patient, preventing their usual mode of action in the patient. For example, as detailed in the examples herein, two anthrax toxin receptors, widely distributed on human cells, have been identified: anthrax toxin receptor/tumor endothelial marker 8 (ANTXR1)[7] and capillary morphogenesis gene 2 (ANTXR2)[8]. Although both receptors bind anthrax PA through a 200 amino acid extracellular von Willebrand factor A (VWA) domain, the VWA domain of ANTXR2 has a 1000-fold higher binding affinity for PA than the VWA domain of ANTXR1. Thus, VLPs comprising many copies (for FHV, 180 copies, or one per capsid protein of the VLP), of the VWA domain of ANTXR2 acts as a potent anthrax antitoxin.

While this example serves to illustrate the invention, the example is not limiting. The specific interactions between a variety of toxins and host receptors are known and can similarly be used to select appropriate anti-toxin moieties for incorporation into VLPs. The major symptoms associated, e.g., with disease caused by *Corynebacterium diphtheriae* (diphtheria), *Bordetella pertussis* (whooping cough), *Vibrio cholerae* (cholera), *Bacillus anthracis* (anthrax), *Clostridium botulinum* (botulism), *Clostridium tetani* (tetanus), and enterohemorrhagic *Escherichia coli* (bloody diarrhea and hemolytic uremic syndrome) are toxin mediated, and the toxins and modes of action for these diseases are all known (for additional examples, see, e.g., drlera(dot)com/bacterial_diseases/protein_toxins(dot)htm#table on the world wide web). For example, diptheria toxin binds to the heparin-binding epidermal growth factor HB-EGF receptor on susceptible cells and enters by receptor-mediated endocytosis (see textbookofbacteriology(dot)net/diphtheria(dot)html). By incorporating the ditheria toxin binding site of the HB-EGF receptor into a VLP of the invention, e.g., at the sites noted in the examples herein relating to anthrax applications, an antitoxin against diptheria toxin is provided. Similarly, botulisim toxin (botulinum toxin) binds irreversibly to receptors on unmyelinated presynaptic membranes. This binding is mediated by a Carboxy (C) terminal of botulinum toxin heavy chain (in its native state, this heavy chain is associated with a light chain). Gangliosides with more than one neuraminic (sialic) acid, e.g. GT1b bind to the toxin. By incorporating glycoprotein components that comprise gangliosides into the VLP, a botulinium antitoxin is produced. Such glycoproteins have been produced, see e.g., Hashimoto et al. (1998) "A Streptavidin-Based Neoglycoprotein Carrying More Than 140 GT1b Oligosaccharides: Quantitative Estimation of the Binding Specificity of Murine Sialoadhesin Expressed on CHO Cells" *J. Biochem*, 123(3): 468-478.

Decorating VLPs with Bound Heterologous Immunogens to Produce Vaccines

Binding Heterologous Immunogens to Heterologous Domains on VLPs

Heterologous polypeptide domains can be recombinantly fused with the capsid protein of the relevant VLP e.g., as an in frame fusion domain, or as a chemically coupled domain to such a fusion to permit binding of one or more immunogen to the VLP. The resulting immunogen decorated VLPs can be used as vaccines against the relevant immunogen. As described in the examples herein, the heterologous domain can be one that binds to the relevant immunogen directly, e.g., the VWA domain of ANTXR2, which binds Anthrax PA.

However, any high affinity interaction between a polypeptide domain and a binding partner can be utilized, e.g., by recombinantly or chemically coupling the binding partner (as an "adaptor" or "linker") to the immunogen, and then binding the resulting immunogen fusion to a VLP that binds the immunogen fusion. A large number of such cognate binding partners are known in the art and can be adapted to the practice of the present invention by being incorporated as VLP domains/immunogen fusion elements. For examples of co-binding partners, see, e.g.: Nilsson et al. (1997) "Affinity fusion strategies for detection, purification, and immobilization of recombinant proteins" Protein Expression and Purification 11: 1-16; and Terpe et al. (2003) "Overview of tag protein fusions: From molecular and biochemical fundamentals to commercial systems" Applied Microbiology and Biotechnology 60:523-533, and references therein). Tags that can be used to couple the VLP to the immunogen include, but are not limited to, a polyhistidine tag (e.g., a His-6, His-8, or His-10 tag) that binds divalent cations (e.g., $Ni^{2+}$), a biotin moiety (e.g., on an in vivo biotinylated polypeptide sequence of the VLP or immunogen) that binds avidin (present in the immunogen or VLP), a GST (glutathione S-transferase) sequence that binds glutathione, an S tag that binds S protein, an antigen that binds an antibody or domain or fragment thereof (including, e.g., T7, myc, FLAG, and B tags that bind corresponding antibodies), a FLASH Tag (a high affinity tag that couples to specific arsenic based moieties), a toxin receptor or receptor domain that binds to the toxin, protein A or a derivative thereof (e.g., Z) that binds IgG, maltose-binding protein (MBP) that binds amylose, an albumin-binding protein that binds albumin, a chitin binding domain that binds chitin, a calmodulin binding peptide that binds calmodulin, a cellulose binding domain that binds cellulose, etc. Another exemplary coupling partner that can be used to couple the VLP to the immunogen is a SNAP-tag. The SNAP-tag is an approximately 20 kDa version of a protein $O^6$-alkylguanine-DNA alkyltransferase which has a single reactive cysteine with a very high affinity for guanines alkylated at the $O^6$-position.

Generally speaking, the invention optionally includes the use of such universal "adaptor" or "linker" domains in the immunogen of interest to facilitate binding to a VLP. As noted, a variety of immunogens and their binding domains are known. Once a recombinant VLP is produced that includes a binding domain of interest, this becomes a useful platform for coupling one or more different immunogens to the VLP. Thus, the VLPs herein that include the VWA domain of ANTXR2, which binds Anthrax PA can be used as a general vaccine platform for the delivery of essentially any immunogen of interest. That is, an immunogen of interest is fused to the portion of PA that is bound by a VWA domain (see Example 2 herein for details). The PA adaptor/linker binds the immunogen of interest to the VLP. Such immunogens of interest include any of those noted herein, including ricin toxin and botulinum toxin.

This approach is also useful for making multivalent vaccine compositions, e.g., by binding one or more VLP to one or more immunogen through a universal adaptor/linker that recognizes the VLP. Thus, a plurality of immunogen fusions that include an adaptor domain and an immunogen domain of interest can be bound to one or more VLP and then administered as a multivalent vaccine.

In any case, a recombinant VLP that can bind the immunogen of interest can, typically, bind many copies of the immunogen. This is because the VLP can be made up of e.g., 180 copies of the capsid protein, with each copy comprising an immunogen binding sequence. The precise number of immunogens that can decorate the VLP will vary, depending on the steric properties of the immunogen. For example, the VLP will typically be able to bind 10 or more copies, generally 50 or more copies, often 100 or more copies, and sometimes up to 120 or more copies, and occasionally up to about 180 copies. In the case of anthrax PA binding to a VWA-VLP, described extensively herein, up to about 120 copies of PA can bind to the VLP.

The immunogen and the recombinant VLP can be co-expressed in a single cell, or the recombinant VLP and immunogen can be separately expressed. All references described regarding recombinant production and expression of VLPs apply equally to expression and production of the immunogens. Methods of isolating VLPs are described above. Typical biomolecule purification methods can similarly be used to isolate recombinant immunogen, which can then be used to decorate purified recombinant VLPs. For example, protein isolation methods for isolating polypeptide-based immunogens are available, e.g., those set forth in the references noted above in the context of VLP isolation.

Any of the examples above relating to VLPs comprising heterologous domains can also equally relate to decoration of the VLP. That is common bacterial toxins to be used to decorate the VLPs can include anthrax toxin, botulisim toxin, diphtheria toxin, tetanus toxin and many others. These can be coupled to the VLP either by binding to their respective antitoxin (incorporated into the VLP as noted above), or, e.g., by coupling through a standard heterologous binding partner interaction as noted herein.

The VLPs of the invention can display essentially any immunogen of interest, including immunogens that are not necessarily toxins. For example, VLPs can incorporate (or can be decorated with) relevant vaccine components related to significant vaccine targets such as bubonic plague. In this example, *Yersinia pestis* is the Gram-negative bacterium of the family Enterobacteriaceae responsible for bubonic plague (including the "black death", likely caused by *Yersinia pestis* biovar Medievalis). See, e.g., Carniel and Hinnebusch (eds.) (2004) *Yersinia: Molecular and Cellular Biology* Horizon Bioscience, Institut Pasteur, Paris, France and National Institutes of Health, Hamilton, USA; Collins F M (1996). "*Pasteurella, Yersinia,* and *Francisella.*" In: *Barron's Medical Microbiology* (Barron S et al, eds.), 4th ed. *Y. pestis* infection can also cause pneumonic and septicemic plague. See also, Ryan K J; Ray C G (editors) (2004). *Sherris Medical Microbiology,* 4th ed., McGraw Hill, pp. 484-8; Parkhill et al. "Genome sequence of *Yersinia pestis,* the causative agent of plague" *Nature* 413: 523-527. Pathogenicity of *Yersinia pestis* is mediated by two anti-phagocytic antigens, known as F1 and VW, both of which are important for virulence. Collins F M (1996), above. Immunity (natural or induced) is achieved by the production of antibodies against F1 and VW antigens; antibodies against F1 and VW induce phagocytosis by neutrophils. Salyers and Whitt (2002). *Bacterial Pathogenesis: A Molecular Approach,* 2nd ed., ASM Press. 207-12.

The F1 antigen is one preferred vaccine target. F1 is an outer membrane capsular protein of *Y. pestis*. The immunogenicity of whole F1 and of various peptide sequences, e.g, predicted to possess B (three sequences, B1, B2 and B3) and T (two sequences, T1 and T2) cell determinants have been studied, as have chimeras made between B and T structures. See, e.g., Sabhnani (2003) "Developing subunit immunogens using B and T cell epitopes and their constructs derived from the F1 antigen of *Yersinia pestis* using novel delivery vehicles." *FEMS Immunol Med Microbiol.* 38(3):215-29; Grosfeld et al. (2003) "Effective Protective Immunity to *Yersinia pestis* Infection Conferred by DNA Vaccine Coding for Derivatives of the F1 Capsular Antigen" *Infect Immun.* 71(1): 374-383. Virulent and potentially virulent cells of *Yersinia pestis* produce virulence or V and W antigens (VW(+)); these antigens are also preferred vaccine targets for VLP decoration. For example, antibodies against V protein protect against *Yersinia pestis* infection and can be used to decorate VLPs of the invention. See also, e.g., Pullen et al. (1998) "Analysis of the *Yersinia pestis* V Protein for the Presence of Linear Antibody Epitopes" *Infect Immun.* 66(2): 521-527. Vaccines that incorporate both V and F1 elements are also in development See also Elvin and Williamson (2000) "The F1 and V subunit vaccine protects against plague in the absence of IL-4 driven immune responses" *Microb. Pathog.* 29:223-230; see also Anisimov et al. (2004) "Intraspecific Diversity of *Yersinia pestis*" *Clinical Microbiology Reviews* 17(2): 434-464; Williamson (2001) "Plague vaccine research and Development" *Journal of Applied Microbiology* 91:606-608.

Accordingly, in one embodiment of the invention, VLPs are decorated with F1 and/or V protein, or subsequences thereof, using any of the approaches already noted for binding the F1 and/or V proteins or peptide subsequences thereof to the VLP. F1 and/or V proteins, or portions thereof (e.g., for F1, B1, B2, B3 and/or T1 and/or T2), can also be recombinantly incorporated into the VLPs of the invention, at one or more of the loop sites noted herein. In either case, the resulting VLPs are used as an immunogen to raise protective antibodies against F1 and/or V protein. VLPs as Anthrax Vaccines In one particularly preferred aspect, VLPs of the invention are decorated with anthrax toxin components (typically PA, or polypeptide sequences derived from PA). Multivalent display of the ANTXR2 VWA domain on the surface of the icosahedral insect nodavirus FHV VLP was shown to induce a potent immune response against LeTx when coated with PA. This immune response was neutralizing in vitro and protected animals against LeTx challenge following a single administration without adjuvant.

While the examples below refer to particular ANTRX2 receptor polypeptides and PA sequences, one of skill will recognize that the invention equally encompasses allelic variants of particular sequences. Further, the present invention is not limited to these particular examples. Recombinant VLPs can for example, include larger segments of the ANTRX2 receptor polypeptide than the VWA sequence, and can also include, e.g., purification components (e.g., VLP purification tags that include any of the binding partners noted above). In addition, conservative variations of the ANTRX2 receptor polypeptide (or VWA component thereof) can readily be substituted. Preferably, any such conservative substitutions of the VWA domain will still be bound by the relevant immunogen, e.g., a PA domain (or conservative variant thereof) will preferably bind to the relevant recombinant VLP. This can be tested for in a routine VLP-immunogen binding assay, e.g., as taught in the examples herein.

"Conservatively modified variations" or, simply, "conservative variations" of a particular nucleic acid or polypeptide are those that encode identical or essentially identical amino acid sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid.

Conservative substitution tables providing functionally similar amino acids are well known in the art. Table A sets forth six groups which contain amino acids that are "conservative substitutions" for one another.

TABLE A

Conservative Substitution Groups

| | | | |
|---|---|---|---|
| 1 | Alanine (A) | Serine (S) | Threonine (T) |
| 2 | Aspartic acid (D) | Glutamic acid (E) | |
| 3 | Asparagine (N) | Glutamine (Q) | |
| 4 | Arginine (R) | Lysine (K) | |
| 5 | Isoleucine (I) | Leucine (L) | Methionine (M) Valine (V) |
| 6 | Phenylalanine (F) | Tyrosine (Y) | Tryptophan (W) |

Thus, "conservatively substituted variations" of a given polypeptide sequence of the present invention (e.g., ANTRX2 receptor, anthrax PA, etc,) include substitutions of a small percentage, typically less than 5%, more typically less than 2% or 1%, of the amino acids of the polypeptide sequence, with a conservatively selected amino acid of the same conservative substitution group.

The addition or deletion of sequences that do not alter the encoded activity of a nucleic acid molecule, such as the addition or deletion of a non-functional sequence, is a conservative variation of the basic nucleic acid or polypeptide.

One of skill will appreciate that many conservative variations of the nucleic acid constructs that are disclosed yield a functionally identical construct. For example, owing to the degeneracy of the genetic code, "silent substitutions" (i.e., substitutions in a nucleic acid sequence that do not result in an alteration in an encoded polypeptide) are an implied feature of every nucleic acid sequence that encodes an amino acid. Similarly, "conservative amino acid substitutions," in one or a few amino acids in an amino acid sequence are substituted with different amino acids with highly similar properties, are also readily identified as being highly similar to a disclosed construct. Such conservative variations of each relevant sequence are a feature of the present invention. Further details regarding sequence variations and methods of mutagenesis are found below.

Sequence Variations

A variety of ANTRX2 polypeptides and nucleic acids are known, including those found in GenBank (see, Definitions section herein).

Accordingly, a number of polypeptides and coding nucleic acids are described herein by sequence (See, e.g., the accession information and Examples sections below). These polypeptides and coding nucleic acids can be modified, e.g., by mutation as described herein, or simply by artificial synthesis of a desired variant. Several types of example variants are described further below.

Silent Variations

Due to the degeneracy of the genetic code, any of a variety of nucleic acids sequences encoding polypeptides of the invention are optionally produced, some which can bear various levels of sequence identity to the nucleic acids or polypeptides in the Examples below. The following provides a typical codon table specifying the genetic code, found in many biology and biochemistry texts.

TABLE B

Codon Table

| Amino acids | | | Codon |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |

TABLE B-continued

Codon Table

| Amino acids | | | Codon |
|---|---|---|---|
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

The codon table shows that many amino acids are encoded by more than one codon. For example, the codons AGA, AGG, CGA, CGC, CGG, and CGU all encode the amino acid arginine. Thus, at every position in the nucleic acids of the invention where an arginine is specified by a codon, the codon can be altered to any of the corresponding codons described above without altering the encoded polypeptide. It is understood that U in an RNA sequence corresponds to T in a DNA sequence.

Such "silent variations" are one species of "conservatively modified variations", discussed above. One of skill will recognize that each codon in a nucleic acid (except ATG, which is ordinarily the only codon for methionine) can be modified by standard techniques to encode a functionally identical polypeptide. Accordingly, each silent variation of a nucleic acid which encodes a polypeptide is implicit in any described sequence. The invention, therefore, explicitly provides each and every possible variation of a nucleic acid sequence encoding a polypeptide of the invention that could be made by selecting combinations based on possible codon choices. These combinations are made in accordance with the standard triplet genetic code (e.g., as set forth in Table B, or as is commonly available in the art) as applied to the nucleic acid sequence encoding a polypeptide of the invention. All such variations of every nucleic acid herein are specifically provided and described by consideration of the sequence in combination with the genetic code. One of skill is fully able to make these silent substitutions using the methods herein.

Mutational Derivatives

The nucleic acid and protein sequences herein can be mutated by standard methods, e.g., to improve binding between the immunogen and VLP, to improve stability or half-life, or the like. Additional information on mutation formats is found in Sambrook and Ausubel, as well as in *PCR Protocols A Guide to Methods and Applications* (Innis et al. eds) Academic Press Inc. San Diego, Calif. (1990) (Innis). The following publications and references provide additional detail on mutation formats: Arnold, *Protein engineering for unusual environments, Current Opinion in Biotechnology* 4:450-455 (1993); Bass et al., *Mutant Trp repressors with new DNA-binding specificities, Science* 242:240-245 (1988); Botstein & Shortle, *Strategies and applications of in vitro mutagenesis, Science* 229:1193-1201 (1985); Carter et al.,

*Improved oligonucleotide site-directed mutagenesis using M13 vectors, Nucl. Acids Res.* 13: 4431-4443 (1985); Carter, *Site-directed mutagenesis, Biochem. J.* 237:1-7 (1986); Carter, *Improved oligonucleotide-directed mutagenesis using M13 vectors, Methods in Enzymol.* 154: 382-403 (1987); Dale et al., *Oligonucleotide-directed random mutagenesis using the phosphorothioate method, Methods Mol. Biol.* 57:369-374 (1996); Eghtedarzadeh & Henikoff, *Use of oligonucleotides to generate large deletions, Nucl. Acids Res.* 14: 5115 (1986); Fritz et al., *Oligonucleotide-directed construction of mutations: a gapped duplex DNA procedure without enzymatic reactions in vitro, Nucl. Acids Res.* 16: 6987-6999 (1988); Grundström et al., *Oligonucleotide-directed mutagenesis by microscale 'shot-gun' gene synthesis, Nucl. Acids Res.* 13: 3305-3316 (1985); Kunkel, *The efficiency of oligonucleotide directed mutagenesis, in Nucleic Acids & Molecular Biology* (Eckstein, F. and Lilley, D. M. J. eds., Springer Verlag, Berlin)) (1987); Kunkel, *Rapid and efficient site-specific mutagenesis without phenotypic selection, Proc. Natl. Mad. Sci. USA* 82:488-492 (1985); Kunkel et al., *Rapid and efficient site-specific mutagenesis without phenotypic selection, Methods in Enzymol.* 154, 367-382 (1987); Kramer et al., *The gapped duplex DNA approach to oligonucleotide-directed mutation construction, Nucl. Acids Res.* 12: 9441-9456 (1984); Kramer & Fritz *Oligonucleotide-directed construction of mutations via gapped duplex DNA, Methods in Enzymol.* 154:350-367 (1987); Kramer et al., *Point Mismatch Repair, Cell* 38:879-887 (1984); Kramer et al., *Improved enzymatic in vitro reactions in the gapped duplex DNA approach to oligonucleotide-directed construction of mutations, Nucl. Acids Res.* 16: 7207 (1988); Ling et al., *Approaches to DNA mutagenesis: an overview, Anal Biochem.* 254(2): 157-178 (1997); Lorimer and Pastan *Nucleic Acids Res.* 23, 3067-8 (1995); Mandecki, *Oligonucleotide-directed double-strand break repair in plasmids of Escherichia coli: a method for site-specific mutagenesis, Proc. Natl. Acad. Sci. USA,* 83:7177-7181 (1986); Nakamaye & Eckstein, *Inhibition of restriction endonuclease Nci I cleavage by phosphorothioate groups and its application to oligonucleotide-directed mutagenesis, Nucl. Acids Res.* 14: 9679-9698 (1986); Nambiar et al., *Total synthesis and cloning of a gene coding for the ribonuclease S protein, Science* 223: 1299-1301; (1984); Sakamar and Khorana, *Total synthesis and expression of a gene for the a-subunit of bovine rod outer segment guanine nucleotide-binding protein (transducin), Nucl. Acids Res.* 14: 6361-6372 (1988); Sayers et al., *Y-T Exonucleases in phosphorothioate-based oligonucleotide-directed mutagenesis, Nucl. Acids Res.* 16:791-802 (1988); Sayers et al., *Strand specific cleavage of phosphorothioate-containing DNA by reaction with restriction endonucleases in the presence of ethidium bromide,* (1988) *Nucl. Acids Res.* 16: 803-814; Sieber, et al., *Nature Biotechnology,* 19:456-460 (2001); Smith, *In vitro mutagenesis, Ann. Rev. Genet.* 19:423-462 (1985); *Methods in Enzymol.* 100: 468-500 (1983); *Methods in Enzymol.* 154: 329-350 (1987); Stemmer, *Nature* 370, 389-91 (1994); Taylor et al., *The use of phosphorothioate-modified DNA in restriction enzyme reactions to prepare nicked DNA, Nucl. Acids Res.* 13: 8749-8764 (1985); Taylor et al., *The rapid generation of oligonucleotide-directed mutations at high frequency using phosphorothioate-modified DNA, Nucl. Acids Res.* 13: 8765-8787 (1985); Wells et al., *Importance of hydrogen-bond formation in stabilizing the transition state of subtilisin, Phil. Trans. R Soc. Lond. A* 317: 415-423 (1986); Wells et al., *Cassette mutagenesis: an efficient method for generation of multiple mutations at defined sites, Gene* 34:315-323 (1985); Zoller & Smith, *Oligonucleotide-directed mutagenesis using M13-derived vectors: an efficient and general procedure for the production of point mutations in any DNA fragment, Nucleic Acids Res.* 10:6487-6500 (1982); Zoller & Smith, *Oligonucleotide-directed mutagenesis of DNA fragments cloned into M13 vectors, Methods in Enzymol.* 100:468-500 (1983); and Zoller & Smith, *Oligonucleotide-directed mutagenesis: a simple method using two oligonucleotide primers and a single-stranded DNA template, Methods in Enzymol.* 154:329-350 (1987). Additional details on many of the above methods can be found in *Methods in Enzymology* Volume 154, which also describes useful controls for trouble-shooting problems with various mutagenesis methods.

In addition, serum half-life and other properties of VLPs and immunogens can be modulated using mutagenesis, or by other well known methods, such as by the addition of PEG or other protective (e.g., saccharide) moieties to the enzymes.

Pharmaceutical Compositions and Administration to Patients

Antitoxins and immunogenic compositions of the invention can be formulated into pharmaceutical compositions. These compositions may comprise, in addition to one or more VLP (or decorated VLP), an available pharmaceutically acceptable excipient, carrier, buffer, stabilizer or the like. Such materials should typically be non-toxic and should not interfere with the efficacy of the active ingredient. The precise nature of the carrier or other material depends on the route of administration, e.g., whether administration is via oral, rectal, intravenous, cutaneous, subcutaneous, nasal, intramuscular, intraperitoneal or other routes. The route is chosen to put the composition into contact either with the immune system, or with the site of toxin production/activity.

For example, pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or local injection, e.g., at the site of an affliction (e.g., a skin lesion), the active ingredient will be in the form of a parenterally acceptable aqueous solution which has suitable pH, isotonicity and stability. Those of skill in the art are able to prepare suitable solutions using, for example, isotonic vehicles such as sodium chloride injection, Ringer's injection, lactated Ringer's injection, or the like. Preservatives, stabilizers, buffers, antioxidants and/or other additives are also optionally included, as required.

Whether it is a VLP antitoxin or immunogenic composition, that is to be given to an individual, administration is preferably in a "prophylactically effective amount" (e.g., enough to prevent or ameliorate the effects of a disease, e.g., anthrax infection) or a "therapeutically effective amount" (prophylaxis optionally also can be considered therapy), this being an amount sufficient to show a benefit to the individual (e.g., enough to prevent death from the relevant toxin, or to induce a protective immune response to the disease agent). The actual amount administered, and rate and time-course of administration, will depend on the nature and severity of what is being, treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found, e.g., in the current edition of Remington's e.g., *Remington: The Science and Practice of Pharmacy*, Twenty First Edition (2005).

The compositions may be administered alone or in combination with other treatments, either simultaneously or sequentially dependent upon the condition to be treated. Thus, in the treatment of anthrax, the VLP, etc., can be administered in combination with other available therapies.

The compositions can be administered to human patients, or to non-human veterinary patients. For example, anthrax infects sheep, cattle and other livestock animals, as well as humans, and the compositions of the invention can be used to treat livestock as well as human patients.

Additional Details for Administering Antitoxins

Antitoxins are preferably administered as soon as possible after exposure to a toxin. The route of administration can vary depending on the application. Many toxins are active in the circulatory system, making i.v. or i.p. delivery especially useful. However, many toxins also can act e.g., in the digestive system (e.g., botulinium toxins), making oral delivery appropriate in those instances, or in the nervous system (e.g., diphtheria toxin) making CSF, intracranial or spinal administration appropriate.

Additional Details for Administering VLP Vaccines and Making Antibodies

VLP vaccines can be administered in a manner designed to elicit an immune response. This can typically be achieved by simple injection (s.c., i.m., etc.). Optionally, a decorated VLP vaccine can be administered in conjunction with an adjuvant designed to boost an immune response, e.g., depending on the host species, including, but not limited to Freund's (complete or incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Decorated VLP vaccines, in addition to being useful as protective agents (vaccines), are also useful in the production of antibodies against a displayed immunogen. Such antibodies are useful as labeling reagents to detect the immunogen, e.g., to detect or monitor infection in a patient for diagnostic or prognostic purposes, or for in situ labeling in clinical or laboratory applications. In addition, such antibodies act as antitoxins against the immunogen at issue. Thus, antibodies can be raised in one host, isolated by standard methods, and injected into a patient as an antitoxin.

As used herein, the term "antibody" includes, but is not limited to, polyclonal antibodies, monoclonal antibodies, humanized or chimeric antibodies and biologically functional antibody fragments, which are those fragments sufficient for binding of the antibody fragment to the protein.

For the production of antibodies to a decorated VLP, various host animals may be immunized by injection with the VLP. Such host animals may include human patients, livestock animals (e.g., sheep, cattle, hogs, horses, etc.), or laboratory animals (e.g., rabbits, mice or rats).

Polyclonal antibodies are heterogeneous populations of antibody molecules derived from the sera of animals immunized with the VLP. For the production of polyclonal antibodies, host animals, such as those described above, may be immunized by injection with the VLP, e.g., supplemented with adjuvants as also described above.

Monoclonal antibodies (mAbs), which are homogeneous populations of antibodies to a particular VLP antigen, may be obtained by any technique that provides for the production of antibody molecules by continuous cell lines in culture. These include, but are not limited to the hybridoma technique of Kohler and Milstein (*Nature* 256:495-497, 1975; and U.S. Pat. No. 4,376,110), the human B-cell hybridoma technique (Kosbor et al., *Immunology Today* 4:72, 1983; Cole et al., *Proc. Nat'l. Acad. Sci. USA* 80:2026-2030, 1983), and the EBV-hybridoma technique (Cole et al., *Monoclonal Antibodies and Cancer Therapy*, Alan R. Liss, Inc., pp. 77-96, 1985). Such antibodies may be of any immunoglobulin class, including IgG, IgM, IgE, IgA, IgD, and any subclass thereof. The hybridoma producing the mAb of this invention may be cultivated in vitro or in vivo. Production of high titers of mAbs in vivo makes this the presently preferred method of production.

For details regarding antibody production and their use in assays, in situ antigen detection, or the like, see Harlow and Lane (1988) *Antibodies, A Laboratory Manual*, Cold Spring Harbor Publications, New York; Harlow and Lane (1998) *Using Antibodies: A Laboratory Manual* Cold Spring Harbor Lab Press ISBN-10: 0879695447; Schelling (2002) *Monoclonal Antibody Protocols* ISBN: 0896036553, Humana Press; Welschof and Krauss (2002) *Recombinant Antibodies for Cancer Therapy: Reviews and Protocols (Methods in Molecular Biology)* ISBN: 0896039188 Humana Press; Albitar (2007) *Monoclonal Antibodies: Methods and Protocols (Methods in Molecular Biology)* ISBN: 1588295672 Humana Press.

DEFINITIONS

Unless defined otherwise, all technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

An "antitoxin" is a composition that blocks an activity of a toxin in an organism. Common antitoxins bind to the toxin, blocking the toxin's usual mode of operation. Antitoxins can include molecular decoys such as toxin receptor molecules or portions thereof that bind to the toxin, and/or antibodies previously raised against the toxin.

An "anthrax antitoxin" is an antitoxin that ameliorates an effect of an anthrax toxin. For example, a recombinant VLP of the invention can include a VWA domain of an ANTRX2 receptor, which acts as a molecular decoy by binding PA. This results in protection against effects of the anthrax toxin.

The term "anthrax toxin" refers to any component or product of the anthrax toxin. That is the toxic effects of anthrax are predominantly due to an AB-type toxin made up of a single receptor-binding B subunit and two enzymatic A subunits. The A subunits are edema factor (EF, 89 kD), an adenylate cyclase that raises intracellular cAMP levels, and lethal factor (LF, 90 kD)), a zinc protease that cleaves mitogen-activated protein kinase kinases. The receptor binding B subunit is protective antigen (PA), which is initially synthesized as an 83 kD precursor. Upon receptor binding, PA83 is cleaved by furin into a 63 kD product, which forms heptamers that bind EF to form edema toxin (EdTx) and LF to form lethal toxin (LeTx). Any or all of these are encompassed by the term "anthrax toxin." In addition, molecules derived from a wild-type anthrax toxin, e.g., through mutagenesis or recombinant methods, are also included within the term.

An "anthrax protective antigen" (PA) is the portion of an anthrax toxin that recognizes an anthrax receptor (e.g., anthrax toxin receptor/tumor endothelial marker 8 (ANTXR1) or capillary morphogenesis gene 2 (ANTXR2)). Both the 83 kD precursor and the 63 kD furin cleavage product are optionally included within the term, as is the heptameric form thereof. In addition, molecules derived from a wild-type anthrax PA, e.g., through mutagenesis or recombinant methods, are also included within the term.

A "capillary morphogenesis gene 2" (ANTRX2) gene encodes an ANTRX2 protein which is a receptor protein that mediates Bacillus anthracis killing of macrophages following spore challenge. A variety of alleles and synonyms for ANTRX2 are known in the art. The universal protein knowledge database (UniProt) has several accession numbers for ANTRX2 proteins, including P58335, Q4W5H6 and Q32Q26 (GenBank accession no. AY23345). NCBI has an accession number for the coding gene (Enterez GeneID: 118429). Synonyms for the protein include anthrax toxin receptor 2 precursor, Capillary morphogenesis gene 2 protein, CMG2, CMG-2, FLJ31074, ISH, JHF, MGC111533, and MGC45856. In the present invention, the terms for the polypeptide and protein include all allelic variants of the given polypeptides and genes at the accession numbers above, as well as derivative variants thereof, particularly those that can bind PA. ANTRX2 typically binds to the protective antigen (PA) of *Bacillus anthracia* in a divalent cation-dependent manner, with the following preference: calcium>manganese>magnesium>zinc. Binding of PA leads to heptamerization of the receptor-PA complex. The gene and corresponding protein are well characterized, binding laminin, and collagen type IV.

Additional details regarding ANTRX2 proteins and nucleic acids can be found in Genebank at AAI07877 (human) NP_598499 487 aa linear anthrax toxin receptor 2 [*Mus musculus*]; NP_477520, anthrax toxin receptor 2 [*Homo sapiens*] gi|50513243|ref|NP_477520.2| [50513243]; P58335 Anthrax toxin receptor 2 precursor (Capillary morphogenesis gene 2 protein) (CMG-2); AAH76595 cDNA clone, Anthrax toxin receptor 2 [*Mus musculus*] gi|49901393|gb|AAH76595.1|[49901393]; ABD74633 capillary morphogenesis protein 2A [*Danio rerio*]; NM_058172 *Homo sapiens* anthrax toxin receptor 2 (ANTXR2), mRNA gi|68342041|ref|NM_058172.3|[68342041]; NM_133738 *Mus musculus* anthrax toxin receptor 2 (Antxr2), mRNA gi|50355938|ref|NM_133738.1|[50355938]; BC107876 cDNA clone, *Homo sapiens* anthrax toxin receptor 2, mRNA (cDNA clone MGC:111533 IMAGE:6108432), complete cds gi|79154031|gb|BC107876.1|[79154031]; BC076595 cDNA clone, *Mus musculus* anthrax toxin receptor 2, mRNA (cDNA clone MGC:100142 IMAGE:30649897), complete cds gi|49901392|gb|BC076595.1|[49901392]; DQ415957 *Danio rerio* capillary morphogenesis protein 2A (cmg2a) mRNA, complete cds; gi|89513612|gb|DQ415957.1| [89513612]; BC034001 *Homo sapiens* anthrax toxin receptor 2, mRNA (cDNA clone IMAGE:4894326), complete cds gi|21708157|gb|BC034001.1|[21708157]; DV770783 ILLUMIGEN_MCQ_70414 Katze_MMOV *Macaca mulatta* cDNA clone IBIUW:40677 5—similar to Bases 26 to 766 highly similar to human ANTXR2 (Hs.162963), mRNA sequence gi|82614725|gb|DV770783.1|[82614725]; BC123757 cDNA clone, *Bos taurus* similar to Anthrax toxin receptor 2 precursor (Capillary morphogenesis gene-2 protein) (CMG-2), mRNA (cDNA clone MGC:143297 IMAGE: 8231847), complete cds gi|115305013|gb|BC123757.1| [115305013]; NM_001076826 *Bos taurus* similar to Anthrax toxin receptor 2 precursor (Capillary morphogenesis gene-2 protein) (CMG-2) (MGC143297), mRNA gi|116003874|ref|NM_001076826.1|[116003874]; NM_001044709 *Danio rerio* similar to Anthrax toxin receptor 2 precursor (Capillary morphogenesis protein-2) (CMG-2) (LOC557239), mRNA gi|113374124|ref|NM_001044709.1|[113374124]; NM_058172 *Homo sapiens* anthrax toxin receptor 2 (ANTXR2), mRNA gi|68342041|ref|NM_058172.3|[68342041]; NM_133738 *Mus musculus* anthrax toxin receptor 2 (Antxr2), mRNA gi|50355938|ref|NM_133738.1|[50355938]; BC003908 *Mus musculus* anthrax toxin receptor 2, mRNA (cDNA clone IMAGE:3484366), partial cds gi|13278123|gb|BC003908.1| [13278123]; XM_680988 *Danio rerio* similar to Anthrax toxin receptor 2 precursor (Capillary morphogenesis protein-2) (CMG-2) (LOC557845), mRNA; AAI23758 cDNA clone, Similar to Anthrax toxin receptor 2 precursor (Capillary morphogenesis gene-2 protein) (CMG-2) [*Bos taurus*]; XP_686080 similar to Anthrax toxin receptor 2 precursor (Capillary morphogenesis protein-2) (CMG-2) [*Danio rerio*]; AAK77222 capillary morphogenesis protein-2 [*Homo sapiens*].

An "extracellular von Willebrand Factor A" (VWA) domain is a polypeptide domain that displays structural similarity to the VWA domain originally described in the blood coagulation protein von Willebrand factor (VWF). VWA domains fold into a compact three-layered para-Rossmann type fold, consisting of seven helices surrounding a core of five parallel beta-strands and one short antiparallel beta-strand. VWAs are a well studied protein domain typically involved in cell adhesion, extracellular matrix proteins, and in integrin receptors. The crystal structure of the VWA domain from ANTRX2 (as well as many other proteins) has been solved. See, Lacy et al. (2004) Crystal structure of the von Willebrand factor A domain of human capillary morphogenesis protein 2: An anthrax toxin receptor *Proc Natl Acad Sci USA*. 101(17): 6367-6372 (Published online 2004 Apr. 12. doi: 10.1073/pnas.0401506101).

A domain is "heterologous" to a specified polypeptide when it is derived from a polypeptide that is different from the specified polypeptide. A heterologous toxin binding domain of a VLP is a polypeptide domain that is heterologous to the capsid protein of the VLP and that binds a toxin moiety. A heterologous immunogen binding domain of a VLP is a domain that is heterologous to the capsid protein of the VLP and that binds an immunogen. A heterologous toxin binding domain and a heterologous immunogen binding domain can, in some embodiments, be the same domain. For example, the VWA domain of an ANTRX2 polypeptide binds anthrax toxin (PA), making it an antitoxin, as well as an immunogen binding domain for the display of PA.

A "nodavirus-derived virus like particle" is a capsid that is made up of capsid proteins that are derived from a nodavirus. The capsid proteins can be nodavirus capsid proteins, or can be recombinant proteins that include sequences derived from such capsid proteins (or both). In general, a second polypeptide is "derived from" a first polypeptide when the second polypeptide (or coding nucleic acid thereof) is produced using sequence information from the first polypeptide, or a coding nucleic acid thereof, or when the second polypeptide (or coding nucleic acid thereof) is produced from the first polypeptide (or coding nucleic acid thereof) by artificial, e.g., recombinant methods. For example, when the second polypeptide is made by mutating a nucleic acid encoding the first polypeptide, and expressing the resulting mutated nucleic acid, the second polypeptide is said to be "derived from" the first. Similarly, when the second polypeptide is made using sequence information from the first polypeptide, e.g., by mutating the sequence of the first polypeptide in silico and then synthesizing, e.g., a corresponding nucleic acid that encodes the second polypeptide and expressing it, the resulting second polypeptide is derived from the first polypeptide.

Virus Like Particles (VLPs) are also alternatively referred to as viral nanoparticles (VNs). The ANTRX2 VLP/VN herein denoted as including the extracellular von Willebrand Factor A (VWA) domain, e.g., domain I, are alternately denoted VNI (viral nanoparticles with I domain). Therefore, the uncomplexed form is alternatively denoted VNI and the form with PA bound is alternatively denoted VNI-PA.

An amino acid residue in a protein "corresponds" to a given residue when it occupies the same essential structural position within the protein as the given residue. For example, a selected residue in a selected nodavirus protein other than FHV corresponds to residue 206 (or e.g., 264) of the FHV capsid protein when the selected residue occupies the same essential spatial or other structural relationship to other amino acids in the selected protein as residue 206 (or 264) does with respect to the other residues in the FHV capsid protein. Thus, if the selected protein is aligned for maximum homology with the FHV capsid protein, the position in the aligned selected protein that aligns with FHV capsid residue is said to correspond to it Instead of a primary sequence alignment, a three dimensional structural alignment can also be used e.g., where the structure of the selected protein is aligned for maximum correspondence with the FHV capsid protein and the overall structures compared. In this case, an amino acid that occupies the same essential position a residue in the structural model is said to correspond to the residue.

A "toxin" is a toxic substance, typically of biological origin. A variety of toxins are made by bacteria (anthrax toxin, botulinum toxin, necrotizing toxin from Necrotizing fasciitis, etc.), as well as, e.g., a variety of jellyfish, snakes, insects and spiders. Toxins relevant to the invention typically include polypeptides or polypeptide components.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. Accordingly, the following examples are offered to illustrate, but not to limit, the claimed invention.

Example 1

A Viral Nanoparticle with Dual Function as an Anthrax Antitoxin and Vaccine

The recent use of *Bacillus anthracis* as a bioweapon has stimulated the search for novel antitoxins and vaccines that act rapidly and with minimal adverse effects. *B. anthracis* produces an AB-type toxin composed of the receptor-binding moiety protective antigen (PA) and the enzymatic moieties edema factor and lethal factor. PA is a key target for both antitoxin and vaccine development. We used the icosahedral insect virus Flock House virus as a platform to display 180 copies of the high affinity, PA-binding von Willebrand A (VWA) domain of the ANTXR2 cellular receptor. The chimeric virus-like particles (VLPs) correctly displayed the receptor VWA domain on their surface and inhibited lethal toxin action in in vitro and in vivo models of anthrax intoxication. Moreover, VLPs complexed with PA elicited a potent toxin-neutralizing antibody response that protected rats from anthrax lethal toxin challenge after a single immunization without adjuvant. This recombinant VLP platform represents a novel and highly effective dually-acting reagent for treatment and protection against anthrax.

To develop a reagent that functions both as an anthrax antitoxin and as a molecular scaffold for an efficient anthrax vaccine, we took advantage of an icosahedral virus platform that permits polyvalent display of the extracellular VWA domain of ANTXR2. This platform is based on Flock House virus (FHV), a non-enveloped, icosahedral (T=3) insect virus of the family nodaviridae [16]. The FHV capsid is composed of 180 subunits of a single type of coat protein, and the icosahedral, solid shell encapsidates a bipartite, single-stranded RNA genome. The crystal structure of FHV particles shows that the coat protein contains several surface-exposed loops that can be targeted for insertion of foreign proteins and peptides [17]. Here we report the synthesis and structural characterization of FHV-VWA$_{ANTXR2}$ chimeric particles and provide evidence for their efficacy as an anthrax toxin inhibitor in vitro and in vivo. In addition, we used the chimeric particles as a scaffold for the multivalent display of PA and show that this complex functions as a potent vaccine against LeTx.

FHV-VWA$_{ANTXR2}$ Chimeric Protons Assemble into Virus-Like-Particles.

The VWA domain of ANTXR2 forms a compact structure that adopts a Rossmann-like α/β-fold with a metal ion-dependent adhesion site motif that is involved in PA binding [9,18]. The N and C termini of this domain, residues C39 and C218, respectively, are closely juxtaposed thereby permitting, in principle, genetic insertion into a loop on a carrier protein. Modeling studies of the FHV coat protein subunit indicated that two surface-exposed loops at amino acid positions 206 and 264 would accommodate the 181 amino acid ANTXR2 VWA domain without disrupting coat protein assembly into virus-like particles (VLPs) (FIG. 1A). Based on these predictions, two chimeric proteins were generated. In FHV-VWA$_{ANTXR2}$ chimera 206, the VWA domain and a C-terminal two amino acid linker (Ala-Glu) replaced FHV coat protein residues 207-208 (FIG. 1B). In FHV-VWA$_{ANTXR2}$ chimera 264, the VWA domain replaced FHV residues 265-267. The chimeric proteins were expressed in Sf21 insect cells using recombinant baculovirus vectors. In this system, wildtype (wt) FHV coat protein forms VLPs Whose high resolution structure is virtually indistinguishable from that of native virions. However, VLPs contain random cellular RNA instead of the FHV genome and are therefore not infectious [19].

Putative chimeric VLPs were purified from the cells by sucrose gradient centrifugation and material sedimenting at a position similar to that observed for native virions was harvested and analyzed by SDS-PAGE. As shown in FIG. 1C, both samples contained a major protein and a slower migrating minor protein of the appropriate molecular weights (≈63 kD, the combined molecular weight of the 43 kD FHV coat protein and the 20 kD ANTXR2 VWA domain). Since the FHV coat protein undergoes a spontaneous cleavage reaction after assembly of particles (FIG. 1B) [20], the minor protein likely represented the unprocessed precursor protein, whereas the major protein represented the post-assembly cleavage product. Capsid proteins representing chimera 264 migrated more slowly through the gel than those representing chimera 206, even though the amino acid composition of the two polypeptides was virtually identical. The reason for this differential behavior is not known but could reflect subtle differences in denaturation of the proteins under SDS-PAGE conditions.

Electron microscopy of negatively stained samples confirmed the presence of VLPs in the gradient-purified material (FIG. 1D). Compared to the smooth exterior of native FHV virions, the surface of the chimeric particles was rough and distinct protrusions were visible. The appearance of the particles suggested that they were filled with RNA, as stain did not penetrate the interior. This conclusion was supported by the sedimentation rate of the VLPs, which was indistinguishable from that of wt FHV.

Structural Analysis of FHV-VWA$_{ANTXR2}$ VLPS.

Figure 5:
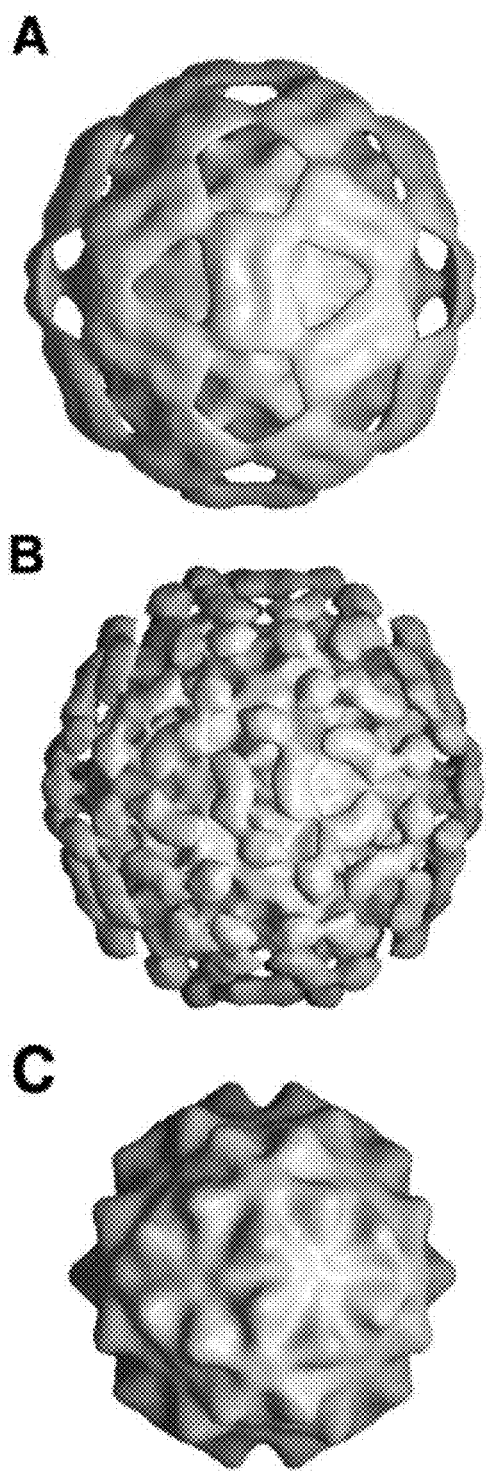
FIG. 5 Panels A-C shematically show 3D surface-shaded reconstructions of (a) FHV-VWA$_{ANTXR2}$ chimera 206, (b) FHV-VWA$_{ANTXR2}$ chimera 264 and (c) wt FHV.
Figure 6:
FIG. 6 Panels A-B. Pseudoatomic models of FHV-VWA$_{ANTXR2}$ chimeras.
Figure 6:
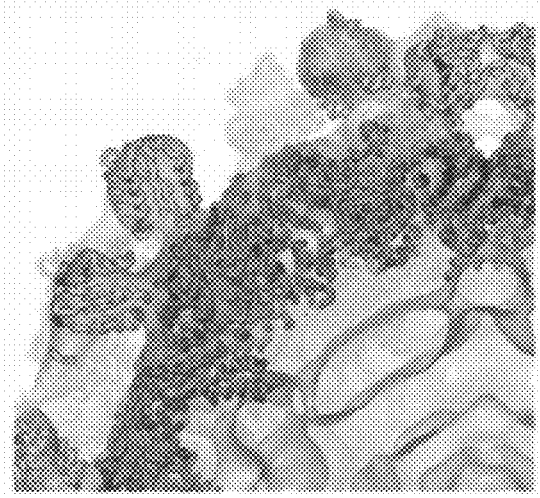
Figure 7:
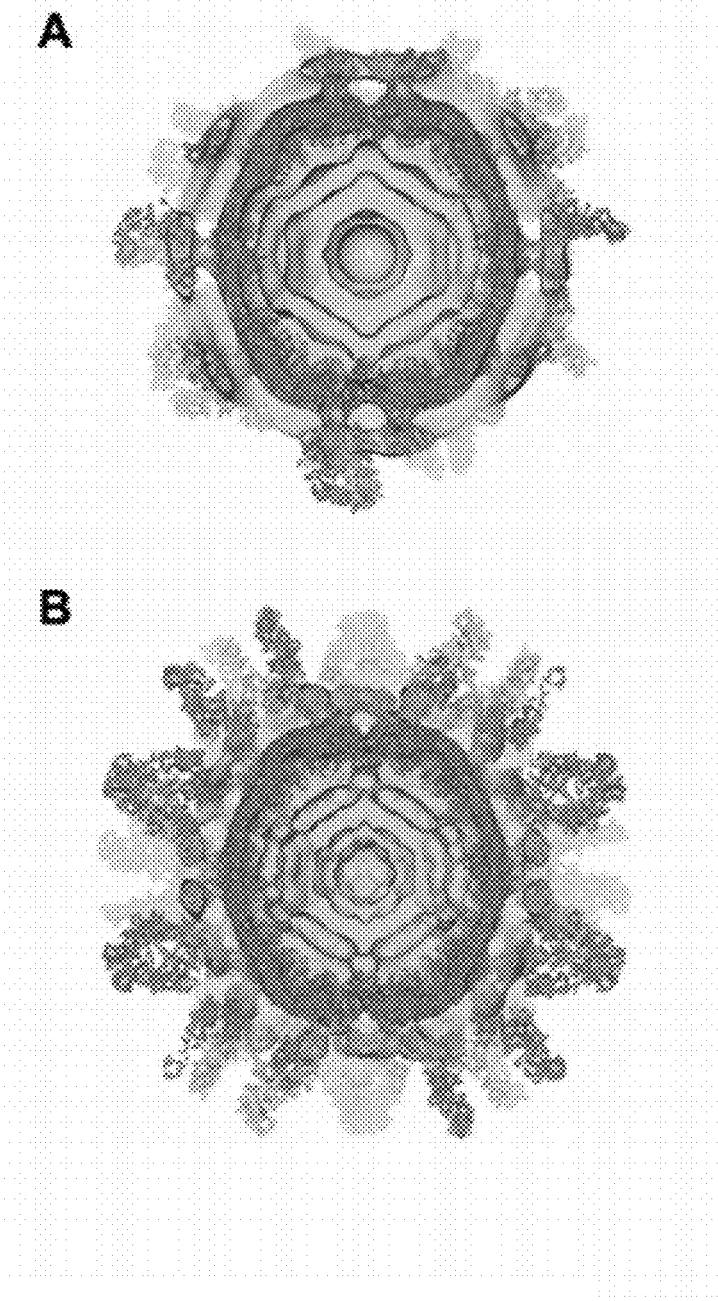
FIG. 7 Panels A-B. In silico model of PA83 bound to the surface of FHV-VWA$_{ANTXR2}$ chimeras.

Electron cryomicroscopy and image reconstruction of the FHV-VWA$_{ANTXR2}$ VLPs showed that, compared to wt FHV particles (FIG. 5 C), both chimeric particles displayed additional density at higher radius (FIGS. 5A and 5B), in agreement with the protrusions that were visible in negatively stained, samples (FIG. 1D). To define the arrangement of the VWA domains on the surface of the chimeric particles, pseudoatomic models were generated by fitting the X-ray coordinates of the FHV coat protein subunit and the ANTXR2 VWA domain into the cryoEM density maps (FIGS. 3A and 3B; 6A and 6B). The models revealed that in chimera 206 the VWA domains were closely juxtaposed at the quasi three-fold axes. Two of the three VWA domains in each asymmetric unit closely interacted with their twofold related counterparts, thereby creating an offset cluster of six domains. In contrast, the insertion site chosen for chimera 264 allowed for wider spacing and more even distribution of the individual VWA domains on the particle surface.

Figure 2:
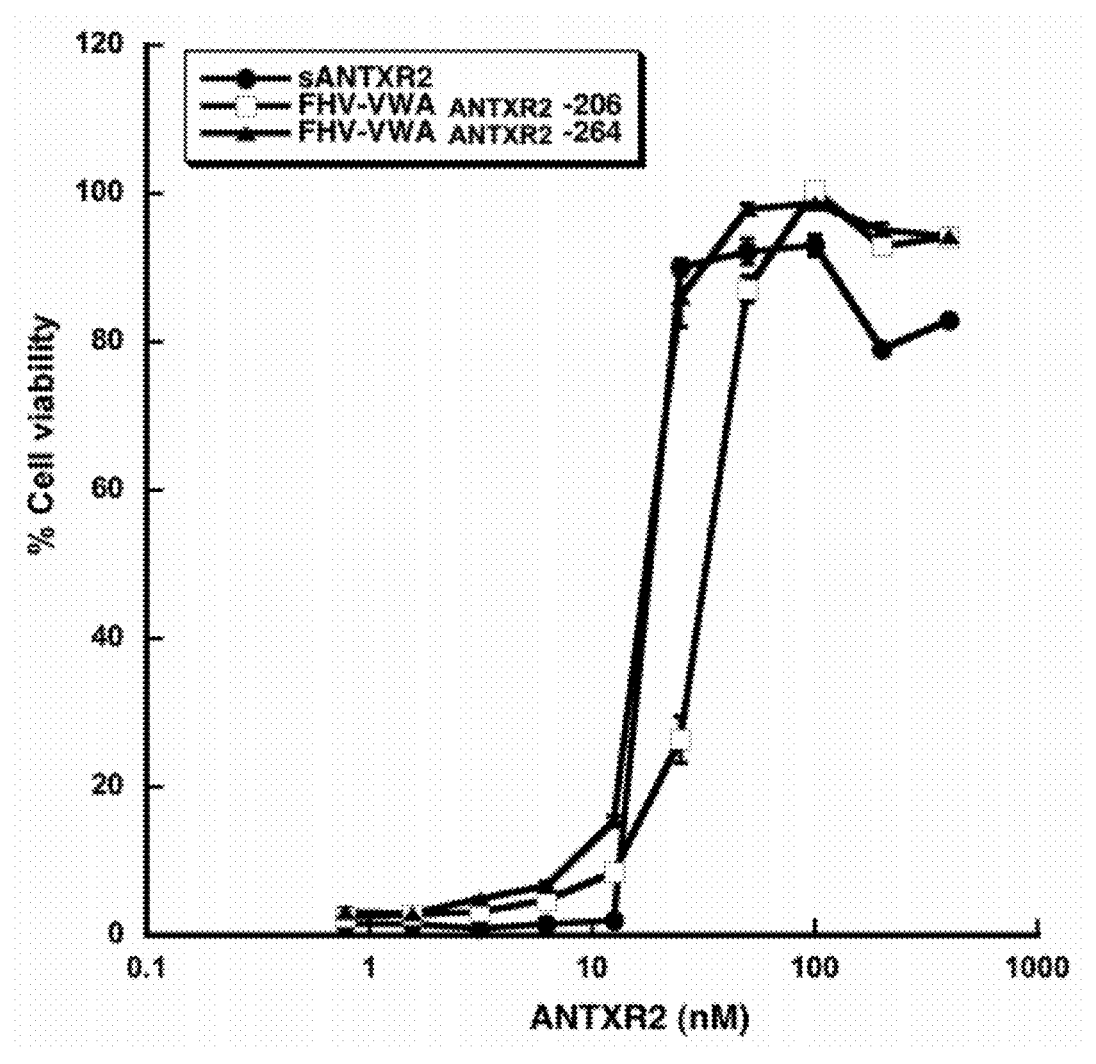
Figure 8A:
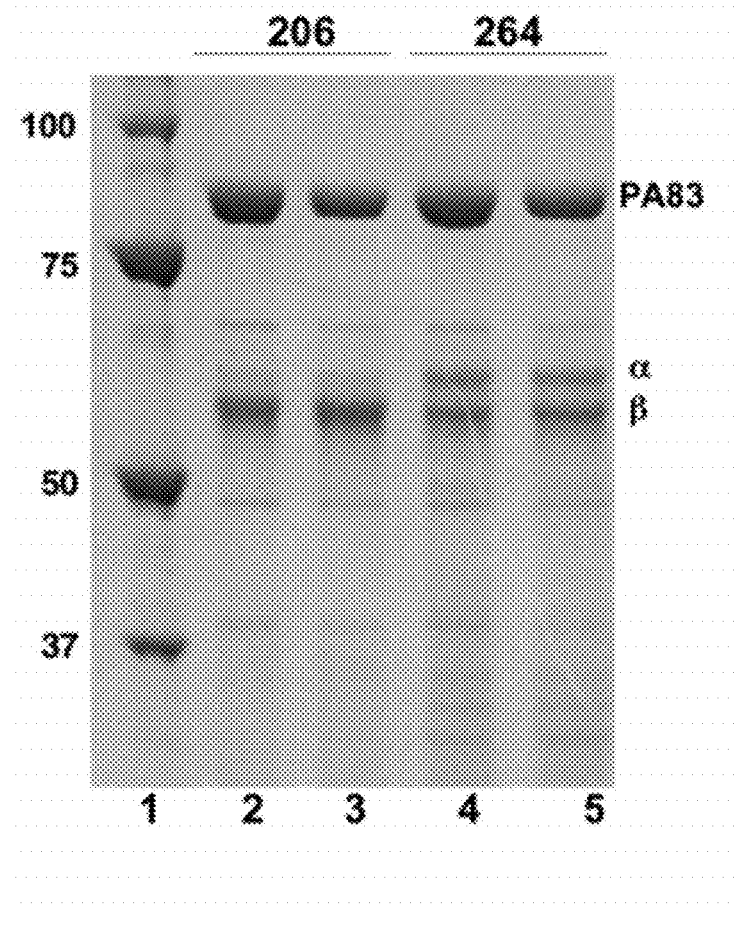
FIG. 8 Panels A-B provide a gel photograph (panel A) and a quantitative histogram showing the number of PA83 per chimera (Panel B).
Figure 8B:
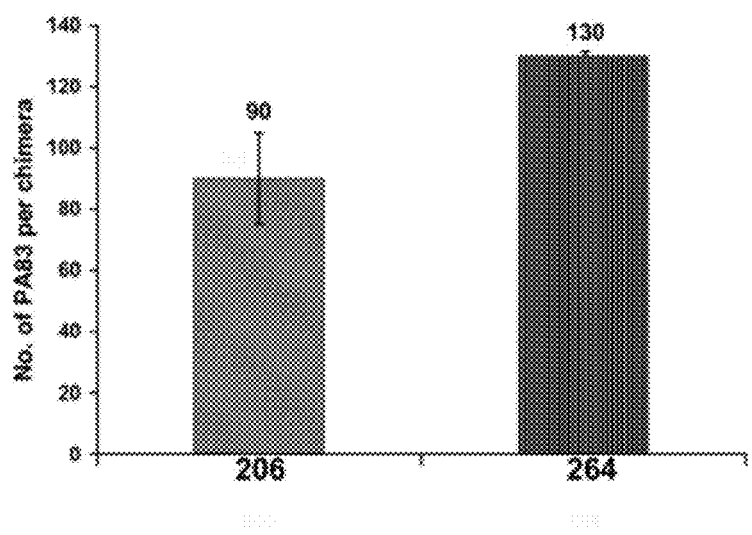

To investigate the accessibility of PA to the VWA domains, PA83 was computationally docked onto the VWA domains of the pseudoatomic models of chimeras 264 and 206 using the X-ray structure of PA63 complexed with the ANTXR2 VWA domain as a guide [9,18]. It was evident that chimera 264 could accommodate significantly more PA molecules than chimera 206 given the wider spacing of the VWA domains on this particle (FIGS. 3C and 3D; 7A and 7B). Specifically, each subunit at the fivefold axes and three of the six subunits around the quasi-sixfold axes could bind PA83 without steric interference, giving a: total occupancy of 120 PA molecules per particle. In contrast, due to the close juxtaposition of the VWA domains on chimera 206, a maximum occupancy of 60 PA molecules per particle was predicted. These predictions were in close agreement with results from biochemical analyses of complexes formed between the particles and PA83 under saturating conditions. Specifically, gel electrophoresis combined with densitometric analysis showed that chimera 206 could bind an average of 90 PA83 ligands, whereas chimera 264 bound an average of 130 PA83 ligands (FIGS. 8A and 4B). Together, these results were consistent with the observation that a higher concentration of chimera 206 was, required to protect cells from intoxication with PA/LF$_N$-DTA (FIG. 2).

FHV-VWA$_{ANTXR2}$ VLPS Protect Cultured Cells from Intoxication

The soluble, monomeric ANTXR2 VWA domain (sANTXR2), expressed and purified from mammalian cells, was previously shown to effectively block entry of lethal toxin into susceptible cells by competing with cellular ANTXR2 for binding to PA [10]. PA has, a very high binding affinity for sANTXR2 ($K_d$=170 pM) and dissociates extremely slowly from this receptor decoy (half-life of the complex is approximately 17 hours) [21]. We used the same approach to test the inhibitory activity of FHV-VWA$_{ANTXR2}$ VLPs. Namely, the assay employed CHO-K1 cells and a modified form of lethal toxin; PA/LF$_N$-DTA, in which the N terminal portion of LF was fused to the catalytic portion of diphtheria toxin A-chain [22]. This recombinant toxin efficiently kills CHO-K1 cells within 48 hours and uses the same PA-dependent entry mechanism as wt LF. The assay revealed that chimera 264 protected cells as efficiently as sANTXR2, whereas a higher concentration of chimera 206 was required to achieve protection of the cells (FIG. 2). The corresponding IC$_{50}$ values for sANTXR2 and chimera 264 were 19.70±0.87 nM and 18.50±0.36 nM, respectively, while the IC$_{50}$ was 32.71±0.61 nM for chimera 206. Thus, chimera 264 performed as well as the highly potent, monomeric sANTXR2 inhibitor in this assay. To confirm the ability of the particles to neutralize native lethal toxin, a macrophage-based toxin neutralization assay was performed with chimera 264. The assay revealed that the particles protected RAW264.7 cells efficiently from a mixture of PA and wt lethal toxin and the measured IC$_{50}$ was 39.8+2.2 nM.

FHV-VWA$_{ANTXR2}$ Chimera 264 Protects Rats from Lethal Toxin Challenge.

We next tested whether the chimeric particles were capable of protecting rats against lethal toxin challenge as was demonstrated previously for sANTXR2 [10]. In vivo experiments were only performed with chimera 264 because it had shown higher potency in the cell intoxication assay (FIG. 2). As a positive control, sANTXR2 was used in parallel. Male Fisher 344 rats were inoculated intravenously with 5 minimal lethal doses (MILD) of LeTx either in the presence or absence of chimera 264 or sANTXR2 as previously described [10]. As shown in Table 1, both chimera 264 and sANTXR2 completely protected the animals when used at a molar ratio of 2:1 (ANTXR2:PA). Moreover, the animals did not exhibit any symptoms of intoxication such as agitation, respiratory distress or hypoxia. Injection vehicle (PBS) or wt FHV, used as a negative control, had no protective effect. While neither chimera 264 nor sANTXR2 were able to protect rats when used at a tenfold lower concentration (molar ratio of ANTXR2:PA=0.2:1), they each caused a delay in the time to death compared to the lethal toxin control (Table 1). The delay was notably longer for chimera 264 (89 min) than sANTXR2 (77 min) and the difference was highly significant (p=0.0046) suggesting increased therapeutic potency of the multivalent particles over monomeric sANTXR2 as an inhibitor of the anthrax toxin. It will be interesting to determine whether different pharmacokinetic profiles are observed in vivo for sANTXR2 and chimera 264.

TABLE 1

IN VIVO INTOXICATION EXPERIMENTS IN FISHER 344 RATS

| Groups | Molar ratio of VWA$_{ANTXR2}$: PA | Survivors/ total | Average TTD ± SD (min) |
|---|---|---|---|
| PBS | NA | 3/3 | NA |
| LeTx | NA | 0/5 | 69.2 ± 1.5 |
| FHV wt + LeTx | NA | 0/3 | 67.7 ± 5.1 |
| sANTXR2 + LeTx | 2:1 | 5/5 | NA |
| sANTXR2 + LeTx | 0.2:1 | 0/5 | 77 ± 4.6 |
| FHV-VWA$_{ANTXR2}$ 264 + LeTx | 2:1 | 5/5 | NA |
| FHV-VWA$_{ANTXR2}$ 264 + LeTx | 0.2:1 | 0/5 | 89.4 ± 5.4 |

TTD: Time to death.
NA: not applicable.
LeTx: Lethal toxin.
PBS vehicle of injection as negative control, lethal toxin (20 µg (240 pmol) of protective antigen (PA) and 8 µg (89 pmol) of lethal factor (LF), FHV wt was injected at a concentration of 21 µg/rat (480 pmol).

Computational Models of PA Bound to FHV-VWA$_{ANTXR2}$ Particles.

Results from the cell intoxication assays and LeTx challenge experiments in rats suggested that the chimeric particles could bind PA, which in turn indicated that the inserted VWA domains were correctly folded in the context of the FHV particle. The differential behavior of FHV-VWA$_{ANTXR2}$ chimeras 206 and 264 in cell intoxication assays, however, potentially reflected differences in the accessibility of PA to the VWA domains on the surface of the particles. To further investigate this PA63, the proteolytically activated form of PA, was computationally docked onto the VWA domains of the pseudoatomic models of chimeras 264 and 206 using the X-ray structure of PA63 complexed with the ANTXR2 VWA domain as a guide[9,17]. It was evident that chimera 264 could accommodate significantly more PA molecules than chimera 206 given the wider spacing of the VWA domains on this particle (compare FIGS. 3c and d). Specifically, each subunit at the fivefold axes and three of the six subunits around the quasi-sixfold axes could bind PA63 without steric interference, giving a total occupancy of 120 PA molecules per particle. In contrast, due to the close juxtaposition of the VWA domains on chimera 206, a maximum occupancy of 60 PA molecules per particle was predicted. These results were consistent with the observation that a twofold higher concentration of chimera 206 was required to protect cells from intoxication with PA/LF$_N$-DTA (FIG. 4). Assuming an occupancy of up to 120 of the 180 VWA domains on chimera 264, the particles were, however, more potent on a molar basis than sANTXR2. This enhancement could have been the result of polyvalent effects which are known to enhance the biological activity of peptides and proteins relative to their monomeric state[21].

FHV-VWA$_{ANTXR2}$ Particles Serve as a Highly Effective Vaccine Platform.

The observation that FHV-VWA$_{ANTXR2}$ chimera 264 functioned as a binding surface for multiple copies of PA suggested that a complex of the two components might constitute an effective antigen for induction of PA-specific antibodies. To test this complexes were prepared by mixing chimera 264 with an excess of PA83 and unbound PA83 was removed by ultracentrifugation. Electron microscopic analysis showed that PA83 formed thin protrusions emanating from the capsid surface.

For immunogenicity studies, rats (4/group) received two s.c. injections (0 and 3 weeks) of either 2.5 µg PA83, 5.4 µg of particle-PA complex (molar equivalent of 2.5 µg PA83 assuming an occupancy of 120 VWA domains), or 2.9 µg of chimera 264. No adjuvants were employed in these experiments. ELISA assay of pre- and post-inoculation sera showed that animals immunized with the complex had significantly higher levels of anti-PA antibody than animals receiving PA alone both at week 3 (p=0.0028 compared to PA alone) and after boosting (week 7; p=0.0118 compared to PA alone) (FIG. 4A). No significant antibody response against ANTXR2 VWA was detected in these animals, but a response against FHV protein was observed after the boost in rats that were immunized with the complex (FIGS. 4B and C). Why animals immunized with chimera 264 alone did not mount a similar immune response against FHV protein is not clear. The presence of PA may somehow enhance the response to FHV or may influence the localization or interaction of FHV particles with antigen-presenting cells causing a difference in the observed anti-FHV antibody titer.

To test whether the anti-PA antibodies were protective against anthrax toxin, the rats were challenged by intravenous inoculation with 10 MLDs of LeTx. All animals that had been immunized with the particle-PA complex survived, whereas all but one of the animals in the PA83 group died (FIG. 4D). Survival versus death correlated well with the level of anti-PA antibody detected in the sera. However, the animal in the PA-only group that survived LeTx challenge had a serologic response to PA that was well below that of a non-surviving animal in the same group (FIG. 4D).

Based on the observation that animals immunized with the particle-PA complex showed a significant level of anti-PA antibody as early as 3 weeks after the first immunization (FIG. 4A), we investigated whether animals could be protected against LeTx after a single injection. Rats (5/group) were immunized once with increased doses of the particle-PA complex (10.8 µg), PA83 (5 µg), or chimera 264 (5.8 µg) as a control. After 3 weeks the animals were bled and challenged one week later with 10 MLDs of LeTx. All rats that were immunized with the particle-PA complex survived, whereas all other animals died (FIG. 4F). Of those that died, one animal had a serologic antibody response to PA that was greater than that of two animals in the group of survivors (FIGS. 4E and 4F) indicating that the magnitude of the antibody response is not a reliable predictor of protection. Serial dilution assay showed that the average reciprocal anti-PA titer in animals immunized with the particle-PA complex was 3240, and in vitro LeTx neutralization assays confirmed the neutralizing activity of these antibodies. (ED50:54). Taken together our results show that multivalent display of PA on the FHV-VWA$_{ANTXR2}$ scaffold yields a significant advantage over monovalent, soluble PA as an immunogen for anthrax toxin.

In this example we have provided and developed a novel reagent that combines the functions of anthrax antitoxin and vaccine in a single compound. It is based on multivalent display of the ANTXR2 VWA domain on the surface of the icosahedral, insect nodavirus FHV. We demonstrated that the recombinant VLPs protect cultured cells and rats from anthrax intoxication as efficiently as the highly potent sANTXR2 receptor decoy and that they induced a potent immune response against LeTx when coated with PA. This immune response was neutralizing in vitro and protected animals against LeTx challenge following a single administration without adjuvant.

The immunogenicity studies showed that polyvalent display of PA induces a more potent immune response than monomeric, recombinant PA (rPA), which is currently being, developed as a second-generation anthrax vaccine [15,23]. Ordered arrays of antigens permit particularly efficient cross-linking of B cell receptors which in turn leads to faster and more robust B cell proliferation [24,25,26]. Given the exceptionally tight binding of PA to ANTXR2 under natural conditions. (K$_d$=170 pM) [21] it is reasonable that complexes formed between chimera 264 and PA are sufficiently stable to serve as an immunogen in vivo. Results from in vitro cell intoxication experiments support this, showing that the complexes were stable for at least 40 hrs at 37° C. Naturally occurring PA neutralizing antibodies do not bind to the receptor-binding surface of PA [27]. PA4 immobilized on these particles should be able to elicit a protective immune response. Indeed, rats survived lethal toxin challenge four weeks after a single injection of the VLP-PA complex, whereas animals injected with an equivalent amount of rPA died. This result suggested rapid production of neutralizing antibodies in the absence of adjuvant, two key goals for the development of third generation anthrax vaccines. No significant antibody response to ANTXR2 was observed, presumably because there are only 2 amino acid differences between human ANTXR2 displayed on the particle and endogenous rat ANTXR2 [11].

It will be useful to characterize the neutralizing antibody response in individual animals after primary and secondary immunization. It will also be of interest to determine the mechanism by which toxin neutralization occurs. For example, there is a slight difference in antibody response after primary and secondary immunization and a wide range of antibody titers between individual animals (FIG. 4). It will be of interest to establish whether these differences correlate with epitope specificity or are based on other immunologic parameters. In addition, it is interesting to compare the findings in this example to those obtained with a *B. anthracis* spore-challenge model.

Because the chimeric particles are expressed from an mRNA that contains only the coding sequence of the modified FHV coat protein while all other FHV sequences are missing, the resulting virus-like particles are not infectious and thus cannot replicate in mammalian tissues [19]. Even native FHV particles are unable to initiate infection in mammals as they do not carry the FHV receptor and because FHV cannot replicate at temperatures above 31° C. [28]. We have also demonstrated previously that FHV VLPs expressed from baculovirus vectors in Sf21 cells do not contain baculoviral or cellular DNA [19], thus ruling out potential integration of foreign DNA into mammalian genomes. Based on these properties, the chimeric particles can be expected to have a desirable safety profile for applications in animals and humans.

While the potency of the nanoparticles herein as a vaccine is most likely due to polyvalent display of PA, polyvalency is less of a factor in the function of the particles as an antitoxin, given the extremely high affinity between PA and ANTXR2. Moreover, since PA binds as a monomer to the particles, little, if any polyvalent effect is to be expected. In fact, we detected no significant difference in $IC_{50}$ when comparing nanoparticles with soluble ANTXR2 in cell intoxication assays. However, the use of polyvalency to increase the affinity between a ligand and its target receptor is a useful general strategy [31]. Recently, Rai et al. [32] reported that "pattern matching" is a useful parameter for polyvalency to reach its maximum potential.

In vivo potency of viral nanoparticles is also determined in part by their pharmacokinetic parameters. Such parameters have recently been reported for viral nanoparticles derived from the plant virus cowpea mosaic virus [33]. It will be useful to determine any differences in plasma clearance kinetics and biodistribution of soluble ANTXR2 versus ANTXR2-containing nanoparticles.

The VWA domain of ANTXR2 was a candidate for insertion into a loop of the FHV coat protein because the N and C termini are only separated by 4.8 Å in the native structure [34]. In addition, this domain adopts a compact Rossmann-like α/β-fold that can evidently form independently within the context of a larger protein while not interfering with accurate folding of the carrier protein. This hypothesis was supported by the observation that the high-resolution structure of the VWA domain could be fitted easily into the cryoEM density maps. To our knowledge, Hepatitis B virus is the only other virus for which icosahedral surface display of an entire protein in its biologically active conformation has been demonstrated. In that case, genetic insertion of the green fluorescent protein in a surface-exposed loop of the core protein resulted in efficient formation of fluorescent HBV capsids [35].

In principle it should be possible to expand the use of the FHV platform to display additional anthrax antigens either in the presence or absence of the ANTXR2 VWA domain. Specifically, direct insertion of peptides or entire domains derived from PA, LF and EF is feasible as long as the termini of the domains are in close enough proximity for insertion into the FHV coat protein loops. It is also possible that the two insertion sites at positions 206 and 264 could be used in combination to create particles with multiple functionalities. This could greatly enhance the protection afforded by the resulting particles.

Numerous other strategies are being pursued to develop improved anthrax vaccines, including PA-expressing *Salmonella* [36] and *B. subtilis* [37], adenovirus encoding. PA domain 4 [38], rabies virus encoding GP-PA fusion protein [39] and bacteriophage T4 particles decorated with PA-hoc fusion proteins [40,41,42]. None of these, however, combine the function of vaccine and antitoxin as in the present invention. In those cases where immunized animals were challenged with LeTx or anthrax spores, only the adenovirus construct provided complete protection after a single immunization [38]. One strategy involves non-covalent surface display of intact proteins and protein complexes on bacteriophage T4 particles. The prolate lattice of the T4 capsid permits efficient surface presentation of anthrax toxin through in vitro addition of Hoc- and/or Soc protein fusions with PA, LF, or EF to hoc⁻soc⁻ phage either separately or in combination [40,42]. Mice immunized with phage displaying PA, EF and LF generated high levels of neutralizing antibodies [41] but results from toxin or spore challenge experiments have not yet been reported.

In summary, we have developed a reagent that serves a dual purpose in combating *B. anthracis* infection. It functions as a competitive inhibitor of anthrax toxin in vivo suggesting that it could be useful as a therapeutic compound, particularly in combination with standard antibiotic therapy. In addition, when complexed with PA, it has significant advantages as an immunogen compared to monomeric PA and thus forms the basis for development of an improved anthrax vaccine.

Further Example Details

Construction of recombinant baculoviruses. DNA fragments encoding FHV coat protein-ANTXR2 VWA domain chimeras were generated by overlap extension PCR using Pfu polymerase [43]. Three DNA fragments containing the nucleotide sequence for the N-terminal portion of the coat protein, the ANTXR2 VWA domain (GenBank accession no. AY23345, nts 115-657, amino acids 38-218) and the C-terminal portion of the coat protein, were initially generated. The template used for generating segments containing the FHV coat protein sequence was plasmid pBacPAK9RNA2 [44], which contains the full-length cDNA of FHV RNA2 in baculovirus transfer vector pBacPAK9 (BD Biosciences). The template used for generating the segment containing the ANTXR2 VWA coding sequence was a derivative of plasmid PEGFP-N1 [8]. Following overlap extension PCR, the full-length product was digested with BamH1 and XbaI, gel-purified and ligated into equally digested pBacPAK9. The transfer vector was amplified in *E. coli* strain DH5α, purified and sequenced to confirm the presence of the ANTXR2 VWA sequence and to ensure the absence of inadvertent mutations. Recombinant baculoviruses AcFHV-VWA$_{ANTXR2}$-264 and AcFHV-VWA$_{ANTXR2}$-206 were generated by transfecting Sf21 cells with a mixture of transfer vector and linearized Bsu36I-linearized BacPAK6 (BD Biosciences) baculovirus DNA as described previously [43].

Cells and infection. *Spodoptera frugiperda* cells (line IPLB-Sf21) were propagated and infected as described previously [19]. *Trichoplusia ni* cells were propagated and infected as described by Dong et al. [45] except that EX-CELL 401 medium was replaced with ESF921 (Expression Systems).

Purification of virus-like particles (VLPs). VLPs were purified from *T. ni* suspension cultures 5 to 6 days after infection. NP-40 substitute (Fluka) was added to the culture to a final concentration of 1% (v/v) followed by incubation on ice for 10-15 min. Cell debris was pelleted by centrifugation in a Beckman JA-14 rotor at 15,300×g for 10 minutes at 4° C. VLPs in the supernatant were precipitated by addition of NaCl to a final concentration of 0.2 M and polyethylene glycol 8000 (Fluka) to a final concentration of 8% (wt/vol) and stirring the mixture at 4° C. for one hour. The precipitate was collected by centrifugation at 9632×g for 10 min at 4° C. in a JA-14 rotor and resuspended in 50 mM HEPES buffer, pH 7.5. Insoluble material was removed by centrifugation at 15,300×g for 20 min at 4° C. VLPs in the clarified supernatant were pelleted through a 4-ml 30% (wt/wt) sucrose cushion in 50 mM Hepes, pH 7.5, by centrifugation in a Beckman 50.2 Ti rotor at 184,048×g for 2.5 h at 11° C. The pellet was resuspended in 50 mM Hepes buffer, pH 7.5 and loaded onto a 10-40% (wt/wt) sucrose gradient in the same buffer. The gradients were spun in a Beckman SW 28 rotor for 3 h at 103,745×g. VLPs were collected from the gradient by inserting a needle below the VLP band and aspirating the material into a syringe. Alternatively, gradients were fractionated with continuous absorbance at 254 nm on an ISCO gradient fractionator at 0.75 ml/min and 0.5 min per fraction. Fractions containing VLPs were then dialyzed against 50 mM Hepes, pH 7.5 and concentrated to 1-5 mg/ml using a centrifugal concentrator with a 100,000 MW cut off (Amicon, Millipore). The final protein concentration was determined by BCA assay (Pierce Chemicals) and purity was evaluated by densitometry (Fluor Chem™ SP, Alpha Innotech) after electrophoresis on a 10% Bis-Tris gel stained with Simply Blue (Invitrogen).

Electron microscopy. Samples of gradient-purified VLPs were negatively stained with 1% (wt/v) uranyl acetate. A drop of each sample was adsorbed to a glow-discharged, collodion-covered copper grid and allowed to adsorb for 1-2 min. Excess solution was removed by blotting with filter paper. The grids were washed and blotted with filter paper three times by floating on droplets of 50 mM Hepes, pH 7.5. Each grid was then treated three times with a drop of 1% uranyl acetate solution and left in the third drop for 1-2 min prior to blotting and air drying. The samples were viewed in a Philips/FEI CM 100 transmission electron microscope at 100 kV.

Electron cryomicroscopy and image reconstruction. Frozen-hydrated samples were prepared using standard methods [46]. In brief, an aliquot of the sample was applied to a glow-discharged Quantifoil holey carbon-coated grid (2/4 Cu—Rh), blotted with filter paper, and rapidly plunged into liquid ethane. Low-dose electron micrographs of FHV-VWA$_{ANTXR2}$-264 VLPs were recorded onto Kodak SO163 film at a magnification of 45,000× on a Philips/FEI CM120 transmission electron microscope. For FHV-VWA$_{ANTXR2}$-206 VLPs, low-dose micrographs were recorded on a CCD camera at a magnification of 50,000× on a Philips/FE Tecnai20 transmission electron microscope. The grids were maintained at −180° C. using a Gatan 626 cryo-stager Micrographs with minimal astigmatism and drift, as assessed by visual inspection and optical diffraction, were digitized with a Zeiss microdensitometer (Z/I Imaging) giving a step-size of 3.1 Å on the specimen. Images recorded on the CCD camera had a step-size of 2.26 Å. Particle images were extracted with the program X3D[47] and were processed by polar Fourier transform methods using the program PFT[48]. A previously calculated model of wt FHV [49] was used as the starting model. Initial refinement cycles were restricted to the radii spanning the FHV capsid and then relaxed to incorporate the extra domains. Using a Fourier shell correlation cut-off value of 0.5, the FHV-VWA$_{ANTXR2}$-206 and FHV-VWA$_{ANTXR2}$-264 maps were refined to resolutions of 25 and 23 Å, respectively.

Generation of pseudoatomic models. The atomic coordinates of the FHV coat protein subunit and the VWA domain of ANTXR2 (PDB ID: 1SHT) were used to generate a pseudoatomic model of the FHV-VWA$_{ANTXR2}$-206/264 virus-like particles. Specifically, the models were created with the program 0 [50] by visually positioning the ANTXR2 VWA domains at the surface of the FHV structure and adjusting for overlap. The models were then further refined against the structure factor amplitudes derived from the cryo-EM density using the program CNS [51]. Individual subunits and domains of the FHV-VWA$_{ANTXR}$2 chimera were allowed to move independently as rigid bodies and subjected to five rounds of 20 cycles of rigid body refinement. Protective antigen 83 (PA83) molecules were docked onto the resulting FHV-VWA$_{ANTXR2}$-206/264 models using the structure of PA63 complexed with the ANTXR2 VWA domain (PDB-ID: 1T6B) as a guide [9]. Once all 180 ANTXR2 VWA domains on the FHV-VWA$_{ANTXR2}$ chimera were populated with PA83 molecules, a minimal number of PA molecules were selectively removed to relieve steric clashes with neighboring PA molecules.

Quantification of PA83 bound to chimeras 206 and 264. Recombinant PA83 (List Biological Laboratories, Inc, CA) in 5 mM Hepes, 50 mM NaCl, pH 7.5 was mixed with purified chimeras 206 and 264 in 50 mM Hepes, pH 7.5 in a ratio of 180:1 (equimolar amounts of PA83 and VWA domains). Following incubation for 20 mM. at room temperature an aliquot from each of the samples was removed and stored at −20° C. pending analysis. The remainder of the samples was transferred to an ultracentrifuge tube and underlayed with a 30% (wt/wt) sucrose cushion in 50 mM Hepes pH 7.5. Complexes of chimeras decorated with PA83 were pelleted by centrifugation at −200,000×g for 45 min. The complexes were resuspended in 50 mM Hepes, mixed with SDS loading buffer and heated at 95° C. for 10 minutes. Aliquots were electrophoresed through a 4-12% Bis-Tris polyacrylamide gel, in parallel with the aliquots taken before pelleting. The gels were stained with Simply Blue (Invitrogen). The amount of protein in each bands was determined by densitometric analysis using Fluor Chem SP (Alpha Innotech).

Cell intoxication assay with CHO-Kb 1 cells. Cell intoxication studies were performed in CHO-K1 cells as described previously [10]. Briefly, $5 \times 10^3$ cells in 100 µl Hams-F12 nutrient mixture (Gibco BRL) supplemented with 10% fetal bovine serum were plated into wells of a 96-well microtitre plate a day prior to the assay. Varying amounts of FHV-VWA$_{ANTXR2}$ VLP or soluble ANTXR2 [8] were preincubated for 20 min. in 100 µl medium containing PA and LF$_N$-DTA at a molar concentration of $10^{-8}$ and $10^{-10}$, respectively. The mixture was added to the cells, which were incubated at 37° C. for approximately 40 hrs. The medium was then replaced with 50 µl Celltiter-glo reagent (Promega) diluted 1:1 with PBS. Luciferase activity as a measure of cell viability was determined with a luminometer (TopCount NXT, Perkin Elmer). Non-linear regression analysis was used to calculate IC$_{50}$ values (PRISM, GraphPad).

Macrophage-based toxin neutralization assay. RAW264.7 cells ($5 \times 10^4$) were plated in each well of a white 96-well tissue culture plate (Corning Costar) with 100 µl Dulbecco's Modified Eagle Medium (Gibco) supplemented with 10% standard fetal bovine serum the day before the assay. Varying amounts of FHV-VWA$_{ANTXR2}$ VLP were preincubated for 20 mm. in 400 µl medium containing PA and LF at a molar concentration of $10^{-8}$ and $10^{-9}$, respectively. The mixture (100 µl) was added to the cells in triplicate and incubated at 37° C. for approximately 5 hrs. Cell viability was determined as described for CHO-K1 cells.

Toxin neutralization assay. RAW264.7 cells ($10^4$) were plated in each well of a white 96-well tissue culture plate (Corning Costar) with 100 µl Dulbecco's Modified Eagle Medium (Gibco) supplemented with 10% standard fetal bovine serum the day before the assay. Individual sera from animals vaccinated either with PA83 or FHV-VWA$_{ANTXR2}$-PA83 complex were pooled and serial dilutions made in DMEM were mixed with 100 µl DMEM containing PA and LF at a molar concentration of $10^{-8}$ and $10^{-9}$, respectively. The mixture was pre-incubated for 1 hr at room temperature and then added to the cells. Each sample was tested in triplicate. Cells were incubated at 37° C. for approximately 24 hrs. The medium was then replaced with 50 µl Celltiter-glo reagent (Promega) diluted 1:1 with PBS. Luciferase activity as a measure of cell viability was determined with a luminometer (TopCount NXT, Perkin Elmer). Toxin neutralization titer was reported as the reciprocal dilution at which 50% of the cells were protected from LeTx.

LeTx challenge with FHV-VWA$_{ANTRX2}$ VLPs. LeTx challenge experiments were performed in cannulated, male Fisher 344 rats (180-200 g, Harlan, Indianapolis, Ind.) according to protocols approved by the Scripps Institutional Animal Care and Use Committee. LeTx for each rat was prepared by mixing 20 µg PA and 8 µg LF (List Biological Laboratories, Campbell, Calif.). All rats were anesthetized with isofluorane and inoculated through a jugular vein cannula with 500 µl of LeTx (control), or LeTx premixed with FHV-VWA$_{ANTXR2}$ VLPs or sANTXR2 (test). Additional rat control groups were injected with either PBS or wild-type FHV. Rats recovered from anesthesia within five minutes after dosing and were monitored for symptoms of intoxication (agitation, respiratory distress, hypoxia) and death as determined by cessation of respiration.

Statistical analysis. Data are presented as mean±S.D. Significance was reported using the Student's unpaired T-test (Prism, GraphPad Software Inc., San Diego Calif.). p values<0.05 were considered statistically significant. Data were also analyzed using 2-way ANOVA followed by Tukey's post-comparison test to confirm significance.

Preparation of FHV-VWA$_{ANTRX2}$ chimera 264-PA83 complexes. Purified chimera 264 VLPs in 50 mM Hepes, pH 7.5 were mixed with a 4-fold molar excess of recombinant PA83 (List Biological Laboratories, Inc, CA) in 5 mM Hepes, 50 mM NaCl, pH 7.5 and incubated at room temperature for 20 min with mild agitation. The sample was then transferred to an ultracentrifuge tube and underlayed with a 30% (wt/wt) sucrose cushion in 50 mM Hepes pH 7.5. Complexes of chimera 264 decorated with PA83 were pelleted by centrifugation at 197,568×g at 11° C. in an SW41Ti rotor for 1.5 h or an SW 55 Ti rotor for 45 min. The complexes were resuspended in 50 mM Hepes and analyzed by electrophoresis to confirm the presence of chimera 264 and PA83 proteins.

Rat Immunization and LeTx challenge. Immunization studies were performed in male Harlan Sprague Dawley (HSD) rats (180-200 g, Harlan, Indianapolis, Ind.) according to protocols approved by the Scripps Institutional Animal Care and Use Committee. For double dose immunization, rats were injected s.c. with 200 µl containing either 2.5 µg of PA83 (List Biological Laboratories, Inc, CA), 5.4 µg of FHV-VWA$_{ANTXR2}$-264-PA83 (molar equivalent of 2.5 µg PA83), or 2.9 µg FHV-VWA$_{ANTXR2}$-264 (molar equivalent of particles complexed with PA83) all prepared in PBS. For single dose immunization, rats were injected s.c. with 200 µl containing either 5 µg of PA83, 10.8 µg of FHV-VWA$_{ANTXR2}$-264-PA83 (molar equivalent of 5 µg PA83), or 5.8 µg of FHV-VWA$_{ANTXR2}$-264 (molar equivalent of particles complexed with PA83) all in PBS. Rats were anesthetized with isofluorane before all procedures. Serum was prepared from blood (200 µl per rat) collected from the retro-orbital plexus before immunization, three weeks post primary immunization, and four weeks post secondary immunization (study 1 only). LeTx challenge experiments were performed 13 weeks post initial immunization for the double dose immunization study and 4 weeks post immunization for the single dose immunization study. LeTx for each rat was prepared by mixing 40 µg PA and 8 µg LF (List Biological Laboratories, Campbell, Calif.) in PBS. Rats were anesthetized with isofluoranes and inoculated with 500 µl of LeTx or PBS (control) by intravenous tail vein injection. Rats recovered from anesthesia within five minutes after dosing and were monitored for symptoms of intoxication and death as described above.

Antibody Detection. Serum samples were tested for antibody response to PA, ANTXR2, and FHV by ELISA, assays. Briefly, microtitre Immulon 2HB 96-well plates (Dynex Technologies, Inc.) were coated with 100 µl of 10 µg/ml PA83, sANTXR2, or FHV in coating buffer (0.1M NaHCO3 pH 8.5), blocked with 3% non-fat milk in TBS, and incubated with serum samples diluted 1:100 and 1:1,000 in 1% non-fat milk in TBS pH 7.0 with 0.05% Tween 20 for 1 hour at room temperature. After washing, wells were incubated with biotin-SP-conjugated donkey anti-rat IgG (Jackson Immunoresearch, West Grove, Pa.) diluted 1:20,000 for 1 hour at room temperature. Plates were washed and incubated for 45 minutes with streptavidin-alkaline phosphatase conjugate (GE Healthcare Bio-Sciences Corp., Piscataway, N.J.) diluted 1:5,000 in TBS. After washing, plates were incubated with p-nitrophenyl phosphate (Sigma-Aldrich, St Louis, Mo.) at 37° C. for 20 minutes. 2N NaOH was added to stop the reaction and the signal was quantified using an ELISA reader (Molecular Devices, Sunnyvale, Calif.) at 405 nm.

AMINO ACID SEQUENCE OF FHV-CMG2 CHIMERA 264. CMG2 SEQUENCE IS UNDERLINED.

(SEQ ID NO: 1)
MVNNNRPRRQRAQRVVVTTTQTAPVPQQNVPRNGRRRRNRTRRNRRRVRG

MNMAALTRLSQPGLAFLKCAFAPPDFNTDPGKGIPDRFEGKVVSRKDVLN

QSISFTAGQDTFILIAPTPGVAYWSASVPAGTFPTSATTFNPVNYPGFTS

MFGTTSTSRSDQVSSFRYASMNVGIYPTSNLMQFAGSITVWKCPVKLSTV

QFPVATDPATSSLVHTLVGLDGVLAVGPDNFSESFIKGVFSQSACNEPDF

EFNDILEGIQTLPP<u>SCRRAFDLYFVLDKSGSVANNWIEIYNFVQQLAERF</u>

<u>VSPEMRLSFIVFSSQATIILPLTGDRGKISKGLEDLKRVSPVGETYIHEG</u>

<u>LKLANEQIQKAGGLKTSSIIIALTDGKLDGLVPSYAEKEAKISRSLGASV</u>

<u>YCVGVLDFEQAQLERIADSKEQVFPVKGGFQALKGIINSILAQSC</u>SLGST

GQPFTMDSGAEATSGVVGWGNMDTIVIRVSAPEGAVNSAILKAWSCIEYR

PNPNAMLYQFGHDSPPLDEVALQEYRTVARSLPVAVIAAQNASMWERVKS

IIKSSLAAASNIPGPIGVAASGISGLSALFEGFGF

-continued

AMINO ACID SEQUENCE OF FHV-CMG2 CHIMERA 206. CMG2
SEQUENCE IS UNDERLINED (SEQ ID NO: 2)
MVNNNRPRRQRAQRVVVTTTQTAPVPQQNVPRNGRRRRNRTRRNRRRVRG

MNMAALTRLSQPGLAFLKCAFAPPDFNTDPGKGIPDRFEGKVVSRKDVLN

QSISFTAGQDTFILIAPTPGVAYWSASVPAGTFPTSATTFNPVNYPGFTS

MFGTTSTSRSDQVSSFRYASMNVGIYPTSNLMQFAGSITVWKCPVKLSTV

QFPVATSCRRAF<u>DLYFVLDKSGSVANNWIEIYNFVQQLAERFVSPEMRLS</u>

<u>FIVFSSQATIILPLTGDRGKISKGLEDLKRVSPVGETYIHEGLKLANEQI</u>

<u>QKAGGLKTSSIIIALTDGKLDGLVPSYAEKEAKISRSLGASVYCVGVLDF</u>

<u>EQAQLERIADSKEQVFPVKGGFQALKGIINSILAQS</u>CAEATSSLVHTLVG

LDGVLAVGPDNFSESFIKGVFSQSACNEPDFEFNDILEGIQTLPPANVSL

GSTGQPFTMDSGAEATSGVVGWGNMDTIVIRVSAPEGAVNSAILKAWSCI

EYRPNPNAMLYQFGHDSPPLDEVALQEYRTVARSLPVAVIAAQNASMWER

VKSIIKSSLAAASNIPGPIGVAASGISGLSALFEGFGF

CDNA SEQUENCE OF FHV RNA2

(SEQ ID NO: 3)
GTAAACAATTCCAAGTTCCAAAATGGTTAATAACAACAGACCAAGACGTC

AACGAGCTCAACGCGTTGTCGTCACAACAACCCAAACAGCGCCTGTTCCA

CAGCAAAACGTGCCACGTAATGGTAGACGCCGACGTAATCGCACGAGGCG

TAATCGCCGACGTGTGCGCGGAATGAACATGGCGGCGCTAACCAGATTAA

GTCAACCTGGTTTGGCGTTTCTCAAATGTGCATTTGCACCACCTGACTTC

AACACCGACCCCGGTAAGGGAATACCTGATAGATTTGAAGGCAAAGTGGT

CAGCCGAAAGGATGTCCTCAATCAATCTATCAGCTTTACTGCCGGACAGG

ACACTTTTATACTCATCGCACCTACCCCCGGAGTCGCCTACTGGAGTGCT

AGCGTTCCTGCTGGTACTTTTCCTACTAGTGCGACTACGTTTAACCCCGT

TAATTATCCGGGTTTTACATCGATGTTCGGAACAACTTCAACATCTAGGT

CCGATCAGGTGTCCTCATTCAGGTACGCTTCCATGAACGTGGGTATTTAC

CCAACGTCGAACTTGATGCAGTTTGCCGGAAGCATAACTGTTTGGAAATG

CCCTGTAAAGCTGAGTACTGTGCAATTCCCGGTTGCAACAGATCCAGCCA

CCAGTTCGCTAGTTCATACTCTTGTTGGTTTAGATGGTGTTCTAGCGGTG

GGGCCTGACAACTTCTCTGAGTCATTCATCAAAGGAGTGTTTTCACAGTC

GGCTTGTAACGAGCCTGACTTTGAATTCAATGACATATTGGAGGGTATCC

AGACATTGCCACCTGCTAATGTGTCCCTTGGTTCTACGGGTCAACCTTTT

ACCATGGACTCAGGAGCAGAAGCCACCAGTGGAGTAGTCGGATGGGCAA

TATGGACACGATTGTCATCCGTGTCTCGGCCCCTGAGGGCGCAGTTAACT

CTGCCATACTCAAGGCATGGTCCTGCATTGAGTATCGACCAAATCCAAAC

GCCATGTTATACCAATTCGGCCATGATTCGCCTCCTCTCGATGAGGTCGC

GCTTCAGGAATACCGTACGGTTGCCAGATCTTTGCCGGTTGCAGTGATAG

CGGCCCAAAATGCATCAATGTGGGAGAGAGTGAAATCCATCATTAAATCC

TCCCTGGCTGCTGCAAGCAACATTCCCGGCCCGATCGGTGTCGCCGCAAG

TGGTATTAGTGGACTGTCAGCCCTTTTTGAAGGATTTGGCTTTTAGAAGC

ATCCGGACGCCAACCTAACCGGGCAAGTATCCGAACAATCGGACATTTGG

CCACAATAAGCCCAATTTGGTTGAAGATTAAAGTAGTGAGCCCCCTTAGC

GCGAAACCGGAATTTATATTCCAAACCAGTTTAAGTCAACAGACTAAGGT

Accession Numbers
1. Genbank
Human capillary morphogenesis protein 2 (CMG2): AY23345
Flock House virus coat protein: NC004144.
2. Protein Data Bank
VWA domain of CMG2: 1SHT
B. anthracis protective antigen PA63 complexed with CMG2: 1T6B
3. Virus Particle Explorer
Flock House virus particle coordinates.

Figure Legends for Example 1

FIG. 1. (a) Ribbon diagram of a single FHV coat protein subunit showing the surface-exposed loops into which the VWA domain of ANTXR2 was inserted. (b) Schematic diagram showing structure of FHV-VWA$_{ANTXR2}$ chimeric proteins 206 (top) and 264 (bottom). Numbers refer to amino acid positions in the FHV coat protein. The assembly-dependent autocatalytic maturation cleavage occurs between Asn 363 and Ala 364. (c) Electrophoretic analysis of purified VLPs on a 10% Bis-Tris gel stained with Simply Blue (Invitrogen). Lane 1, molecular weight markers; lane 2, wt FHV VLPs; lane 3 FHV-VWA$_{ANTXR2}$ chimera 206; lane 4, FHV-VWA$_{ANTXR2}$ chimera 264. (d) Electron micrographs of gradient-purified wt and chimeric VLPs negatively stained with uranyl acetate. Bar=500 Å.

FIG. 2. Dose response curve showing cell viability as a function of antitoxin concentration. CHO-K1 cells were incubated with PA-LF$_N$DTA in the presence of increasing concentrations of sANTXR2, chimera 206, or chimera 264. After incubation at 37° C. for 48 hr, cell viability was determined with Celltiter-glo (Promega). Data points represent the mean±SD values for triplicate samples. All data were normalized to untreated cell controls.

Figure 3:
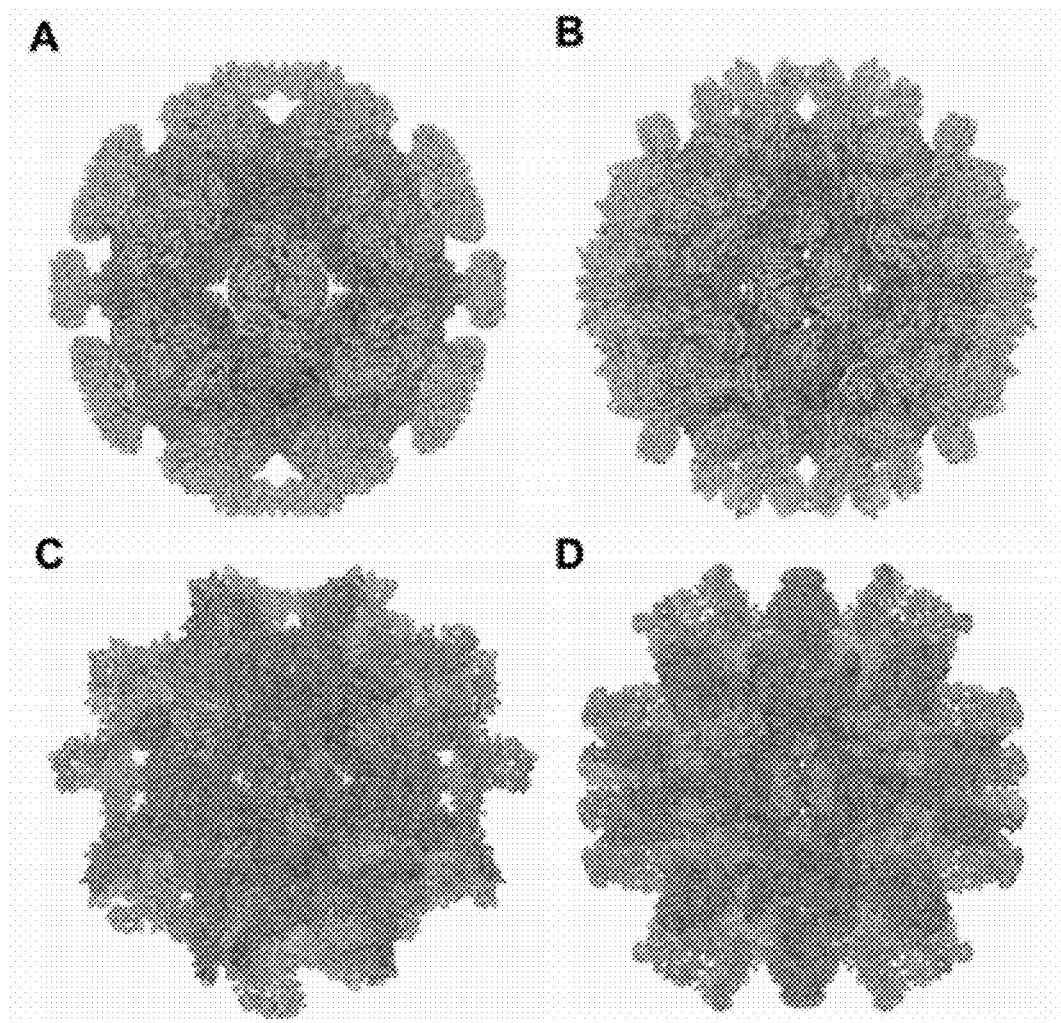
FIG. 3 Panels A-D. Top panels A-B: Pseudoatomic models of FHV-VWA$_{ANTXR2}$ chimeras. Panels show surface views. Bottom panels C-D: In silico model of PA83 bound to the surface of FHV-VWA$_{ANTXR2}$ chimeras.

FIG. 3. (a and b) Pseudoatomic models of FHV-VWA$_{ANTXR2}$ chimeras. X-ray coordinates of FHV capsid protein (green) and ANTXR2 VWA domain (yellow) were docked into the cryo-EM density of chimera 206 (a) and chimera 264 (b). Panels show surface views of the particles in the absence of the cryoEM density maps. Note the different distributions of the ANTXR2 domains on the surfaces of the VLPs. (c and d) In silico model of PA83 bound to the surface of FHV-VWA$_{ANTXR2}$ chimeras. PA83 (purple) was modeled onto the surface of chimera 206 (c) and chimera 264 (d) using the known high resolution X-ray structure of the ANTXR2—VWA/PA83 complex as a guide [34]. Panels show surface views of the entire particles to illustrate the difference in occupancy of PA83 on the two chimeras.

FIG. 4. Antibody and lethal toxin challenge response of immunized rats. (a-d) Rats (four per group) were immunized with FHV-VWA$_{ANTXR2}$-PA83 complex, FHV-VWA$_{ANTXR2}$ chimera alone, PA83 or PBS and boosted four weeks later. Serum samples were collected prior to as well as 3 and 7 weeks after immunization and tested by ELISA for IgG-specific antibody response to (a) PA, (b) VWA$_{ANTXR2}$ and (c) FHV coat protein. Data represent the mean±SD of animals in the respective groups and are shown for the 1:1000 serum dilution in panels (a) and (b) and for the 1:100 serum dilution in panel (c). In panel (a) at week 3, (*) indicates p=0.003 compared to PBS control and (**) indicates p=0.003 compared to PA83 alone. At week 7, (*) indicates p=0.005 compared to PBS control and (**) indicates p=0.012 compared to PA83 alone. (d) Relationship between anti-PA antibody level and survival of individual rats following challenge with 10 MLDs of LeTx. (e-f) Rats (five per group) were immunized once with FHV-VWA$_{ANTXR2}$-PA83 complex, FHV-VWA$_{ANTXR2}$ chimera alone, PA83 or PBS. Serum samples were collected prior to and 3 weeks after immunization, diluted 1:100, and tested for IgG-specific antibody response to PA (e). Data represent the mean±SD of animals in the respective groups. At week 3, (*) indicates p<0.0001 compared to PBS control and (**) indicates p=0.001 compared to PA83 alone. (f) Relationship between anti-PA antibody level and survival of individual rats following challenge with 10 MLDs of LeTx.

FIG. 5. 3D surface-shaded reconstructions of (a) FHV-$VWA_{ANTXR2}$ chimera 206, (b) FHV-$VWA_{ANTXR2}$ chimera 264 and (c) wt FHV. Note the protruding surface densities on the chimeric VLPs due to the addition of the VWA domain of ANTXR2. Bar=100 Å.

FIG. 6. Pseudoatomic models of FHV-$VWA_{ANTXR2}$ chimeras. X-ray coordinates of FHV capsid protein (green) and ANTXR2 VWA domain (yellow) were docked into the cryo-EM density (grey) of chimera 206 (a) and chimera 264 (b). Shown are octants of the density maps to illustrate the good fit of the high resolution X-ray structures into the cryoEM maps. Density within the interior of the capsid shell is ascribed to the encapsidated RNA.

FIG. 7. In silico model of PA83 bound to the surface of FHV-$VWA_{ANTXR2}$ chimeras. A maximum number of PA83 molecules (purple) was modeled onto the surface of chimera 206 (a) and chimera 264 (b), as limited by steric hindrance. Modeling was based on the known X-ray crystal structures of FHV [17] and ANTXR2—VWA/PA63 complex [9]. The FHV capsid protein and the VWA domain of ANTXR2 are in green and yellow, respectively. Panels show cross-sections of the chimeric particles, including the cryoEM density map (grey).

FIG. 8. Quantification of PA83 bound to chimera 206 and chimera 264. (a) Recombinant PA83 was mixed with purified chimeras 206 and 264 in a ratio of 180:1 (equimolar amounts of PA83 and VWA) and an aliquot from each sample was removed and stored. The remainder of the sample was centrifuged through a sucrose cushion to remove unbound. PA83 and the pellet was resuspended in electrophoresis buffer. Aliquots were electrophoresed through a 4-12% Bis-Tris polyacrylamide gel in, parallel with aliquots taken before pelleting. The gels were stained with Simply Blue (Invitrogen). Lane 1, molecular weight markers; lane 2, PA83 and chimera 206 before pelleting; lane 3, PA83 and chimera 206 after pelleting; lane 4, PA83 and chimera 264 before pelleting; lane 5, PA83 and chimera 264 after pelleting. (b) Quantitative representation of PA83 associated with chimeric particles after pelleting. Protein representing PA83 and chimeras 206 and 264 shown in panel (a) was quantified by densitometric analysis using Fluor Chem SP (Alpha Innotech) and the number of PA molecules bound to the particles calculated. The numbers were normalized to the amount of protein in the respective samples before pelleting.

For relevant example details see also: Manayani et al. (2007) A Viral Nanoparticle with Dual Function as an Anthrax Antitoxin and Vaccine *PLoS Pathog*. 2007 3(10): e142 (doi:10.1371/journal.ppat.0030142), incorporated herein by reference in its entirety.

NUMBERED REFERENCES FOR EXAMPLE 1 AND ABOVE

1. Mock M, Fouet A (2001) Anthrax. Annu Rev Microbiol 55: 647-671.
2. Inglesby T V, O'Toole T, Henderson D A, Bartlett J G, Ascher M S, et al. (2002) Anthrax as a biological weapon, 2002: updated recommendations for management. Jama 287: 2236-2252.
3. Collier R J, Young J A (2003) Anthrax toxin. Annu Rev Cell Dev Biol 19: 45-70.
4. Leppla S H (1982) Anthrax toxin edema factor: a bacterial adenylate cyclase that increases cyclic AMP concentrations of eukaryotic cells. Proc Natl Acad Sci USA 79: 3162-3166.
5. Duesbery N S, Webb C P, Leppla S H, Gordon V M, Klimpel K R, et al. (1998) Proteolytic inactivation of MAP-kinase-kinase by anthrax lethal factor. Science 280: 734-737.
6. Vitale G, Pellizzari R, Recchi C, Napolitani G, Mock M, et al. (1998) Anthrax lethal factor cleaves the N-terminus of MAPKKs and induces tyrosine/threonine phosphorylation of MAPKs in cultured macrophages. Biochem Biophys Res Commun 248: 706-711.
7. Bradley K A, Mogridge J, Mourez M, Collier R J, Young J A (2001) Identification of the cellular receptor for anthrax toxin. Nature 414: 225-229.
8. Scobie H M, Rainey G J, Bradley K A, Young J A (2003) Human capillary morphogenesis protein 2 functions as an anthrax toxin receptor. Proc Natl Acad Sci U S A 100: 5170-5174.
9. Lacy D B, Wigelsworth D J, Melnyk R A, Harrison S C, Collier R J (2004) Structure of heptameric protective antigen bound to an anthrax toxin receptor: a role for receptor in pH-dependent pore formation. Proc Natl Acad Sci USA 101: 13147-13151.
10. Scobie H M, Thomas D, Marlett J M, Destito G, Wigelsworth D J, et al. (2005) A soluble receptor decoy protects rats against anthrax lethal toxin challenge. J Infect Dis 192: 1047-1051.
11. Scobie H M, Wigelsworth D J, Marlett J M, Thomas D, Rainey G J, et al. (2006) Anthrax Toxin Receptor 2-Dependent Lethal Toxin Killing In Vivo. PLoS Pathog 2.
12. Wei W, Lu Q, Chaudry G J, Leppla S H, Cohen S N (2006) The LDL Receptor-Related Protein LRP6 Mediates Internalization and Lethality of Anthrax Toxin. Cell 124: 1141-1154.
13. Young J J, Bromberg-White J L, Zylstra C, Church J T, Boguslawski E, et al. (2007) LRP5 and LRP6 are not required for protective antigen-mediated internalization or lethality of anthrax lethal toxin. PLoS Pathog 3: e27.
14. Prevention CfDCa (2000) Use of anthrax vaccine in the United States. Recommendation of the Advisory Committee on Immunization Practices. Morb Mortal Wkly Rep 49 (RR-15): 1-20.
15. Gorse G J, Keitel W, Keyserling H, Taylor D N, Lock M, et al. (2006) Immunogenicity and tolerance of ascending doses of a recombinant protective antigen (rPA102) anthrax vaccine: a randomized, double-blinded, controlled, multicenter trial. Vaccine 24: 5950-5959.
16. Schneemann A, Reddy V, Johnson J E (1998) The structure and function of nodavirus particles: a paradigm for understanding chemical biology. In Maramorsch K, Murphy F A, Shatkin A J, editors. Advances in virus research. San Diego: Academic Press. pp. 381-446.

17. Fisher A J, Johnson J E (1993) Ordered duplex RNA controls capsid architecture in an icosahedral animal virus. Nature 361: 176-179.
18. Santelli E, Bankston L A, Leppla S H, Liddington R C (2004) Crystal structure of a complex between anthrax toxin and its host cell receptor. Nature 430: 905-908.
19. Schneemann A, Dasgupta R, Johnson J E, Rueckert R R (1993) Use of recombinant baculoviruses in synthesis of morphologically distinct virus-like particles of flock house virus, a nodavirus. J Virol 67: 2756-2763.
20. Gallagher T, Rueckert R R (1988) Assembly-dependent maturation cleavage in provirions of a small icosahedral insect ribovirus. J Virol 62: 3399-3406.
21. Wigelsworth D J, Krantz B A, Christensen K A, Lacy D B, Juris S J, et al. (2004) Binding stoichiometry and kinetics of the interaction of a human anthrax toxin receptor, CMG2, with protective antigen. J Biol Chem 279: 23349-23356.
22. Milne J C, Blanke S R, Hanna P C, Collier R J (1995) Protective antigen-binding domain of anthrax lethal factor mediates translocation of a heterologous protein fused to its amino- or carboxy-terminus. Mol Microbiol 15: 661-666.
23. Keitel W A (2006) Recombinant protective antigen 102 (rPA102): profile of a second-generation anthrax vaccine. Expert Rev Vaccines 5: 417-430.
24. Bachmann M F, Rohrer U H, Kundig T M, Burki K, Hengartner H, et al. (1993) The influence of antigen organization on B cell responsiveness. Science 262: 1448-1451.
25. Bachmann M F, Zinkernagel R M (1997) Neutralizing antiviral B cell responses. Annu Rev Immunol 15: 235-270.
26. Fehr T, Skrastina D, Pumpens P, Zinkernagel R M (1998) T cell-independent type I antibody response against B cell epitopes expressed repetitively on recombinant virus particles. Proc Natl Acad Sci USA 95: 9477-9481.
27. Vitale L, Blanset D, Lowy I, O'Neill T, Goldstein J, et al. (2006) Prophylaxis and therapy of inhalational anthrax by a novel monoclonal antibody to protective antigen that mimics vaccine-induced immunity. Infect Immun 74: 5840-5847.
28. Ball L A, Amann J M, Garrett B K (1992) Replication of nodamura virus after transfection of viral RNA into mammalian cells in culture. J Virol 66: 2326-2334.
29. Aulinger B A, Roehrl M H Mekalanos J J, Collier R J, Wang J Y (2005) Combining anthrax vaccine and therapy: a dominant-negative inhibitor of anthrax toxin is also a potent and safe immunogen for vaccines. Infect Immun 73: 3408-3414.
30. Sellman B R, Mourez M, Collier R J (2001) Dominant-negative mutants of a toxin subunit: an approach to therapy of anthrax. Science 292: 695-697.
31. Mammen M, Choi S K, Whitesides G M (1998) Polyvalent interactions in biological systems: implications for design and use of multivalent ligands and inhibitors. Angew Chem Int Ed 37: 2754-2794.
32. Rai P, Padala C, Poon V, Saraph A, Basha S, et al. (2006) Statistical pattern matching facilitates the design of polyvalent inhibitors of anthrax and cholera toxins. Nat Biotechnol 24: 582-586.
33. Singh P, Prasuhn D, Yeh R M, Destito G, Rae C S, et al. (2007) Bio-distribution, toxicity and pathology of cowpea mosaic virus nanoparticles in vivo. J Control Release 120: 41-50.
34. Lacy D B, Wigelsworth D J, Scobie H M, Young J A, Collier R J (2004) Crystal structure of the von Willebrand factor A domain of human capillary morphogenesis protein 2: an anthrax toxin receptor. Proc Natl Acad Sci USA 101: 6367-6372.
35. Kratz P A, Bottcher B, Nassal M (1999) Native display of complete foreign protein domains on the surface of hepatitis B virus capsids. Proc Natl Acad Sci USA 96: 1915-1920.
36. Stokes M G, Titball R W, Neeson B N, Galen J E, Walker N J, et al. (2007) administration of a *Salmonella enterica*-based vaccine expressing *Bacillus anthracis* protective antigen confers protection against aerosolized *B. anthracis*. Infect Immun 75: 1827-1834.
37. Duc le H, Hong. H A, Atkins H S, Flick-Smith H C, Durrani Z, et al. (2007) Immunization against anthrax using *Bacillus subtilis* spores expressing the anthrax protective antigen. Vaccine 25: 346-355.
38. McConnell M J, Hanna P C, Imperiale M J (2007) Adenovirus-based Prime-boost Immunization for Rapid Vaccination Against Anthrax. Mol Ther 15: 203-210.
39. Smith M E, Koser M, Xiao S, Siler C, McGettigan J P, et al. (2006) Rabies virus glycoprotein as a carrier for anthrax protective antigen. Virology 353: 344-356.
40. Shivachandra S B, Rao M, Janosi L, Sathaliyawala T, Matyas G R, et al. (2006) In vitro binding of anthrax protective antigen on bacteriophage T4 capsid surface through Hoc-capsid interactions: a strategy for efficient display of large full-length proteins. Virology 345: 190-198.
41. Shivachandra S B, Li Q, Peachman K K, Matyas G R, Leppla S H, et al. (2007) Multicomponent anthrax toxin display and delivery using bacteriophage T4. Vaccine 25: 1225-1235.
42. Li Q, Shivachandra S B, Leppla S H, Rao V B (2006) Bacteriophage T4 capsid: a unique platform for efficient surface assembly of macromolecular complexes. J Mol Biol 363: 577-588.
43. Venter P A, Krishna N K, Schneemann A (2005) Capsid protein synthesis from replicating RNA directs specific packaging of the genome of a multipartite, positive-strand RNA virus. J Virol 79: 6239-6248.
44. Krishna N K, Marshall D, Schneemann A (2003) Analysis of RNA packaging in wild-type and mosaic protein capsids of flock house virus using recombinant baculovirus vectors. Virology 305: 10-24.
45. Dong X F, Natarajan P, Tihova M, Johnson J E, Schneemann A (1998) Particle polymorphism caused by deletion of a peptide molecular switch in a quasi-equivalent virus. J Virol 72: 6024-6033.
46. Yeager M, Berriman J A, Baker T S, Bellamy A R (1994) Three-dimensional structure of the rotavirus haemagglutinin VP4 by cryo-electron microscopy and difference map analysis. Embo J 13: 1011-1018.
47. Conway J F, Cheng N, Zlotnick A, Wingfield P T, Stahl S J, et al. (1997) Visualization of a 4-helix bundle in the hepatitis B virus capsid by cryo-electron microscopy. Nature 386: 91-94.
48. Baker T S, Cheng R H (1996) A model-based approach for determining orientations of biological macromolecules imaged by cryoelectron microscopy. J Struct Biol 116: 120-130.
49. Tihova M, Dryden K A, Le T V, Harvey S C, Johnson J E, et al. (2004) Nodavirus coat protein imposes dodecahedral RNA structure independent of nucleotide sequence and length. J Virol 78: 2897-2905.
50. Jones T A, Zou J Y, Cowan S W, Kjeldgaard (1991) Improved methods for building protein models in electron density maps and the location of errors in these models. Acta Crystallogr A 47 (Pt 2): 110-119.

51. Brunger A T Adams P D, Clore G M, DeLano W L Gros P, et al. (1998) Crystallography & NMR system: Anew software suite for macromolecular structure determination. Acta Crystallogr D Biol Crystallogr 54 (Pt 5): 905-921.

Example 2

Other Applications of the VNI-Based Multivalent Platform: Combination Vaccines to Simultaneously Provide Protection Against Multiple Pathogens or Toxins An attractive feature of the VNI platform is that through the use of chimeric proteins with PA fused to other immunogens, it should be possible to use this as a versatile technology to generate rapidly acting and effective vaccines against other pathogens and their products. These other pathogens include category A, B, and C agents, some of which represent major bioterrorism threats. For example, there have been several recent advances in the development of mucosal vaccines against ricin and botulinum neurotoxins. However, in each case effective immunization involves multiple dosings with the immunogen (22-24).

Figures 9, 10:
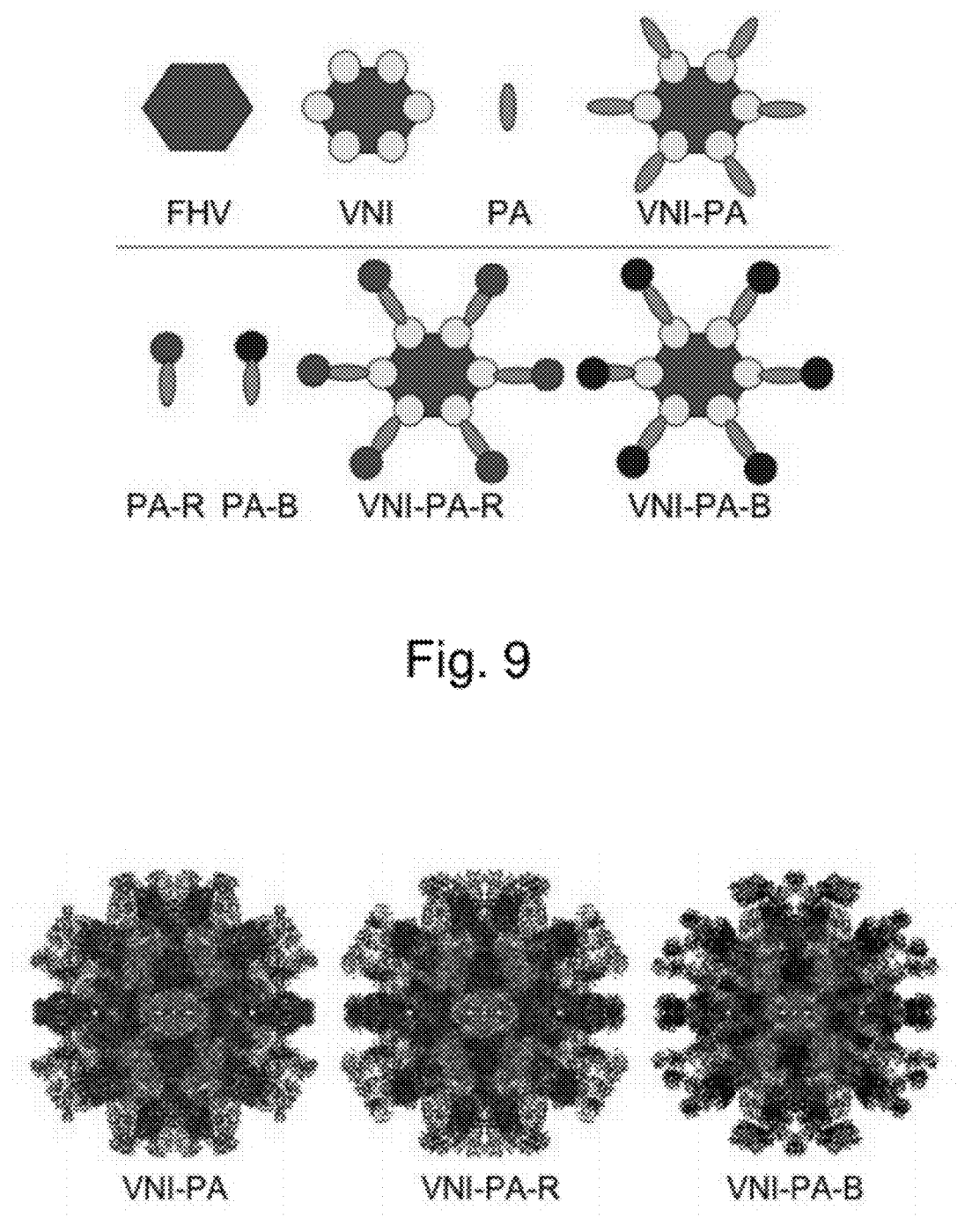

As shown in FIG. 9, the current example includes using the VNI platform to present multiple immunogens to the immune system. The strategy, in this example, is to fuse PA with antigenic portions of ricin or botulinum toxins (e.g. PA-R and PA-B, respectively). These fusion proteins are then multivalently arrayed on the surface of VNIs to generate combination vaccines.

The VNI-multivalent vaccine approach can circumvent the need for multiple dosings of immunogen, giving rise to a more rapid and efficient response. Moreover, by combining PA fusion proteins with the C-terminal domains of multiple BoNT serotypes (e.g. A, B, and E), it should be possible to use the VNI approach toward development of multivalent BoNT vaccines. This approach can be used to generate combination vaccines, which can simultaneously provide protection against, e.g., anthrax, botulinum A toxin (BoNT/A), and ricin toxin. In particular, by fusing immunogenic portions of other toxins such as ricin toxin or botulinum toxin with PA, the VNI platform is used to immunize against multiple toxins simultaneously (FIG. 9).

Use of the VNI platform to develop combination vaccines for additional pathogens. Here the ability to generate a combination VNI-based vaccine is discussed. Fusion proteins of PA and ricin toxin or botulinum A toxin are generated and arrayed on the surface of VNIs (FIG. 10). Immunization and challenge studies can be used to monitor immunity simultaneously generated against the toxins.

Generating an oligomerization- and cleavage-defective PA mutant. In this example, the use of the multivalent VNI platform employs altered versions of PA in which domain 1, also known as $PA_{20}$, is replaced with moieties from botulinum neurotoxin A and ricin A chain. To ensure that these heterologous moieties remain stably associated with PA and are not proteolytically removed by furin, a mutant version of PA is used in which the furin cleavage site is replaced with the amino acids SNKE. This mutation was previously shown to inhibit furin cleavage of PA (32). In addition, to ensure that the PA fusion proteins do not spontaneously heptamerize (a process normally inhibited in-cis by domain 1), an Asp to Lys mutation is introduced at position 512. This amino acid alteration inhibits PA heptamerization without compromising overall structure or receptor binding of PA (33). The mutations are engineered into wt PA using standard molecular cloning procedures. A cDNA of wt PA is currently available in the E. coli expression vector pET22b. The PA containing modifications at the furin cleavage site and at residue 512 are used throughout the example.

Generating and purifying PA-Ricin (PA-R) fusion protein from E. coli. Standard molecular cloning procedures are employed to replace the coding sequence of domain 1 (amino acids 1-167) in PA with that of ricin toxin A chain (RTA), to generate the PA-R fusion protein. A His-tag is added to the N terminus of RTA to facilitate purification of PA-R. The PA-R fusion construct is expressed in E. coli using vector pET22b. Protocols that closely follow those currently used for expression of wt PA are employed. The fusion protein is purified by affinity chromatography using a nickel column and if necessary, by FPLC using ion exchange or gel filtration chromatography. Purified protein is aliquoted and stored at −80° C.

Generating and purifying PA-botulinum (PA-B) fusion protein from E. coli. The carboxyterminal portion of the heavy chain of botulinum neurotoxin A (BoNT(A)), amino acids 873-1295 ($H_C$ region), are used to replace domain I of PA, to generate the PA-B fusion protein. In addition, an N terminal His tag is added to the BoNT(A) moiety to facilitate purification of the fusion protein. The PA-B fusion construct is expressed in E. coli using standard procedures that closely follow those currently used for expression of wt PA. The fusion protein is purified by affinity chromatography using a nickel column and if necessary, is further purified by FPLC using ion exchange chromatography. Purified PA-B is aliquoted and stored at −80° C.

Verifying correct folding of PA-R and PA-B. Correct folding of RTA in the context of PA-R is verified by confirming the enzymatic activity of the protein. To this end, purified PA-R is added to a cell-free lysate and inhibition of protein synthesis will be measured. Specifically, PA-R will be added to a rabbit reticulocyte lysate in the presence of $^{35}$S-methionine and mRNA, and incubated for 2 h at 37° C. Purified RTA chain (Vector Laboratories) is used as a positive control. Negative control samples do not receive toxin. Protein is precipitated with trichloroacetic acid and the amount of radioactivity incorporated is determined by liquid scintillation counting. Correct folding of the BoNT(A) domain is confirmed by immunoprecipitation with a conformation-specific antibody. Specifically, monoclonal antibody CR1 (34) is employed. This antibody was shown to bind with high affinity to a discontinuous epitope comprised of loops located in both the $H_{CN}$ and $H_{CC}$ domains. Incorrectly folded BoNT(A) $H_C$ domain is highly unlikely to bind to CR1. Alternatively, correct folding of BoNT(A) can be verified by confirming its function as a competitive inhibitor in the botulinum neurotoxin neutralization assay.

Scale-up and purification of PA-fusion proteins. The PA-R and PA-B fusion proteins are scaled up and purified from the periplasm of E. coli BL21 cells as described previously (35). These proteins are purified to homogeneity by FPLC with HiTrap QFF and Superose 12 (Amersham), or HiLoad Superdex 200 (Amersham), columns. The relative protein purity is then established by ImageQuant analysis (Amersham) of Coomassie-stained protein samples after SDS-PAGE as described before (35)).

Decorate VNI with PA fusion proteins and determine binding stoichiometry. VNI particles are decorated with PA-R and PA-B fusion proteins using the same protocol employed for decoration of VNI with wt PA. Integrity of decorated particles is verified by electron microscopy using negatively stained samples. The number of PA-R and PA-B molecules bound to VNI is determined biochemically using gel electrophoresis of purified complexes and quantification of bands corresponding to PA-R, PA-B and VNI as was done previously for VNI-PA.

Immunization of mice with VNI-PA-R and VNI-PA-B. Experiments employing live animals are conducted with a derivative of PA-R that contains two amino acid mutations in the ricin A chain (Y80A/V76M). Mutation Y80A prevents local vascular leakage in vaccinated individuals and mutation V76M inactivates the enzymatic activity of RTA. This double mutant of RTA was shown to be safe and immunogenic in mice and rabbits (36). Groups of 5-10 mice receive two subcutaneous injections of VNI-PA-R complex on day 0 and 21 following a protocol analogous to that described for vaccination of rats with VNI-PA. Adjuvants are not employed in these experiments. Serum samples are collected prior to priming as well as before and after boosting. Control animals are injected with VNI alone, vehicle alone, or RTA alone. Serum anti-RTA and anti-PA antibody levels and their toxin neutralization capacity are determined. One week after the boost (day 28) mice are challenged with an i.p. injection of 100 ng/g mouse of ricin (Inland Laboratories). This dose corresponds to 10-fold the $LD_{50}$ of ricin. Weights and death of the animals are monitored daily for 10 days. If animals survive ricin challenge, the experiment id repeated but mice are challenged 3-4 weeks after a single injection. The vaccination dose for a single injection is increased at least twofold.

The antibody response to vaccination with VNI-PA-R is measured by indirect ELISA. Specifically, serum samples collected prior, during and after vaccination are tested for the presence of antibodies against RTA, PA, ANTXR2, and FHV, the protein components of the VNI-PA-R complex. ELISA to measure anti-PA, anti-ANTXR2 and anti-FHV are done as described previously. To measure the anti-RTA response, 96-well plates are coated overnight with RTA (Vector Laboratories), blocked and incubated with serial dilutions of antiserum. Bound antibody is visualized using commercially available anti-mouse secondary IgG.

For vaccination with VNI-PA-B complex, groups of 5-10 mice receive two subcutaneous injections of VNI-PA-B complex on day 0 and 21 following a protocol analogous to that described for vaccination of rats with VNI-PA. Adjuvants are not employed in these experiments. Serum samples are collected prior to priming, as well as before and after boosting. Control animals are injected with VNI alone, BoNT(A) heavy chain alone (Metabiologics) or vehicle. Anti-BoNT(A) antibody levels and their toxin neutralization capacity is determined and one week after the second injection mice are challenged with an i.p. injection of 5-10 $LD_{50}$ BoNT/A (Metabiologics). Animals are monitored for signs of botulism overnight and the time to death/survival is recorded. If animals survive BoNT/A challenge, the experiment is repeated but mice are challenged 3-4 weeks after a single injection. The vaccination dose for a single injection is increased at least twofold.

The antibody response to vaccination with VNI-PA-B is measured by ELISA. Specifically, serum samples collected prior, during and after vaccination will be tested for the presence of antibodies to BoNT(A), PA, ANTXR2 I-domain, and FHV, the protein components constituting the VNI-PA-B complex. ELISA to measure anti-PA, -ANTXR2 I-domain, and -FHV is done as described previously. To measure anti-BoNT/A response, 96-well plates will be coated overnight with BoNT/A heavy chain (Metabiologics), blocked and probed with serial dilutions of antiserum Bound antibody is visualized using commercially available anti-mouse secondary IgG.

Test antibodies raised against VNI particles coated with PA-R or PA-B to neutralize anthrax lethal toxin, ricin or BoNT(A). The IgG antibodies raised in mice immunized subcutaneously with VNI particles coated with the PA fusion protein(s) are screened by cell culture-based toxin neutralization assays (TNAs) for their abilities to neutralize anthrax lethal toxin, ricin, or BoNT(A). The anthrax lethal toxin TNA is described above. The ricin TNA involves incubating serial dilutions of antiserum and ricin holotoxin (Inland Laboratories) prior to their addition to Vero cells. Cell survival is subsequently monitored using the MTT proliferation assay kit from the ATCC (37).

The BoNT(A) TNA involves mixing serial dilutions of antiserum and BoNT(A) (Metabiologics) prior to their addition to Neuro-2A cells. BoNT(A) activity is then monitored by subjecting protein lysates from the cells to SDS-PAGE and then immunoblotting with anti-SNAP25 antibody (Santa Cruz Biotechnology) and HRP-conjugated secondary antibody to detect the toxin cleaved form of SNAP-25 (38). Taken together these studies can be used to determine whether VNI particles coated with recombinant PA-R and PA-B fusion proteins can invoke the production of neutralizing antibodies against more than one toxin component. Moreover, by immunizing mice with a cocktail of VNI-PA, VNI-PA-R, and VNI-PA-B particles, or with VNI particles coated with different ratios of all 3 forms of the PA protein, it should be possible to generally vaccinate against these biowarfare agents.

Determining which steps in intoxication are blocked by neutralizing IgG antibodies raised against VNI-PA-R and VNI-PA-B. Assuming that, the VNI particles coated with PA-R or PA-B give rise to neutralizing antibodies against more than one toxin component it is useful to identify the functional classes of these antibodies. Therefore, they will be characterized to define the step of anthrax lethal toxin, ricin, and BoNT(A) intoxication which is the target for the neutralizing responses. The studies involving anthrax lethal toxin will be conducted as described above. The studies involving BoNT(A) employ the previously described immunofluorescence microscopy approach involving fixed Neuro-2A cells to discriminate between those antibodies which block toxin binding to cells from those that block toxin uptake (38). Similarly, immunofluorescence microscopy is used to monitor the effects of neutralizing antibodies on ricin uptake into cells via endocytosis followed by retrograde transport to the Golgi apparatus and endoplasmic reticulum prior to translocation to the cytosol, as described previously (39). Antibodies specific for ricin, for the endosomal marker EEA1, for the Golgi marker TGN46, and for the endoplasmic reticulum marker BiP are employed for these studies.

Performing in vivo spore or toxin challenge after immunization with VNI-PA vs. VNI-PA-R or VNI-PA-B. Once induction of immunity has been established, A/J mice will be challenged with *B. anthracis* Sterne spores, or with ricin toxin or botulinum toxin. Animals are inoculated i.p. with $4 \times 10^5$ spores and the lethality determined between 2-14 days post-inoculation. A duplicate set of animals are tested to determine whether protection from either ricin or BoNT(A) challenge occurs, as described above.

Determining whether combination or cocktail of particles can induce neutralizing immunity to all three pathogens. This experiment determines whether the simultaneous induction of immunity to all three pathogens occurs. To achieve this two approaches can be used. First, a "cocktail" of particles, mixing and equal quantity of VNI-PA-R and VNI-PA-B are used to immunize a large group of animals and, subsequently, subgroups are challenged with each of the three pathogens. In a second approach, a "chimeric" particle is generated where a mixture PA-R and PA-B are arrayed onto VNIs, to generate particles that display all three antigens together. A similar immunization and challenge strategy is then performed.

EXAMPLE 2 REFERENCES

1. M. Mock, A. Fouet, Annu Rev Microbiol 55, 647 (2001).
2. G. F. Webb, Proc Natl Acad Sci USA 100, 4355 (Apr. 15, 2003).
3. J. A. Young, R. J. Collier, Annu Rev Biochem (Mar. 2, 2007).
4. S. H. Leppla, Proc Natl Acad Sci USA 79, 3162 (May, 1982).
5. K. A. Bradley, J. Mogridge, M. Mourez, R. J. Collier, J. A. Young, Nature 414, 225 (Nov. 8, 2001).
6. H. M. Scobie, G. J. Rainey, K. A. Bradley, J. A. Young, Proc Natl Acad Sci USA 100, 5170 (Apr. 29, 2003).
7. D. B. Lacy, D. J. Wigelsworth, R. A. Melnyk, S. C. Harrison, R. J. Collier, Proc Natl Acad Sci USA 101, 13147 (Sep. 7, 2004).
8. E. Santelli, L. A. Bankston, S. H. Leppla, R. C. Liddington, Nature 430, 905 (Aug. 19, 2004).
9. D. J. Wigelsworth et al., J Biol Chem 279, 23349 (May 28, 2004).
10. H. M. Scobie et al., J Infect Dis 192, 1047 (Sep. 15, 2005).
11. W. Wei, Q. Lu, G. J. Chaudry, S. H. Leppla, S. N. Cohen, Cell 124, 1141 (Mar. 24, 2006).
12. J. J. Young et al., PLoS Pathog 3, e27 (Mar. 2, 2007).
13. A. Friedlander, P. Pittman, G. Parker, Jama 282 (1999).
14. M. J. McConnell, P. C. Hanna, M. J. Imperiale, Mol Ther 15, 203 (January, 2007).
15. M. F. Bachmann et al., Science 262, 1448 (Nov. 26, 1993).
16. L Hangartner, R. M. Zinkernagel, H. Hengartner, Nat Rev Immunol 6, 231 (March, 2006).
17. H. M. Dintzis, R. Z. Dintzis, B. Vogelstein, Proc Natl Acad Sci USA 73, 3671 (October, 1976).
18. P. Lenz, D. R. Lowy, J. T. Schiller, Eur J Immunol 35, 1548 (May, 2005).
19. A. Schneemann, V. Reddy, J. E. Johnson, in Advances in virus research K. Maramorsch, F. A. Murphy, A. J. Shatkin, Eds. (Academic Press, San Diego, 1998), vol. 50, pp. 381-446.
20. A. Schneemann, R. Dasgupta, J. E. Johnson, R. R. Rueckert, J. Virol. 67, 2756 (1993).
21. D. J. Manayani et al., Submitted (2007).
22. E. Ravichandran et al., Infect Immun (Mar. 19, 2007).
23. M. Maddaloni et al., J Immunol 177, 5524 (Oct. 15, 2006).
24. M. Kende et al., Vaccine 25, 3219 (Apr. 20, 2007).
25. L. Vitale et al., Infect Immun 74, 5840 (October, 2006).
26. C. S. Rae et al., Virology 343, 224 (Dec. 20, 2005).
27. S. E. Bell et al., J Cell Sci 114, 2755 (August, 2001).
28. G. J. Rainey et al., Proc Natl Acad Sci USA 102, 13278 (Sep. 13, 2005).
29. S. Welkos, S. Little, A. Friedlander, D. Fritz, P. Fellows, Microbiology 147, 1677 (June, 2001).
30. M. Barat-Houari et al., BMC Genomics 7, 160 (2006).
31. B. D. Price, P. Ahlquist, L. A. Ball, J Virol 76, 1610 (February, 2002).
32. V. M. Gordon, K. R. Klimpel, N. Arora, M. A. Henderson, S. H. Leppla, Infect Immun 63, 82 (January, 1995).
33. J. Mogridge, K Cunningham, D. B. Lacy, M. Mourez, R. J. Collier, Proc Natl Acad Sci USA 99, 7045 (May 14, 2002).
34. C. Garcia-Rodriguez et al., Nat Biotechnol 25, 107 (January, 2007).
35. H. M. Scobie et al., PLoS Pathog 2 (Oct. 20, 2006).
36. J. E Smallshaw, J. A. Richardson, S. Pincus, J. Schindler, E. S. Vitetta, Vaccine 23, 4775 (Sep. 15, 2005).
37. C. R. McGuinness, N. J. Mantis, Infect Immun 74, 3463 (June, 2006).
38. M. Dong et al., Science 312, 592 (Apr. 28, 2006).
39. A. Utskarpen, H. H. Slagsvold, T. G. Iversen, S. Walchli, K. Sandvig, Traffic 7, 663 (June, 2006).

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. An immunogenic composition comprising a nodavirus-derived virus like particle (VLP) that comprises a heterologous immunogen binding domain, said heterologous binding domain comprising an anthrax binding sequence of an extracellular von Willebrand factor A (VWA) domain, which binding domain is bound to a first heterologous immunogen, wherein the heterologous immunogen comprises a first domain and a second domain, wherein the first domain comprises an anthrax protective antigen and the second domain comprises a botulinum antigen.

2. The immunogenic composition of claim 1, wherein the VLP is derived from Flock House Virus (FHV).

3. The immunogenic composition of claim 1, wherein the VLP comprises 180 binding domains coupled to up to a maximum of about 120 heterologous immunogens.

4. The immunogenic composition of claim 1, wherein the binding domain comprises a VWA domain of capillary morphogenesis protein 2 (ANTRX2).

5. The immunogenic composition of claim 4, wherein the first and second domains are recombinantly expressed as a fusion protein, and the first domain is bound by the VWA domain of ANTRX2.

6. The immunogenic composition of claim 1, wherein the VLP comprises a plurality of heterologous immunogen binding domains on the surface of the VLP, wherein a first and second heterologous immunogen are each bound, respectively, to one of the heterologous immunogen binding domains, wherein said first and second heterologous immunogen each comprising a first domain and a second domain, wherein the first domain comprises an anthrax protective antigen and the second domain comprises an antigen selected from ricin toxin, botulinum toxin and other immunogens, wherein the second domain of the first and second heterologous immunogens are different.

7. The immunogenic composition of claim 6, wherein the second domain of the first heterologous immunogen comprises a domain derived from botulinum A toxin and the second domain of the second heterologous immunogen comprises a domain derived from ricin toxin.

8. An immunogenic composition comprising a nodavirus-derived virus like particle (VLP) derived from Flock House Virus, said VLP comprising a heterologous immunogen binding domain, said binding domain being bound to a first heterologous immunogen, said heterologous immunogen comprising a first anthrax protective antigen domain coupled to a second heterologous domain comprising a botulinum toxin.

9. An immunogenic composition comprising a first and second nodavirus-derived virus like particle (VLP) wherein the first VLP is different from the second VLP, wherein the first and second VLPs each comprise a VWA domain of capillary morphogenesis protein 2 (ANTRX2) bound to a respective first and second heterologous immunogen, further wherein the first and second heterologous immunogen each comprise a fusion protein, said fusion protein comprising a first domain derived from anthrax protective antigen and a second domain selected from a ricin toxin antigen, botulinum toxin antigen, or other immunogen of interest, wherein the second domain of the first and second heterologous immunogens are different.

10. The immunogenic composition of claim 9, wherein the first and second VLPs are each is derived from Flock House Virus (FHV).

11. The immunogenic composition of claim 8, wherein the heterologous binding domain comprises a VWA domain of capillary morphogenesis protein 2.

* * * * *